(12) United States Patent
Cui et al.

(10) Patent No.: US 12,006,305 B2
(45) Date of Patent: Jun. 11, 2024

(54) SALTS OF OBICETRAPIB AND PROCESSES FOR THEIR MANUFACTURE AND INTERMEDIATES THEREOF

(71) Applicant: NewAmsterdam Pharma B.V., Naarden (NL)

(72) Inventors: Sheng Cui, Lexington, MA (US); Andreas René Rötheli, Wellesley, MA (US); Christopher J. Borths, Sherborn, MS (US); Muneki Kishida, Osaka (JP)

(73) Assignee: NewAmsterdam Pharma B.V., Naarden (NL)

( * ) Notice: Subject to any disclaimer, the term of this patent is extended or adjusted under 35 U.S.C. 154(b) by 0 days.

(21) Appl. No.: 18/346,342

(22) Filed: Jul. 3, 2023

(65) Prior Publication Data

US 2024/0010630 A1    Jan. 11, 2024

Related U.S. Application Data

(60) Provisional application No. 63/358,363, filed on Jul. 5, 2022.

(51) Int. Cl.
*C07D 401/12* (2006.01)
*A61K 31/33* (2006.01)
*A61P 9/00* (2006.01)

(52) U.S. Cl.
CPC ............ *C07D 401/12* (2013.01); *A61K 31/33* (2013.01); *A61P 9/00* (2018.01); *C07B 2200/13* (2013.01)

(58) Field of Classification Search
CPC ......... C07D 401/12; A61K 31/33; A61P 9/00; C07B 2200/13
See application file for complete search history.

(56) References Cited

U.S. PATENT DOCUMENTS

| 6,313,142 | B1 | 11/2001 | Damon et al. |
| 7,872,126 | B2 | 1/2011 | Kubota et al. |
| 8,084,611 | B2 | 12/2011 | Okamoto et al. |
| 8,158,640 | B2 | 4/2012 | Kubota et al. |
| 10,112,904 | B2 * | 10/2018 | Ford ............... C07D 401/12 |
| 10,300,059 | B2 | 5/2019 | Ford et al. |

(Continued)

FOREIGN PATENT DOCUMENTS

| EP | 0412848 A2 | 2/1991 |
| EP | 0456442 A1 | 11/1991 |

(Continued)

OTHER PUBLICATIONS

Hancock, B.C., Parks, M. What is the True Solubility Advantage for Amorphous Pharmaceuticals? Pharm. Res., 2000, 17, 397-404 (Year: 2000).*

(Continued)

*Primary Examiner* — Joseph R Kosack
*Assistant Examiner* — David M Shim
(74) *Attorney, Agent, or Firm* — Fenwick & West LLP

(57) ABSTRACT

Provided herein is a method for the manufacture of a compound of obicetrapib and salts thereof, such as calcium salts thereof. Also provided herein is amorphous obicetrapib hemicalcium. New intermediates for use in the synthesis of obicetrapib, and salts thereof are also provided, including obicetrapib HCl and a mesylate salt for the use in the synthesis of obicetrapib and amorphous obicetrapib hemicalcium.

27 Claims, 28 Drawing Sheets

(56) References Cited

U.S. PATENT DOCUMENTS

| | | |
|---|---|---|
| 10,653,692 B2 | 5/2020 | Ford et al. |
| 11,013,742 B2 | 5/2021 | Ford et al. |
| 11,642,344 B2 | 5/2023 | Ford et al. |
| 2007/0082896 A1* | 5/2007 | Kubota ............... A61K 31/541 |
| | | 514/227.8 |

FOREIGN PATENT DOCUMENTS

| | | | |
|---|---|---|---|
| EP | 1125929 A1 | 8/2001 | |
| JP | 2007-119450 A | 5/2007 | |
| WO | WO 2005/095409 A2 | 10/2005 | |
| WO | WO 2007/116922 A1 | 10/2007 | |
| WO | WO 2014/178040 A1 * | 11/2014 | ............... C07H 7/04 |
| WO | WO 2015/119495 A1 | 8/2015 | |
| WO | WO 2016/024858 A1 | 2/2016 | |
| WO | WO 2016/032324 A1 | 3/2016 | |
| WO | WO 2017/023165 A1 | 2/2017 | |
| WO | WO 2017/023166 A1 | 2/2017 | |
| WO | WO 2022/177428 A1 | 8/2022 | |
| WO | WO 2022/185120 A1 | 9/2022 | |
| WO | WO 2023/006657 A1 | 2/2023 | |
| WO | WO 2023/129595 A1 | 7/2023 | |

OTHER PUBLICATIONS

Prakash Khadka, Jieun Ro, Hyeongmin Kim, Iksoo Kim, Jeong Tae Kim, Hyunil Kim, Jae Min Cho, Gyiae Yun, Jaehwi Lee, Pharmaceutical particle technologies: An approach to improve drug solubility, dissolution and bioavailability, Asian Journal of Pharmaceutical Sci., 2014, 9:304-316 (Year: 2014).*

Vranić E. Amorphous pharmaceutical solids. Bosn J Basic Med Sci., 2004,4:35-39 (Year: 2004).*

Satoshi Ohtake, Evgenyi Shalaev, Effect of Water on the Chemical Stability of Amorphous Pharmaceuticals: I. Small Molecules, Journal of Pharmaceutical Sciences, 2013, 102: 1139-1154 (Year: 2013).* clinicaltrials.gov, "Evaluation of Safety, Tolerability, Pharmacokinetics and Pharmacodynamics of TA-8995 With Single, Escalating Doses in Healthy Subjects," ClinicalTrials.gov Identifier: NCT01878474, Jun. 17, 2013, five pages, [Online] [Retrieved on Sep. 12, 2020] Retrieved from the Internet <URL: https://clinicaltrials.gov/ct2/show/NCT01878474?term=NCT01878474>.

clinicaltrials.gov, "Evaluation of Safety, Tolerability, Pharmacokinetics and Pharmacodynamics of TA-8995 After Multiple Doses in Healthy Subjects," ClinicalTrials.gov Identifier: NCT01879020, Jun. 17, 2013, five pages, [Online] [Retrieved on Sep. 12, 2020] Retrieved from the Internet <URL: https://clinicaltrials.gov/ct2/show/NCT01879020?term=nct01879020>.

clinicaltrials.gov, "TA-8995: Its Use in Patients With Mild Dyslipidaemia (TULIP) (TULIP)," ClinicalTrials.gov Identifier: NCT01970215, Aug. 21, 2014, six pages, [Online] [Retrieved on Sep. 12, 2020] Retrieved from the Internet <URL: https://clinicaltrials.gov/ct2/show/NCT01970215>.

clinicaltrials.gov, "A Phase I, Open Label Study to Assess the Effects of TA-8995 on the Pharmacokinetics of Midazolam and Digoxin in Healthy Male Subjects," ClinicalTrials.gov Identifier: NCT02124954, Oct. 3, 2016, four pages, [Online] [Retrieved on Sep. 12, 2020] Retrieved from the Internet <URL: https://clinicaltrials.gov/ct2/show/NCT02124954?term=ta-8995>.

clinicaltrials.gov, "Study of the Electrocardiographic Effects of TA-8995," ClinicalTrials.gov Identifier: NCT02241759, February 16, 2015, four pages, [Online] [Retrieved on Sep. 12, 2020] Retrieved from the Internet <URL: https://clinicaltrials.gov/ct2/show/NCT02241759?term=ta-8995>.

clinicaltrials.gov, "A Study on the Effects of TA-8995 on Lp(a) in Subjects With Elevated Lp(a)," ClinicalTrials.gov Identifier: NCT02241772, Feb. 16, 2015, three pages, [Online] [Retrieved on Sep. 12, 2020] Retrieved from the Internet <URL: https://clinicaltrials.gov/ct2/show/NCT02241772?term=ta-8995>.

clinicaltrials.gov, "ADME Study in Healthy Male Subjects With TA-8995," ClinicalTrials.gov Identifier: NCT02408055, Oct. 3, 2016, three pages, [Online] [Retrieved on Sep. 12, 2020] Retrieved from the Internet <URL: https://clinicaltrials.gov/ct2/show/NCT02408055?term=ta-8995>.

clinicaltrials.gov, "A Phase I, Randomised, Open-label Cross-over Bioequivalence Study of Capsule and Tablet Formulations of TA-8995 in Healthy Male Subjects," ClinicalTrials.gov Identifier: NCT02523391, Aug. 14, 2015, five pages, [Online] [Retrieved on Sep. 20, 2023] Retrieved from the Internet <URL: https://classic.clinicaltrials.gov/ct2/show/NCT02523391>.

clinicaltrials.gov, "A Placebo-Controlled, Double-Blind, Randomized, Phase 2 Dose-Finding Study to Evaluate the Effect of Obicetrapib as an Adjunct to High-Intensity Statin Therapy," ClinicalTrials.gov Identifier NCT04753606, Feb. 15, 2021, 6 pages, [Online] [Retrieved on Sep. 11, 2023] Retrieved from the Internet <URL: https://classic.clinicaltrials.gov/ct2/show/NCT04753606>.

clinicaltrials.gov, "A Placebo-Controlled, Double-Blind, Randomized Phase 2 Study to Evaluate the Effect of Obicetrapib in Combination With Ezetimibe in Participants With Mild Dyslipidemia," ClinicalTrials.gov Identifier NCT04770389, Feb. 25, 2021, 8 pages, [Online] [Retrieved on Sep. 11, 2023] Retrieved from the Internet <URL: https://classic.clinicaltrials.gov/ct2/show/NCT04770389>.

clinicaltrials.gov, "A Placebo-Controlled, Double-Blind, Randomized Phase 3 Study to Evaluate the Effect of 10mg Obicetrapib in Participants With HeFH and/or ASCVD and LDL-C ≥70 and <100 mg/dL Who Are Not Adequately Controlled by Their Lipid Modifying Therapies," ClinicalTrials.gov Identifier: NCT05142722, Dec. 3, 2021, eight pages, [Online] [Retrieved on Sep. 20, 2023] Retrieved from the Internet <URL: https://classic.clinicaltrials.gov/ct2/show/NCT05142722>.

clinicaltrials.gov, "A Phase 2a, Proof-of-Concept, Open-Label Study to Evaluate the Pharmacodynamics, Pharmacokinetics, and Safety of Obicetrapib in Patients With Early Alzheimer's Disease (Hetero/Homozygote APOE4 Carriers)," ClinicalTrials.gov Identifier NCT05161715, Dec. 17, 2021, six pages, [Online] [Retrieved on Sep. 11, 2023] Retrieved from the Internet <URL: https://classic.clinicaltrials.gov/ct2/show/NCT05161715>.

clinicaltrials.gov, "Placebo Controlled, Double Blind, Randomized Cardiovascular Outcome Study to Evaluate the Effect of 10 mg Obicetrapib in Participants With ASCVD Not Adequately Controlled Despite Maximally Tolerated Lipid Modifying Therapies," ClinicalTrials.gov Identifier: NCT05202509, Jan. 21, 2022, five pages, [Online] [Retrieved on Sep. 11, 2023] Retrieved from the Internet <URL: https://classic.clinicaltrials.gov/ct2/show/NCT05202509>.

clinicaltrials.gov, "A Placebo-Controlled, Double-Blind, Randomized, Phase 2 Study to Evaluate the Effect of Obicetrapib 10 mg Daily in Combination With Ezetimibe 10 mg Daily as an Adjunct to High-Intensity Statin Therapy: The ROSE 2 Study," ClinicalTrials.gov Identifier NCT05266586, Mar. 4, 2022. 7 pages, [Online] [Retrieved on Sep. 11, 2023] Retrieved from the Internet <URL: https://classic.clinicaltrials.gov/ct2/show/NCT05266586>.

clinicaltrials.gov, "A Placebo-Controlled, Double-Blind, Randomized, Phase 2 Dose-Finding Study to Evaluate the Effect of Obicetrapib as an Adjunct to Stable Statin Therapy in Japanese Subjects," ClinicalTrials.gov Identifier: NCT05421078, Jun. 16, 2022, seven pages, [Online] [Retrieved on Sep. 20, 2023] Retrieved from the Internet <URL: https://classic.clinicaltrials.gov/ct2/show/study/NCT05421078>.

clinicaltrials.gov, "A Placebo-Controlled, Double-Blind, Randomized, Phase 3 Study to Evaluate the Effect of 10 mg Obicetrapib in Participants With a History of HeFH Who Are Not Adequately Controlled by Their Lipid Modifying Therapies," ClinicalTrials.gov Identifier: NCT05425745, Jun. 21, 2022, six pages, [Online] [Retrieved on Sep. 20, 2023] Retrieved from the Internet <URL: https://classic.clinicaltrials.gov/ct2/show/study/NCT05425745>.

EU Clinical Trials Register, "A Multi-Centre, Randomised, Double Blind, Placebo Controlled, Parallel Group Study of TA 8995 in Patients with Mild Dyslipidaemia, Alone and In Combination with Statin Therapy," EudraCT No. 2012-005643-24, Jul. 2013, pp. 1-7, Retrieved from the Internet: https://www.clinicaltrialsregister.eu/ctr-search/trial/2012-005643-24/NL>.

(56) References Cited

OTHER PUBLICATIONS

EU Clinical Trials Register, "A Placebo-Controlled, Double-Blind, Randomized Phase 2Study to Evaluate the Effect of Obicetrapib in Combination with Ezetimibe in Participants with Mild Dyslipidemia," EudraCT No. 2019-004935-22, Jun. 30, 2021 (Jun. 30, 2021), p. 1-6, Retrieved from the Internet: URL: https://www.clinicaltrialsregister.eu/ctr-search/trial/2019-004935-22/NL#C>.

EU Clinical Trials Register, "A Phase 2a, Proof-of-Concept, Open-Label Study to Evaluate the Pharmacodynamics, Pharmacokinetics, and Safety of Obicetrapib in Patients with Early Alzheimer's Disease (Hetero/Homozygote APOE4 Carriers)," EudraCT No. 2021-002687-41, Aug. 9, 2021 (Aug. 9, 2021), Trial Status: Ongoing, pp. 1-6, Retrieved from the Internet: https://www.clinicaltrialsregister.eu/ctr-search/trial/2021-002687-41/NL>.

EU Clinical Trials Register, "A Placebo-Controlled Phase 3 Study to Evaluate the Effect of 10 mg Obicetrapib in Participants With Atherosclerotic Cardiovascular Disease (ASCVD) Whose Current Treatment with Lipid-Modifying Therapies is not Sufficiently Effective," EudraCT No. 2021-005092-39, Jan. 27, 2022 (Jan. 27, 2022), pp. 1-5, Retrieved from the Internet: https://www.clinicaltrialsregister.eu/ctr-search/trial/2021-005092-39/DE>.

EU Clinical Trials Register, "Obicetrapib on Top of Maximum Tolerated Lipid-Modifying Therapies (BROOKLYN): A Placebo-Controlled, Double-Blind, Randomized, Phase 3 Study to Evaluate the Effect of 10 mg Obicetrapib in Participants With a History of HeFH and LDL-C ≥70 mg/dL Who are Not Adequately Controlled by Their Lipid-Modifying Therapies," EudraCT No. 2021-005064-22, Jul. 19, 2022 (Jul. 19, 2022), Trial Status: Ongoing, pp. 1-6, Retrieved from the Internet: https://www.clinicaltrialsregister.eu/ctr-search/trial/2021-005064-22/ES>.

EU Clinical Trials Register, "Obicetrapib on Top of Maximum Tolerated Lipid-Modifying Therapies (BROADWAY): A Placebo-Controlled, Double-Blind, Randomized Phase 3 Study to Evaluate the Effect of 10 mg Obicetrapib in Participants With Underlying HeFH and/or Atherosclerotic Cardiovascular Disease (ASCVD) Who are Not Adequately Controlled by Their Lipid Modifying Therapies," EudraCT No. 2021-005065-40, Mar. 1, 2022 (Mar. 1, 2022), Trial Status: Ongoing, pp. 1-6, Retrieved from the Internet: https://www.clinicaltrialsregister.eu/ctr-search/trial/2021-005065-40/NL>.

Ballantyne C.M. et al., "Obicetrapib plus ezetimibe as an adjunct to high-intensity statin therapy: A randomized phase 2 trial," Journal of Clinical Lipidology, May 29, 2023, 000, pp. 1-13.

Ford, J. et al., "Tolerability, pharmacokinetics and pharmacodynamics of TA-8995, a selective cholesteryl ester transfer protein (CETP) inhibitor, in healthy subjects," British Journal of Clinical Pharmacology, vol. 78, No. 3, Mar. 17, 2014, pp. 498-508.

Hovingh, G.K. et al., "Cholesterol ester transfer protein inhibition by TA-8995 in patients with mild dyslipidemia (TULIP): a randomised, double-blind, placebo-controlled phase 2 trial," The Lancet, vol. 386, Iss. 9992, Jun. 2, 2015, pp. 452-460.

Khomtchouk B.B. et al., "CETP and SGLT2 inhibitor combination therapy improves glycemic control," medRxiv preprint, Jun. 16, 2023, pp. 1-28, [Online] [Retrieved on Oct. 2, 2023] Retrieved from the Internet <URL: https://www.medrxiv.org/content/10.1101/2023.06.13.23291357v1>.

Nicholls, S.J. et al., "Lipid lowering effects of the CETP inhibitor obicetrapib in combination with high-intensity statins: a randomized phase 2 trial," Nature Medicine 28, Aug. 11, 2022, pp. 1672-1678.

Van Capelleveen, J.C. et al., "Effects of the cholesteryl ester transfer protein inhibitor, TA-8995, on cholesterol efflux capacity and high-density lipoprotein particle subclasses," Journal of Clinical Lipidology, vol. 10, Iss. 5, Jun. 25, 2016, pp. 1137-1144.E3.

PCT International Search Report and Written Opinion, PCT Application No. PCT/IB2023/000392, Nov. 27, 2023, 18 pages.

Escribano, A. et al., "Design and synthesis of new tetrahydroquinolines derivatives as CETP inhibitors," Bioorganic & Medicinal Chemistry Letters, vol. 22, Apr. 13, 2012, pp. 3671-3675.

Katritzky, A.R. et al., "Synthesis of Pyrido[4,3,2-de]quinazolines via Nitro-Substituted Tetrahydroquinolines," J. Heterocyclic Chem., vol. 36, May 1999, pp. 755-759.

Mearns, B.M. et al., "Dyslipidaemia: Promising results for TA-8995 in TULIP," Nature Reviews, Cardiology, vol. 12, Jun. 23, 2015, pp. 443.

Rano, T.A. et al., "Design and synthesis of potent inhibitors of cholesteryl ester transfer protein (CETP) exploiting a 1,2,3,4-tetrahydroquinoline platform," Bioorganic & Medicinal Chemistry Letters, vol. 19, Mar. 18, 2009, pp. 2456-2460.

Kanaujia P et al: "Amorphous formulations for dissolution and bioavailability enhancement of poorly soluble APIs", Powder Technology, vol. 285, May 15, 2015, pp. 2-15.

Lee, S. et al., "Handbook of Pharmaceutical Salts: Properties, Selection, and Use, Chapter 8 (Large-Scale Aspects of Salt Formation: Processing of Intermediates and Final Products), Chapter 12 (Monographs on Acids and Bases)," Jan. 1, 2002, Handbook of Pharmaceutical Salts: Properties, Selection, and Use, Wiley-Vch, Weinheim, pp. 191-192, 211-214, 265-266, and 282-283.

PCT Invitation to Pay Additional Fees, PCT Application No. PCT/IB2023/000392, Oct. 4, 2023, 12 pages.

\* cited by examiner

SALTS OF OBICETRAPIB AND PROCESSES FOR THEIR MANUFACTURE AND INTERMEDIATES THEREOF

CROSS-REFERENCE TO RELATED APPLICATIONS

This application claims the benefit of and priority to U.S. Provisional Application No. 63/358,363, filed Jul. 5, 2022, which is hereby incorporated by reference in its entirety.

INTRODUCTION

Prospective epidemiological studies have shown a strong association between low density lipoprotein-cholesterol (LDL-C) levels and cardiovascular disease (CVD) risk. The application of statin therapy to decrease these atherogenic LDL-C levels has resulted in a marked reduction of CVD-related morbidity and mortality: every 1 mmol/L decrease in LDL-C results in an estimated 22% reduction of CVD events and a 10% reduction of all-cause mortality. Notwithstanding these impressive benefits, a large residual disease burden persists that has a large impact on both individual patients as well as on global healthcare costs. Novel therapeutics are required to reduce further this residual CVD risk in patients.

One route which reduces LDL-C and elevates high-density lipoprotein cholesterol (HDL-C) levels is to inhibit Cholesterol Ester Transfer Protein (CETP). CETP is a plasma protein secreted primarily by liver and adipose tissue. CETP mediates the transfer of cholesteryl esters from HDL to apolipoprotein B (Apo B)-containing particles (mainly LDL and very low density lipoprotein VLDL) in exchange for triglycerides, thereby decreasing the cholesterol content in HDL in favor of that in VLDL. Hence, CETP inhibition has been hypothesized to retain cholesteryl esters in HDL-C and decrease the cholesterol content of the atherogenic Apo B fraction.

Clinical studies have shown that obicetrapib also known as ((2R,4S)-4-{[3,5 bis(trifluoromethyl)benzyl]-[5-(3-carboxypropoxy)pyrimidin-2-yl]amino}-2-ethyl-6-trifluoromethyl-3,4-dihydro-2H-quinoline-1-carboxylic acid ethyl ester), or a pharmaceutically acceptable salt thereof is a potent CETP-inhibitor. The structure of obicetrapib is set forth in Formula (I) below:

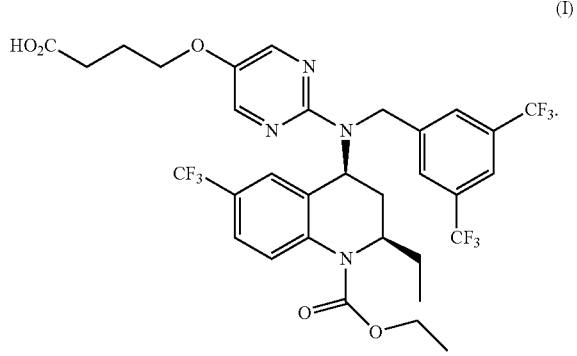 [SMILES: CCOC(=O)N1c2ccc(C(F)(F)F)cc2[C@@H](N(Cc2cc(C(F)(F)F)cc(C(F)(F)F)c2)c2ncc(OCCCC(=O)O)cn2)C[C@H]1CC]

(I)

The preparation of obicetrapib is disclosed, for example, in U.S. Pat. No. 7,872,126. Example 177 teaches the formation of obicetrapib, which, as seen in Formula (I), is a free acid. Example 178 teaches the formation of a sodium salt of obicetrapib from obicetrapib by exchanging the acidic proton of the free acid moiety of obicetrapib with a sodium atom. In Example 179, a calcium salt of obicetrapib is taught. Because calcium is an alkaline earth metal, when it ionizes, it has a +2 charge. Thus, a neutral salt will have two obicetrapib anions (each being obicetrapib minus a proton from its carboxylic acid group) for each calcium cation. The resulting salt of Example 179 is a hemicalcium salt in that there are only half as many calcium atoms as obicetrapib anions in a neutral amorphous obicetrapib calcium salt molecule.

The molecular formula of amorphous obicetrapib hemicalcium is $(C_{32}H_{30}N_4O_5F_9)_2Ca$. When discussing salts of obicetrapib, such as calcium salts and in particular the hemicalcium salt, it is understood that obicetrapib has lost a proton in order to make such a salt. Thus, the term amorphous obicetrapib hemicalcium means that each obicetrapib moiety portion of the salt is not Formula (I) (i.e., obicetrapib) but Formula (I) minus a proton. Example 179 expressly teaches that the hemicalcium salt of obicetrapib resulting is crystalline; however, the crystalline form has undesirable properties, such as its poor physical stability.

Compared to other known CETP-inhibitors, only a relatively low dose of obicetrapib is needed to reach near complete CETP inhibition. Typically, repeated daily dosages (once a day) as low as 2.5 mg of the compound of obicetrapib have proven to be already sufficient to reach near complete CETP inhibition. These are considerably lower dosages than had to be used for other CETP-inhibitors. Moreover, clinical studies have also shown that obicetrapib is well tolerated and that it does not lead to serious side effects.

While processes have been described for the manufacture of obicetrapib (see, e.g., WO 2005/095409A2 and U.S. Pat. Nos. 7,872,126 and 8,158,640, Examples 1 and 177-180; WO 2007/116922 A1 and U.S. Pat. No. 8,084,611; and WO 2016/024858 and U.S. Pat. No. 10,112,904) the prior art produces an unfavorable solid form. These references are incorporated herein by reference in their entirety.

In addition, the previously described processes have relatively low yield and are not particularly suitable for carrying out on an industrial scale. Thus, there is a need for improved solid forms of obicetrapib and alternative processes for the manufacture of obicetrapib and pharmaceutically acceptable salts thereof with an improved yield, purity, and stability.

SUMMARY OF THE INVENTION

The present disclosure provides for an amorphous calcium salt of obicetrapib such as, for example, amorphous obicetrapib hemicalcium.

The present disclosure further provides HCl obicetrapib, including crystalline obicetrapib HCl compounds, and other compounds useful as intermediates in the manufacture of obicetrapib such as compounds of Formula (VI) and Compound 1D, including crystalline Compound 1D.

The present disclosure provides methods for (i) the manufacture of obicetrapib, including intermediates, such as the crystalline obicetrapib HCl compounds, (ii) the manufacture of other compounds useful as intermediates in the manufacture of obicetrapib such as compounds of Formula (VI) and Compound 1D, including crystalline Compound 1D, and (iii) the manufacture of amorphous calcium salts of obicetrapib such as amorphous obicetrapib hemicalcium.

The present disclosure also provides for pharmaceutical compositions comprising amorphous obicetrapib calcium salts, such as, for example, amorphous obicetrapib hemicalcium, and one or more pharmaceutically acceptable carriers.

The present disclosure further provides for methods of treating patients suffering from or having an increased risk of developing a cardiovascular disease comprising administering amorphous obicetrapib calcium salts, such as amorphous obicetrapib hemicalcium, to such patients.

BRIEF DESCRIPTION OF THE DRAWINGS

These and other features, aspects, and advantages of the present invention will become better understood with regard to the following description, and accompanying drawings where.

DETAILED DESCRIPTION OF THE INVENTION

In many embodiments of the disclosure, amorphous obicetrapib calcium salts are provided. In particular, amorphous obicetrapib hemicalcium is provided. The disclosure is further directed to various methods of making amorphous obicetrapib calcium and in particular, amorphous obicetrapib hemicalcium.

Figure 1:
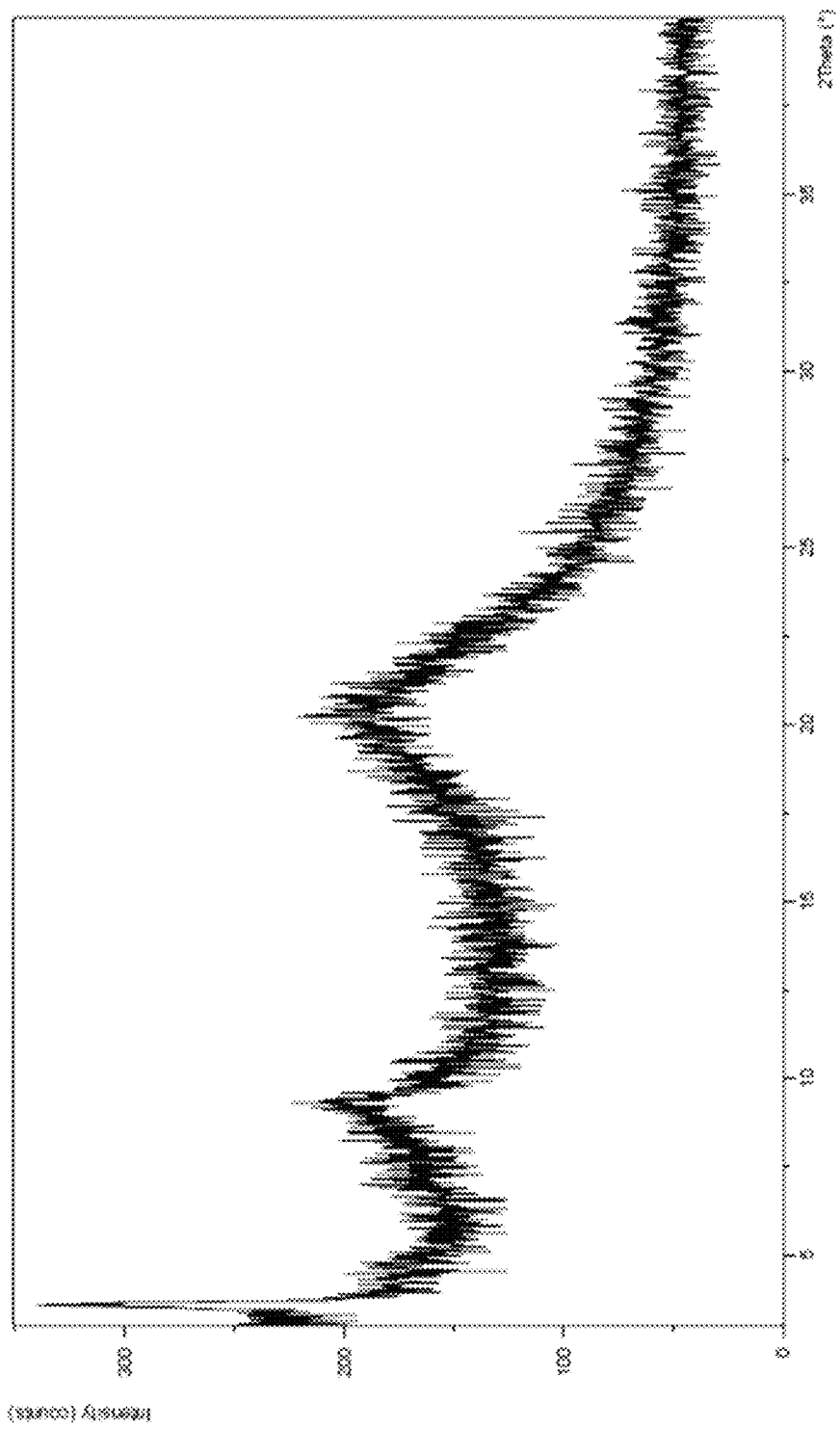
FIG. 1 is an x-ray powder diffraction pattern of amorphous obicetrapib hemicalcium.
Figure 2:
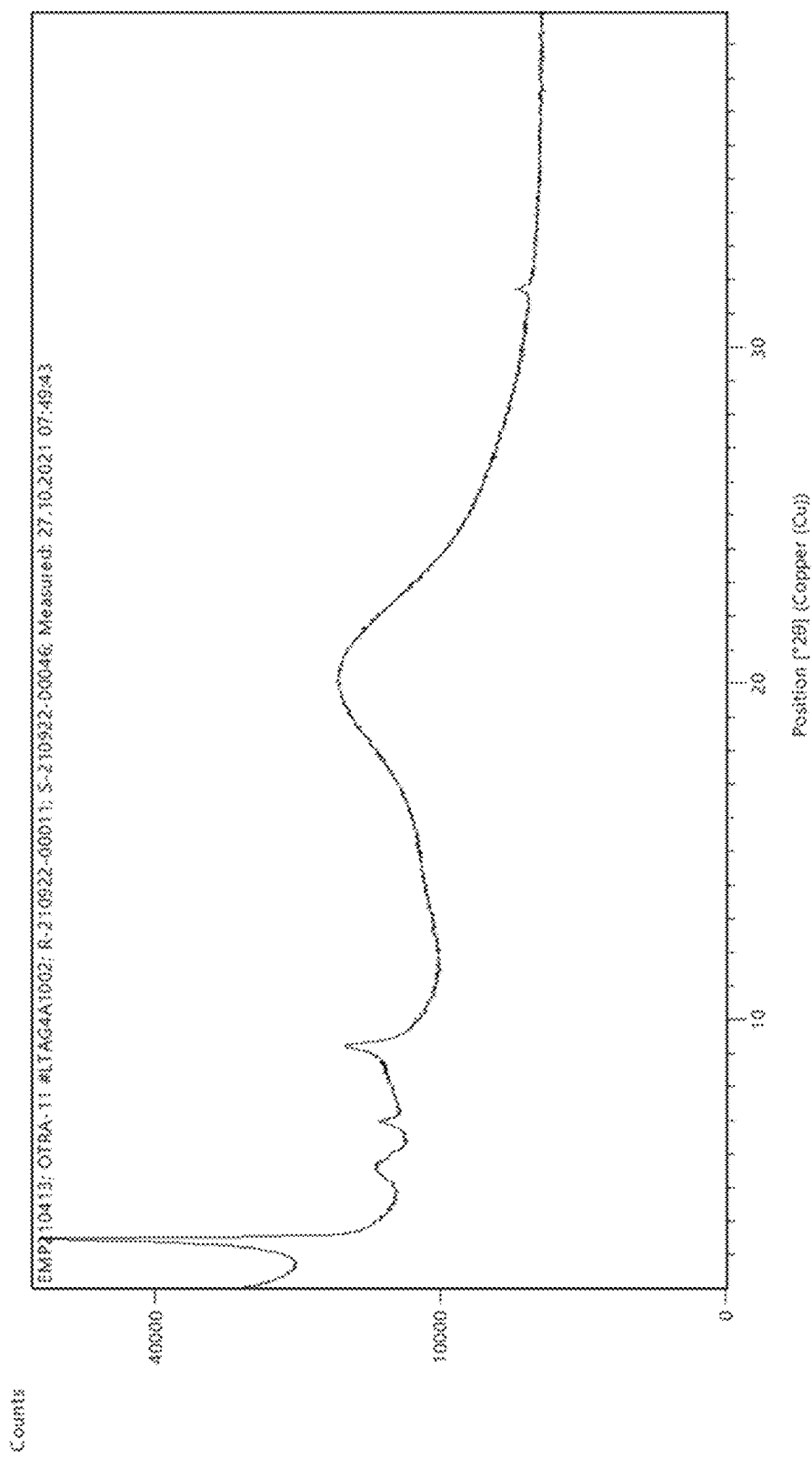
FIG. 2 is an x-ray powder diffraction pattern of amorphous obicetrapib hemicalcium.
Figure 3:
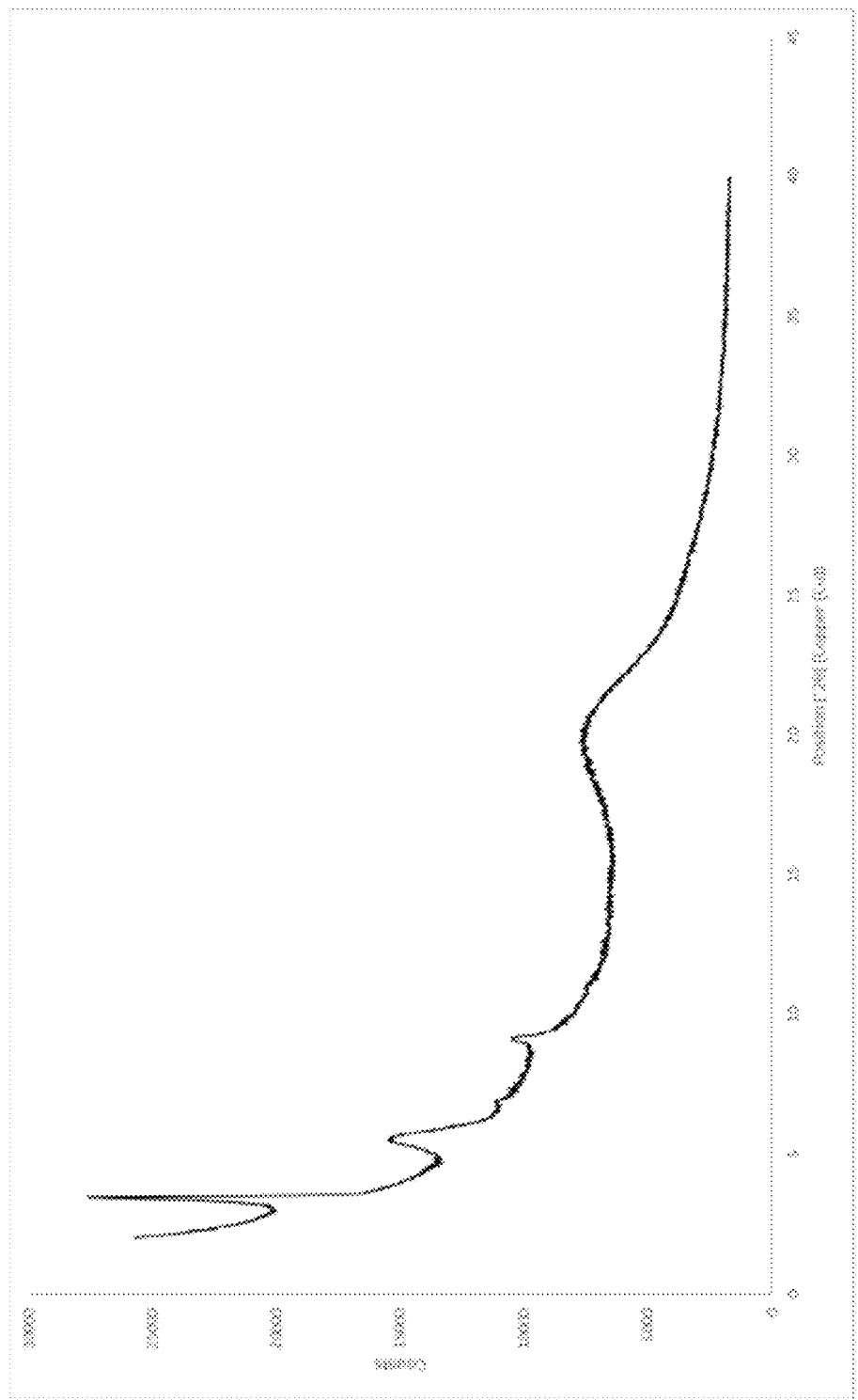
FIG. 3 is an x-ray powder diffraction pattern of amorphous obicetrapib hemicalcium.
Figure 6:
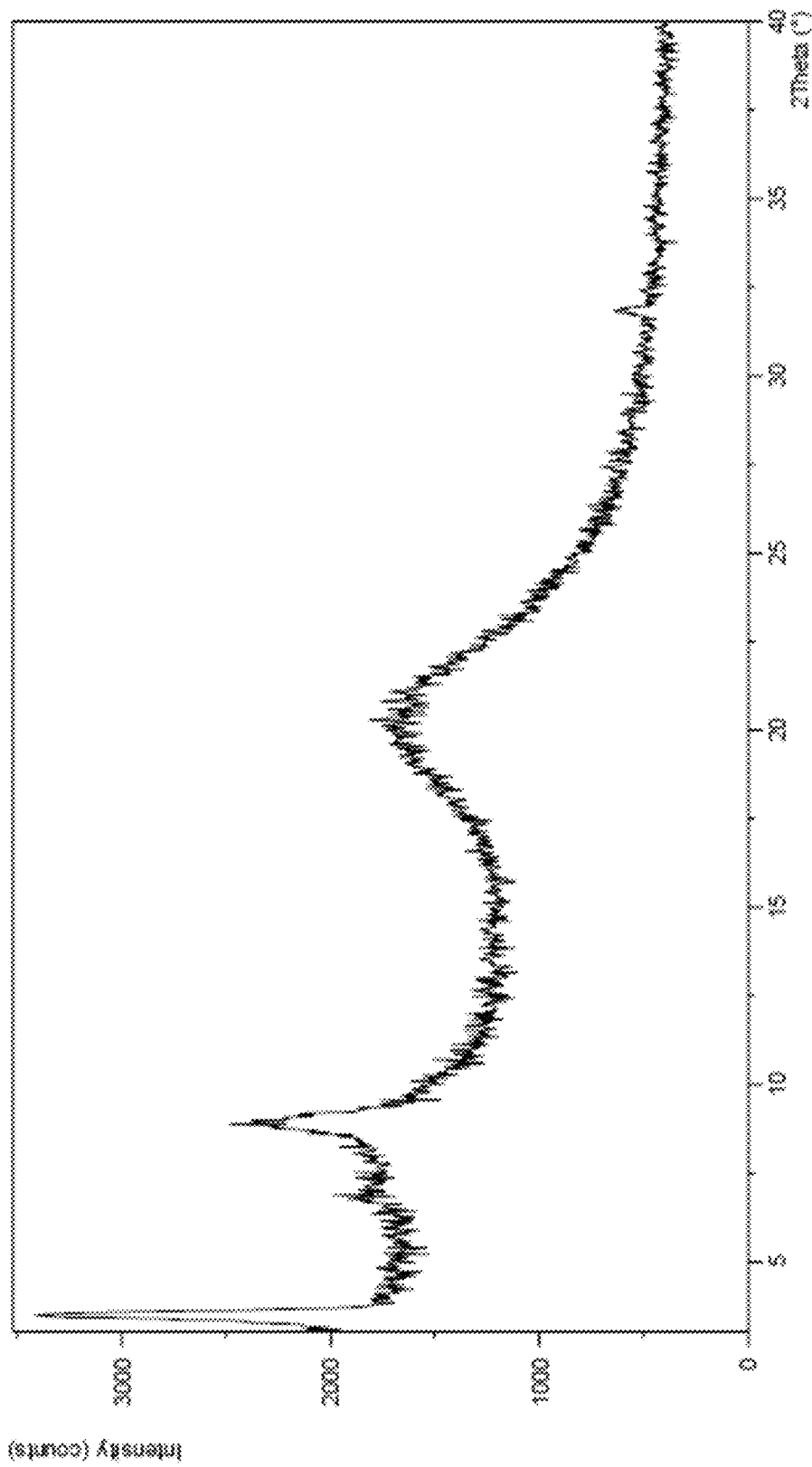
FIG. 6 is an x-ray powder diffraction pattern of crystalline obicetrapib hemicalcium.

The amorphous obicetrapib hemicalcium of the disclosure is different from and can be distinguished from the crystalline obicetrapib hemicalcium disclosed in U.S. Pat. No. 7,872,126. A common technique used to distinguish crystalline from amorphous materials is x-ray powder diffraction. However, this technique has limitations, especially when the crystalline material is disordered. In the case of amorphous obicetrapib hemicalcium, x-ray powder diffraction patterns of two different lots of amorphous obicetrapib hemicalcium are provided in FIG. 1 and FIG. 2. These patterns have the familiar "halo" type features that are associated with amorphous materials. The x-ray powder diffraction pattern from FIG. 2 has peaks at about 3.4° 2θ, about 7.0° 2θ, and about 9.2° 2θ. Similarly, another sample of FIG. 3 has x-ray powder diffraction peaks also at about 3.4° 2θ, about 7.0° 2θ, and about 9.2° 2θ. The x-ray powder diffraction patterns of any of FIG. 1 or FIG. 2 or FIG. 3 may be used to characterize amorphous obicetrapib hemicalcium, provided, however, occasionally, a sharp higher angle peak is present, such as at about 31.7° 2θ is found (such as in FIG. 2), and that peak, when present, is due to sodium chloride. In FIG. 3, in another sample of amorphous obicetrapib hemicalcium, peaks at about 3.4° 2θ, about 70020, and about 9.2° 2θ were identified. The peak at about 5.6° 2θ in FIG. 3 was determined to be due to Kapton foil, which was used in the measurement setup as explained in Example 20. The x-ray powder pattern of crystalline obicetrapib hemicalcium as prepared in Example 16 is shown in FIG. 6. It too exhibits halo-like behavior which, for a crystalline compound, may be indicative of disorder.

Example 18, Example 19, Example 20, Example 21, and Example 22 set forth various x-ray powder diffraction procedures. The procedure of Example 18 was generally used to collect the data set forth in FIGS. 1, 6, 7, and 8; Example 19 was generally used for FIG. 2; Example 20 was used generally used for FIG. 3; Example 21 generally used for FIGS. 18, 19, and 20 (with FIG. 20 being for Compound 1D rather than crystalline obicetrapib HCl); and Example 22 was generally used for FIGS. 22-25 and FIG. 28.

The use of the term "amorphous" in the "amorphous obicetrapib hemicalcium" does not mean that the material has no order whatsoever. As shown by the presence of peaks in the x-ray powder diffraction pattern, there is still some order in the sample. Thus, as used herein, the term "amorphous" in "amorphous obicetrapib hemicalcium" does not mean that the x-ray powder diffraction pattern must contain purely an amorphous halo (but may contain halo-like features). Rather, it means that there is disorder, but the amorphous phase is distinguishable from the crystalline phase as discussed below.

Another technique which may be used to distinguish crystalline materials from amorphous materials is polarized light microscopy ("PLM"). In PLM, a material is viewed through polarized light, and by viewing the material through cross-polarizers, one can differentiate between materials that are anisotropic (e.g., crystals) or isotropic (e.g., amorphous compounds). Anisotropic materials, when exposed to polarized light through cross polarizers, exhibit birefringence which manifests itself by exhibiting color change through cross polarizers. Isotropic materials, on the other hand, do not show birefringence and exhibit no color change when exposed to polarized light.

Figure 9:
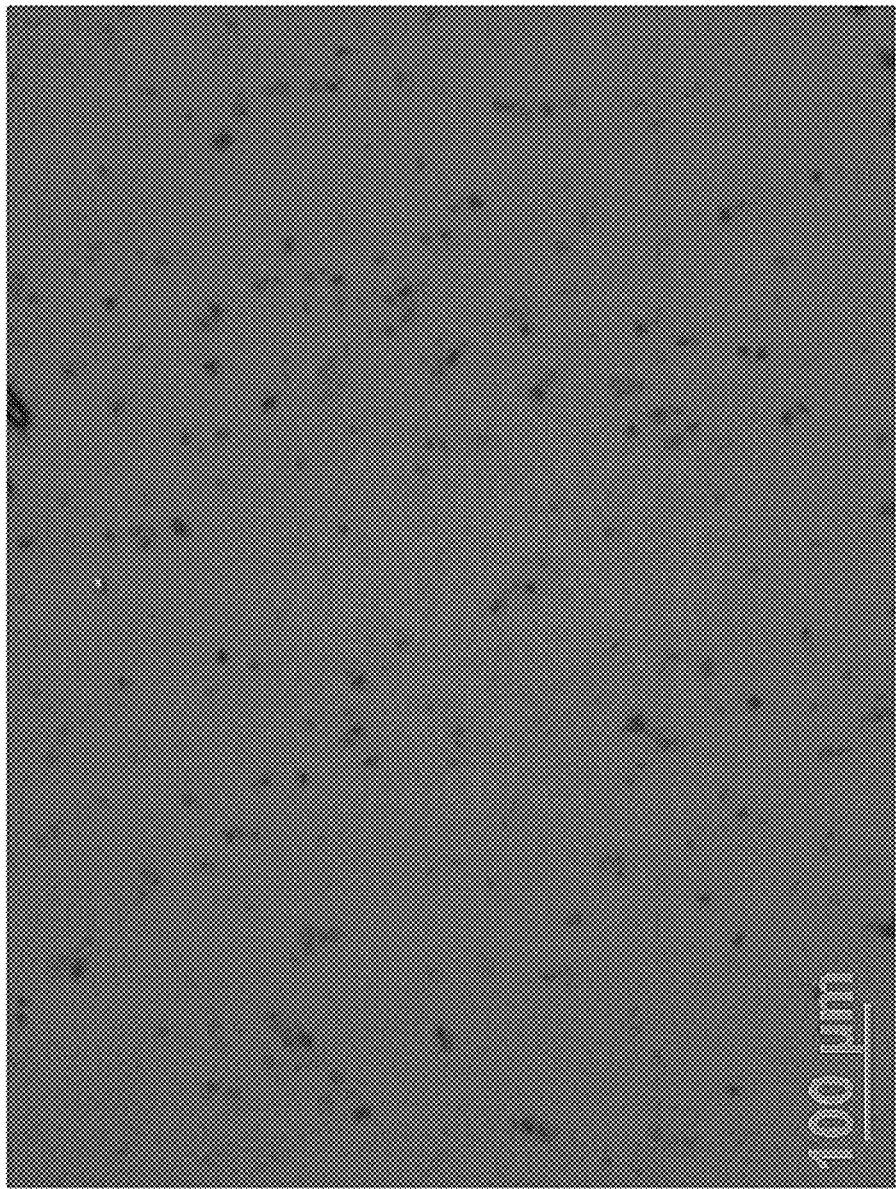
FIG. 9 is a polarized light micrograph of amorphous obicetrapib hemicalcium.
Figure 10:
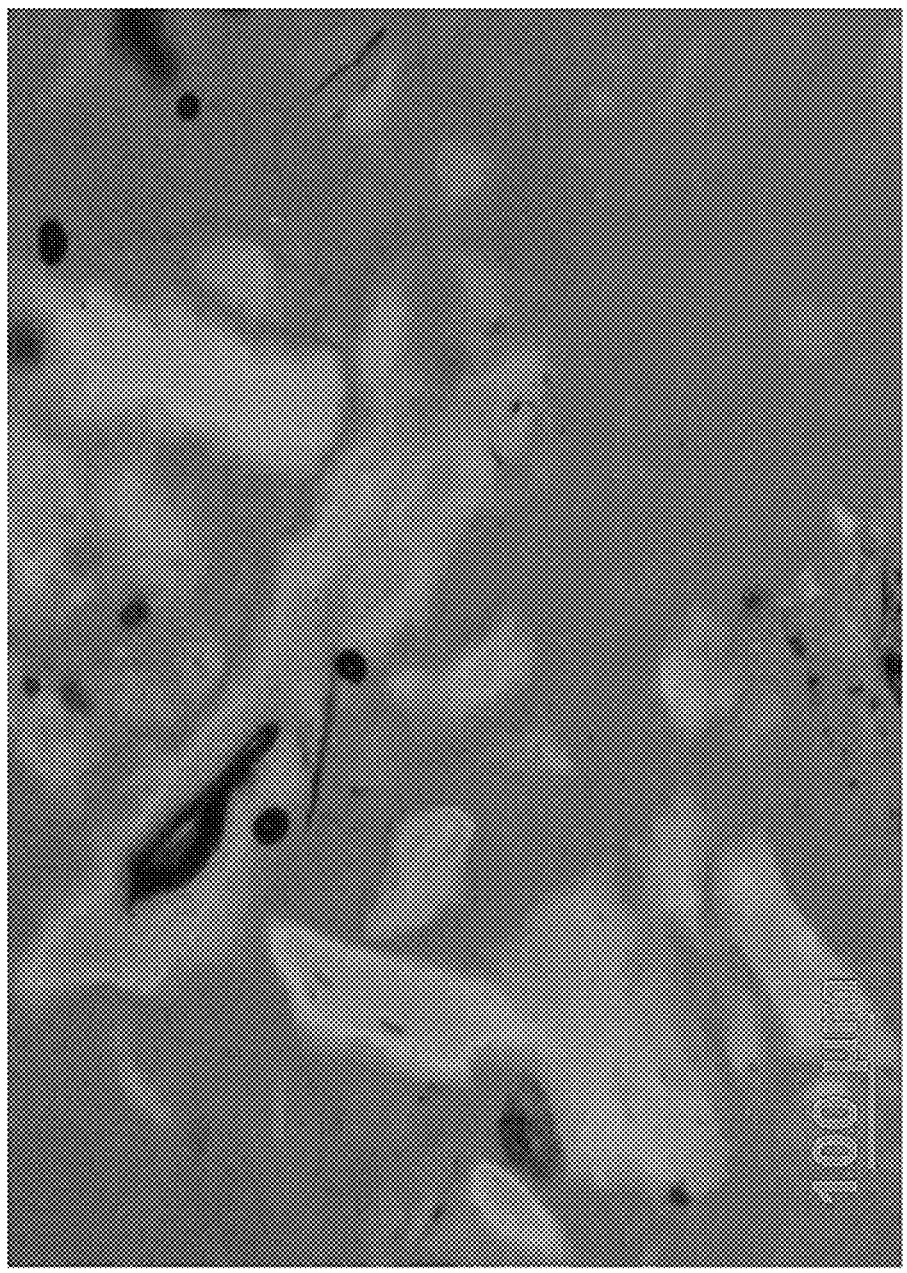
FIG. 10 is a polarized light micrograph of crystalline obicetrapib hemicalcium.

In FIG. 9, amorphous obicetrapib hemicalcium was analyzed by polarized light microscopy as set forth in Example 17. As FIG. 9 shows, the materials under study do not birefringe indicating that the material is amorphous. By comparison, FIG. 10 is a polarized light micrograph of crystalline obicetrapib hemicalcium made in accordance with Example 16. Notably, the particles shown in FIG. 10 (which is in black and white) exhibits a much brighter contrast. In the corresponding color version, that figure is multicolored. Thus, FIG. 10 indicates crystallinity. In addition, the crystals in FIG. 10 are larger than the particles provided in the amorphous obicetrapib hemicalcium polarized light micrograph of FIG. 9. Accordingly, PLM and/or the lack of birefringence can be used to characterize amorphous obicetrapib hemicalcium.

Figure 12:
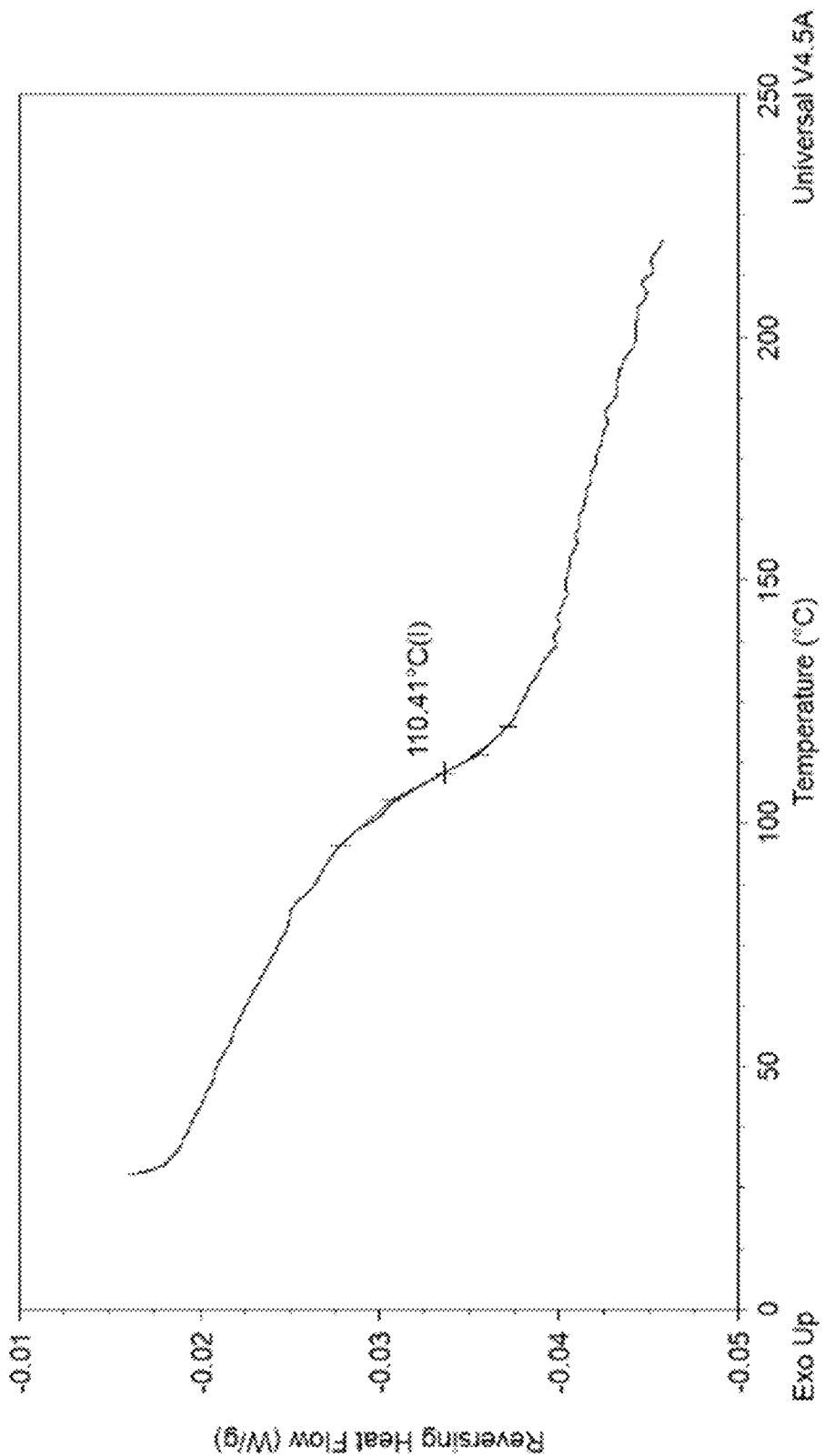
FIG. 12 is a modulated differential scanning calorimetry thermogram (with pinhole) of amorphous obicetrapib hemicalcium.

Other techniques can further be used to distinguish amorphous obicetrapib hemicalcium from crystalline obicetrapib hemicalcium, and therefore can be used to characterize amorphous obicetrapib hemicalcium. One such technique is modulated differential scanning calorimetry also referred to as "mDSC." The difference in the amount of heat necessary to increase the temperature of a sample, as compared to a reference, is measured as a function of temperature and may be measured using modulated Differential Scanning Calorimetry (mDSC). In an mDSC thermogram, one can also measure a glass transition temperature which can be used to characterize an amorphous material. In FIG. 12, for which the procedure is described in Example 25, the mDSC thermogram of amorphous obicetrapib hemicalcium was measured using an open sample holder allowing for volatile gases to escape during a measurement. In FIG. 12, the opening was done by piercing a lid on the pan so as to create a pinhole. A glass transition temperature of about 110° C. was recorded for this sample.

Figure 13:
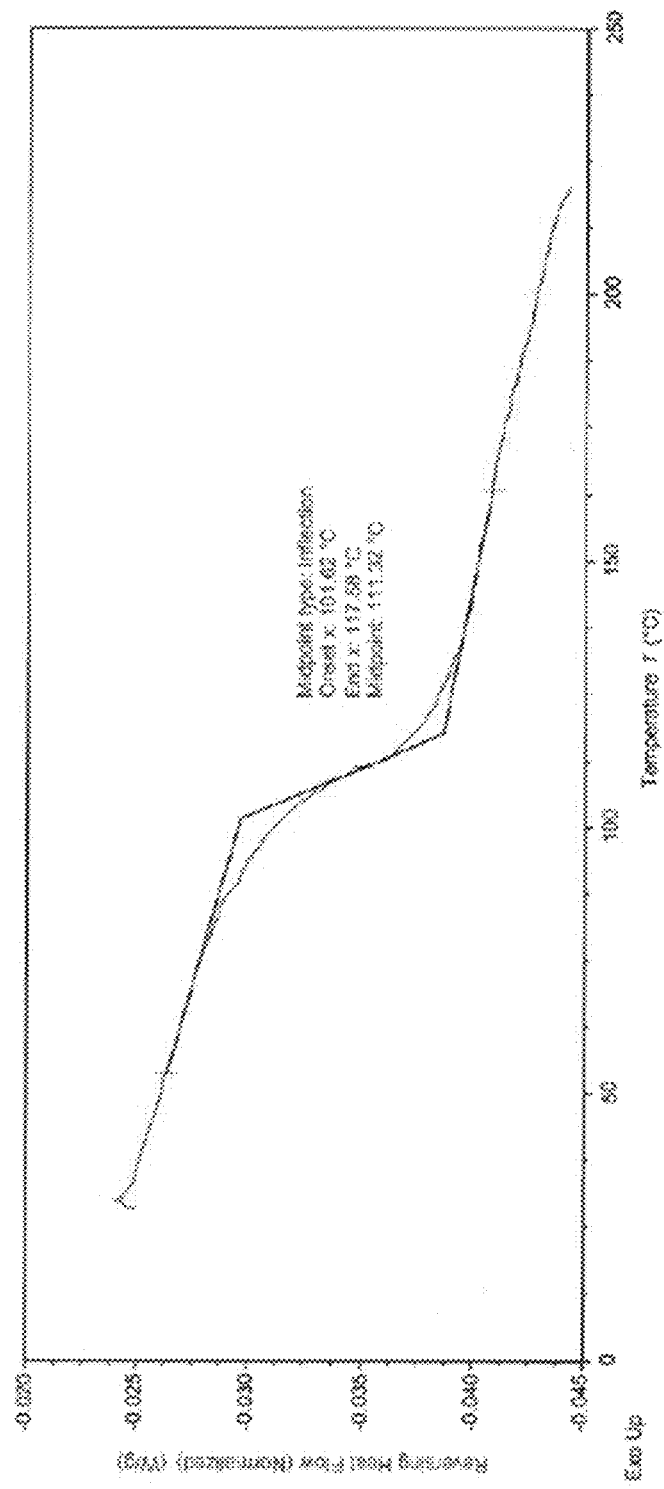
FIG. 13 a modulated differential scanning calorimetry thermogram (with pinhole) of amorphous obicetrapib hemicalcium.

With respect to thermal measurements, the term "about" generally refers to a variability of plus or minus 1° C. By comparison, crystalline obicetrapib hemicalcium has a higher glass transition temperature under the same conditions, and three measurements in FIG. 14 indicate a range between about 118° C. and about 125.5° C. In some embodiments, the glass transition temperature of amorphous obicetrapib hemicalcium is between about 109° C. and 112° C. when measured with a pinhole. In one sample, at Example 26, the glass transition temperature of amorphous obicetrapib hemicalcium was found to be about 111° C. (111.32° C. at the midpoint) and is shown in FIG. 13. The onset was measured to be about 102° C. (101.62° C.) and the endpoint about 118° C. (117.58° C.)

The glass transition temperature of amorphous obicetrapib hemicalcium may also be measured using mDSC with a closed pan. The type of sample preparation may affect the measured glass transition temperature. In such cases, the glass transition temperature decreases to temperatures of less than about 100° C. and in particular between about 70° C. and about 92° C. depending on humidity.

Figure 11:
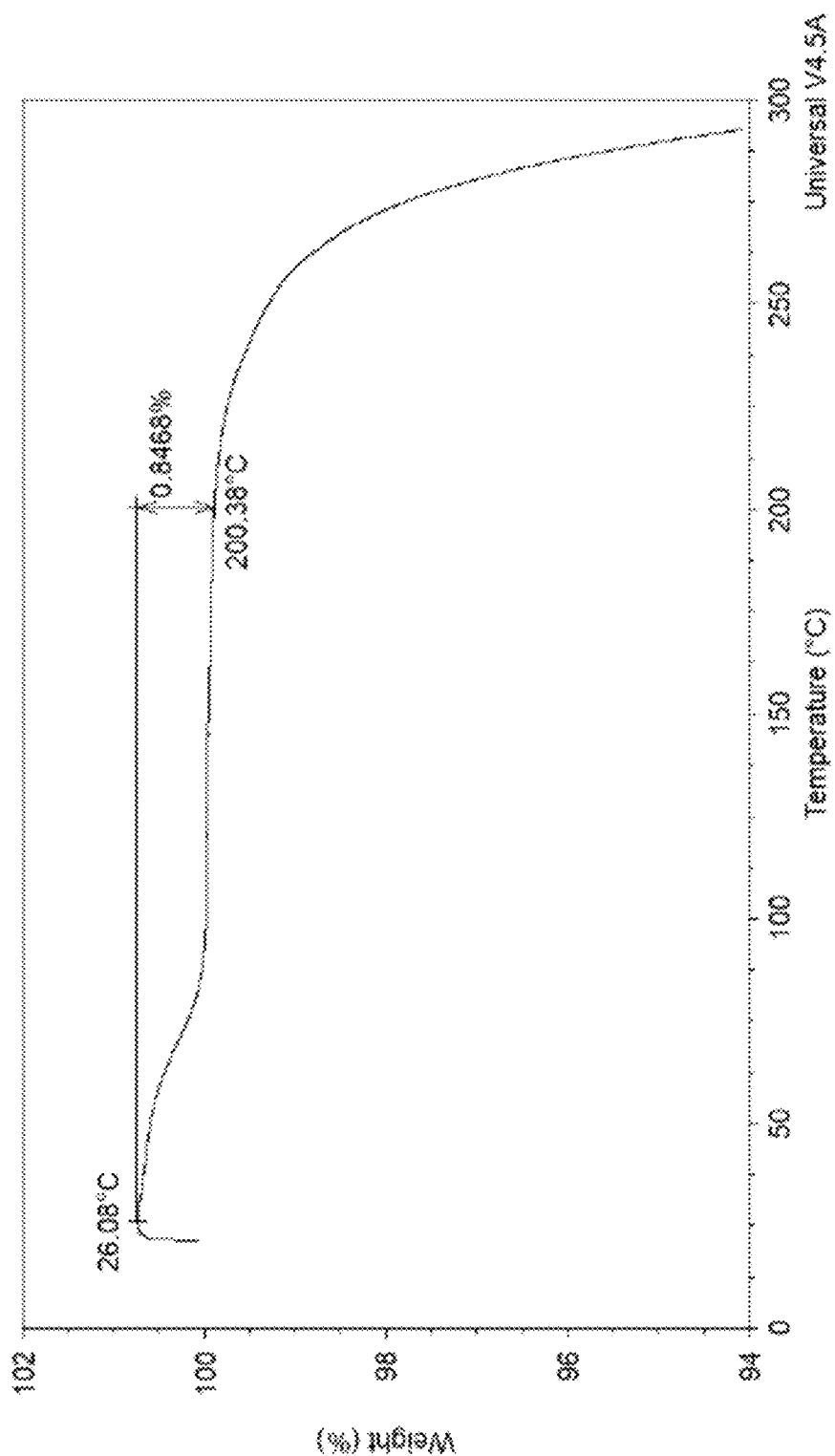
FIG. 11 is a thermogravimetric analysis plot of amorphous obicetrapib hemicalcium.

Other thermal techniques may also be used to analyze and characterize amorphous obicetrapib hemicalcium such as thermogravimetric analysis (TGA). FIG. 11 is a thermogravimetric analysis thermogram of amorphous obicetrapib hemicalcium showing a weight loss of less than 1% when heated to about 200° C. Such weight losses may be, for example, between about 0.8% and about 0.95% including between about 0.84% and about 0.92%. In FIG. 11, the weight loss was determined to be about 0.85%. This particular material was found to have a water content of about 1.5%. In some embodiments, the water content of may be higher and include a range from about 0% to about 5% water by weight, including up to about 4% by weight, up to about 3% by weight, and between about 0.5% and 1.5% by weight.

Figure 15:
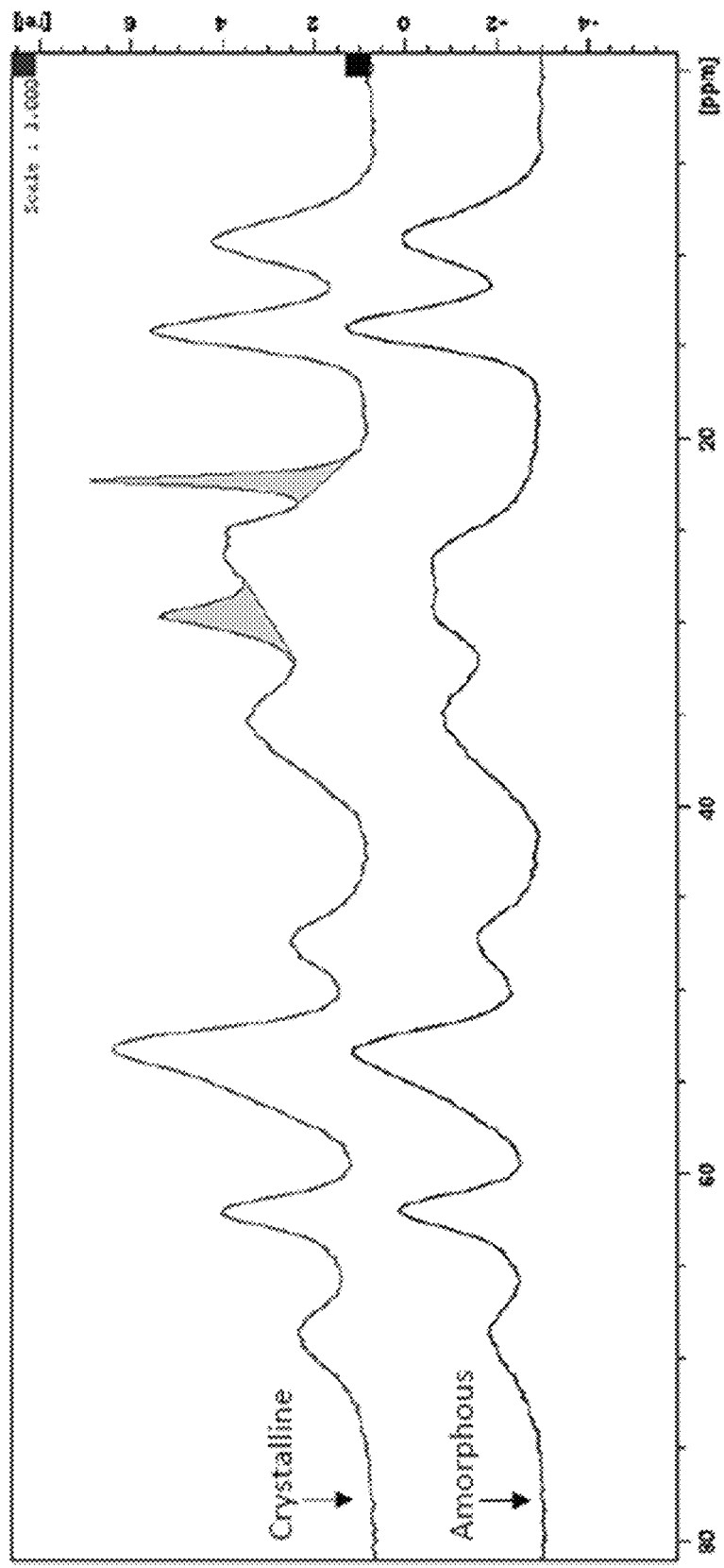
FIG. 15 is a solid-state $^{13}$C-NMR spectrum of amorphous and crystalline obicetrapib hemicalcium.
Figure 16:
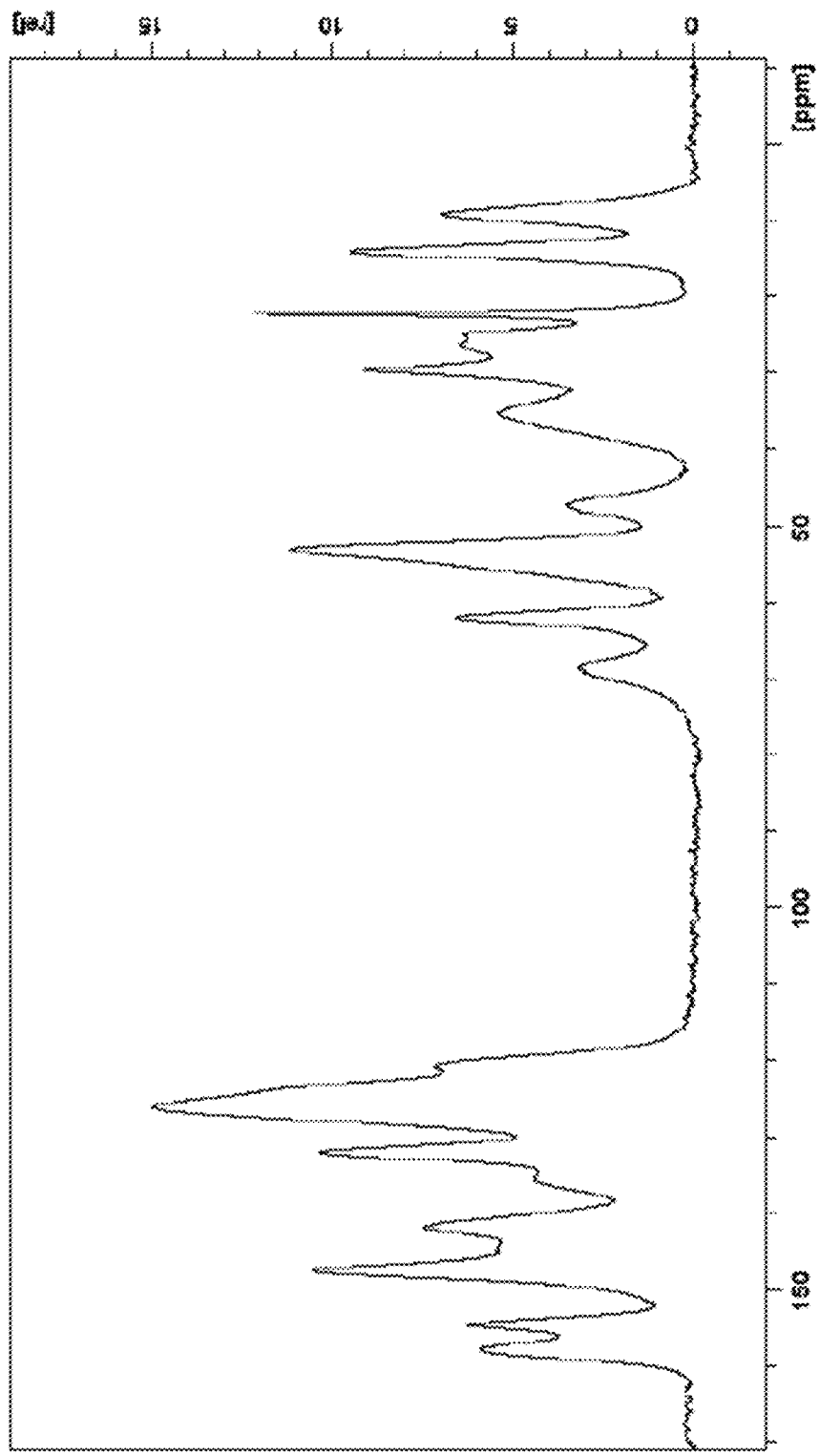
FIG. 16 is a solid-state $^{13}$C-NMR spectrum of crystalline obicetrapib hemicalcium.
Figure 17:
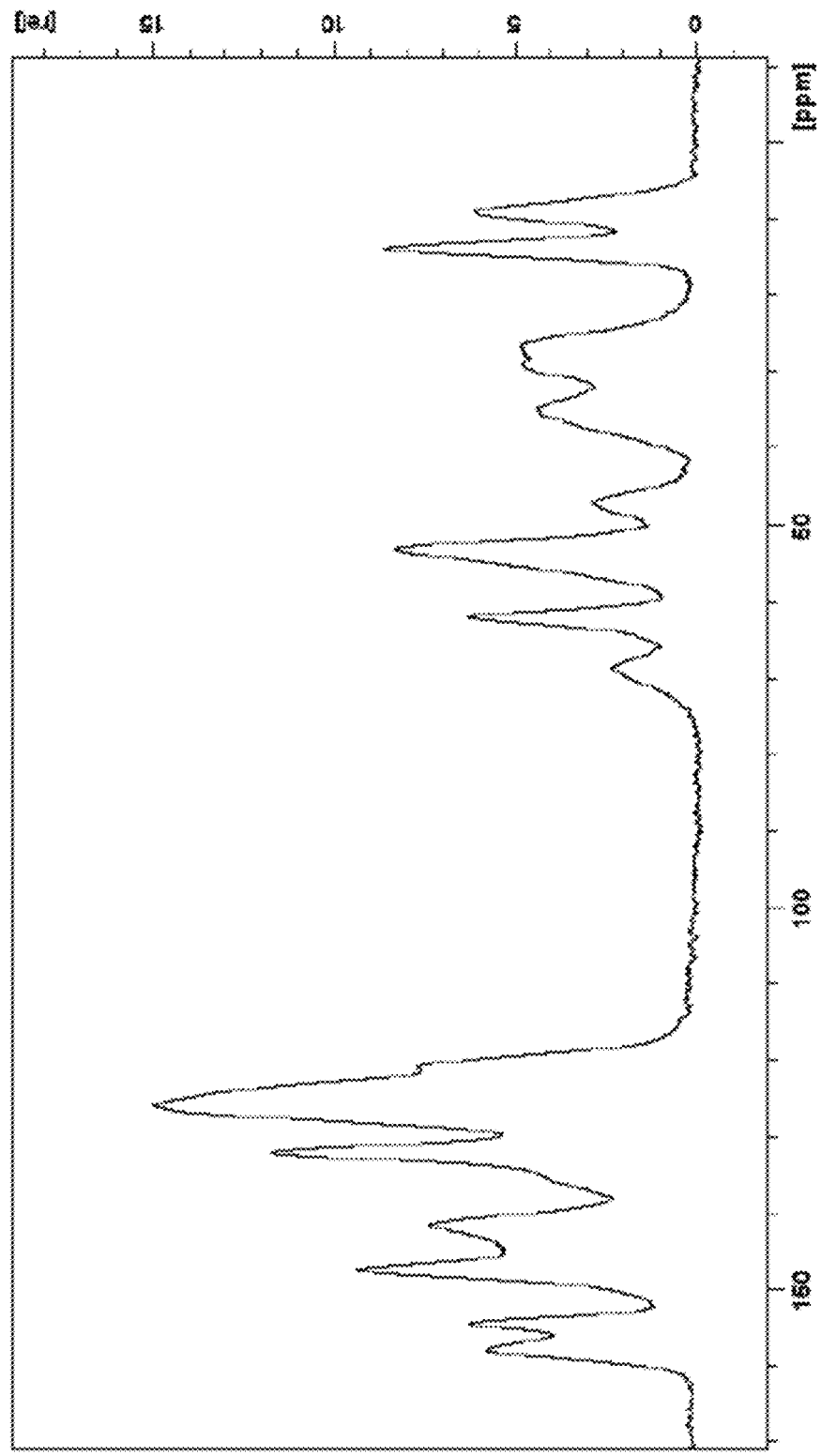
FIG. 17 is a solid-state $^{13}$C-NMR spectrum of amorphous obicetrapib hemicalcium.

Solid-state $^{13}$C-NMR spectroscopy is another technique which may be used to characterize amorphous materials. FIG. 15 shows a solid-state $^{13}$C-NMR spectrum of both crystalline and amorphous obicetrapib hemicalcium with FIG. 16 and FIG. 17 showing the crystalline and amorphous obicetrapib hemicalcium separately. There are at least two differences in the spectra. The crystalline phase has a peak at about 22.1 ppm and which not present in the amorphous phase. In addition, a peak at about 29.5 ppm in the crystalline phase is pronounced while not nearly so in the amorphous phase. Thus, the absence of a solid-state $^{13}$C-NMR peak at about 22.1 ppm and/or the absence of a pronounced peak at about 29.5 ppm may be used to characterize amorphous obicetrapib hemicalcium. In addition, a solid-state $^{13}$C-NMR spectrum substantially the same as that of FIG. 17 may be used to characterize amorphous obicetrapib hemicalcium. The absence of a peak in this context does not mean there is necessarily no intensity of, for example, 22.1 ppm or 29.5 ppm, but rather the intensity is not pronounced as it is in the crystalline obicetrapib hemicalcium $^{13}$C-NMR spectrum.

The properties of crystalline materials also typically differ from those of amorphous materials. Thermodynamically, crystalline materials are more physically stable than amorphous materials. Accordingly, there is a thermodynamic driving force to convert amorphous compounds into crystalline ones. Under accelerated stress conditions, if there would be a physical conversion of solid form, one would therefore generally expect it to be from amorphous to crystalline. However, with obicetrapib hemicalcium, the reverse is the case.

Figure 7:
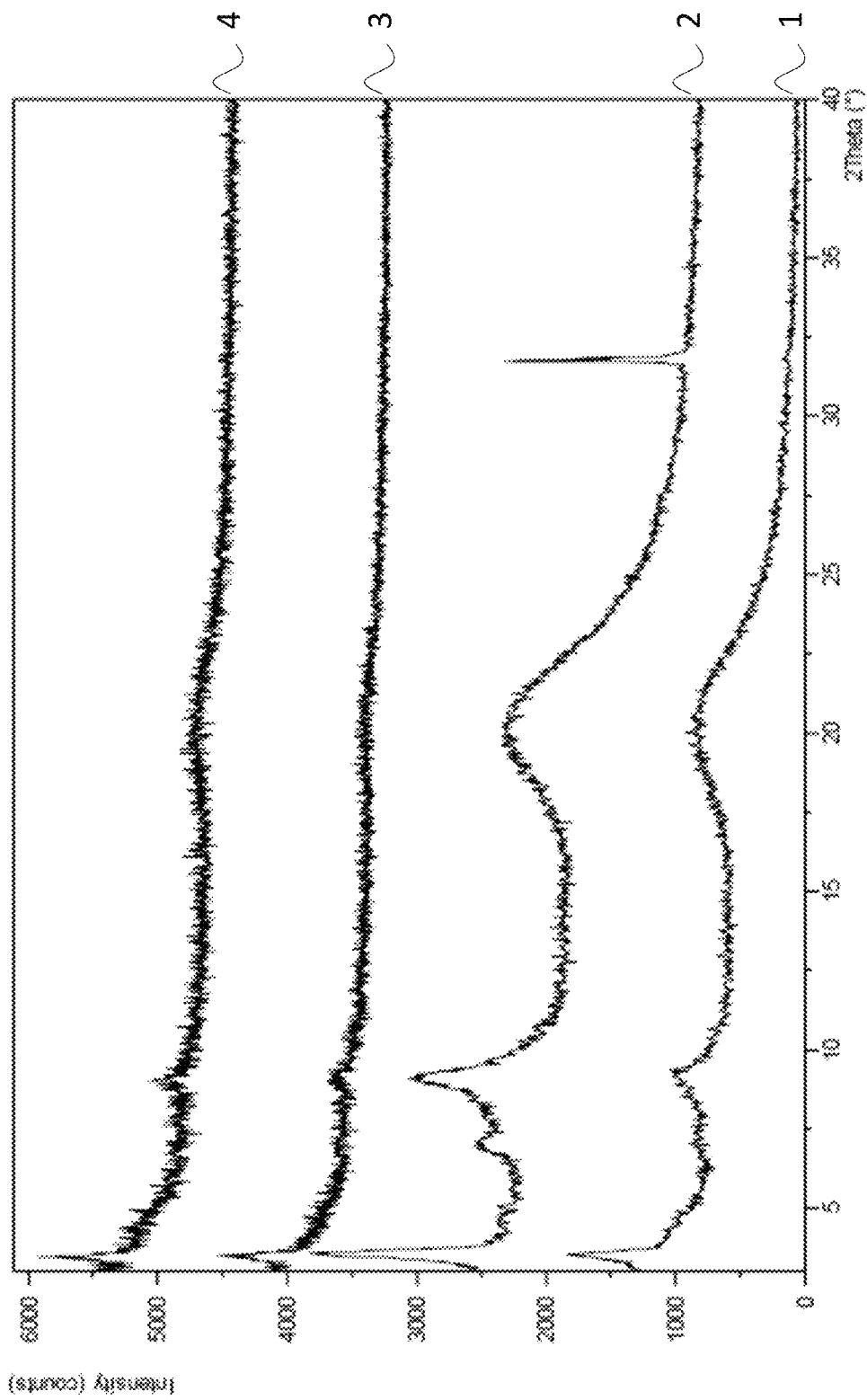
FIG. 7 is an x-ray powder diffraction pattern stackplot from a stability study of crystalline obicetrapib hemicalcium.
Figure 8:
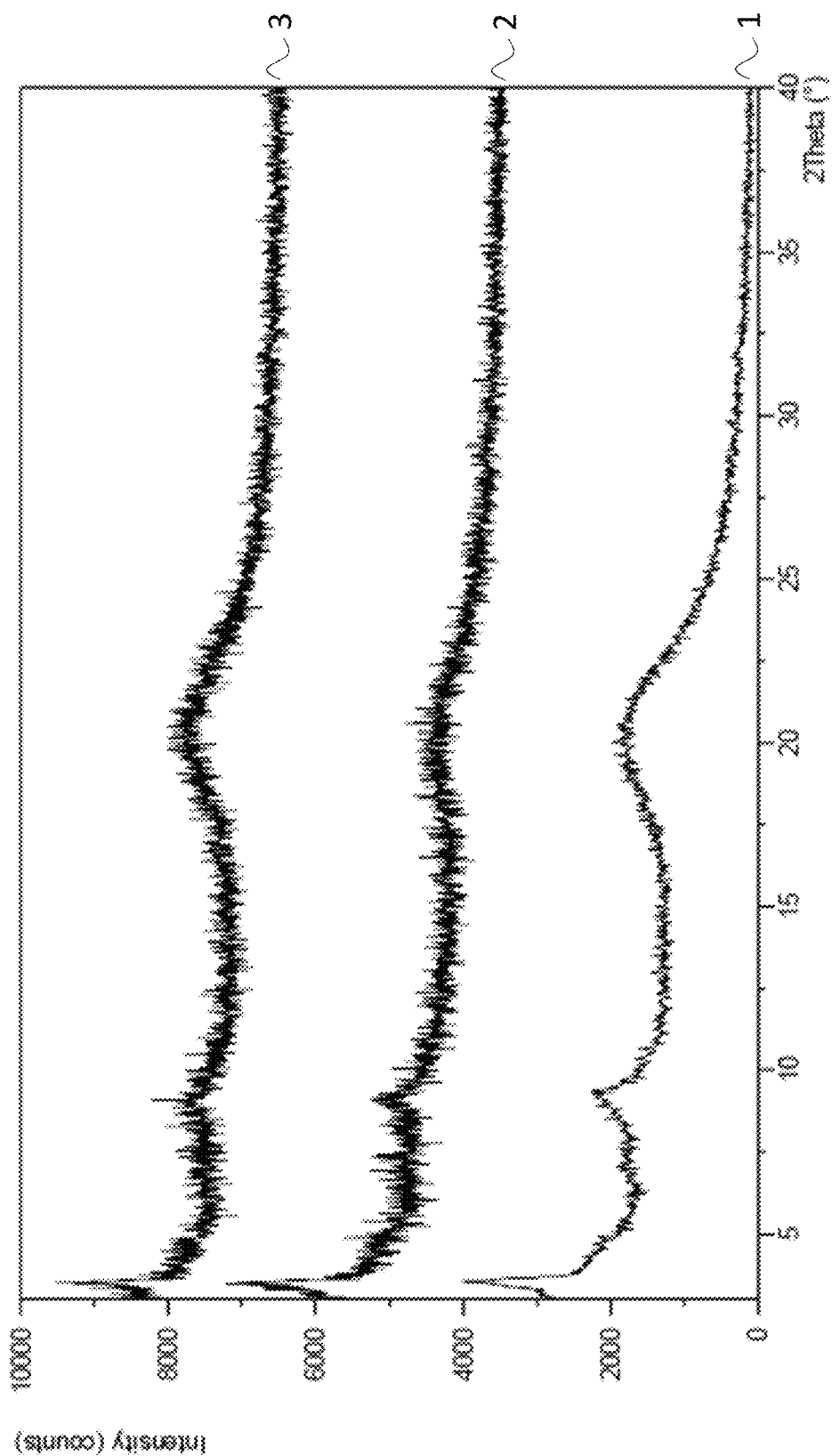
FIG. 8 is an x-ray powder diffraction pattern stackplot from a stability study of amorphous obicetrapib hemicalcium.

FIG. 6 is a plot of x-ray powder diffraction pattern taken of crystalline obicetrapib hemicalcium, and FIG. 7 is a plot of x-ray powder diffraction patterns taken of crystalline obicetrapib hemicalcium under stress conditions. In FIG. 7, there are four diffraction patterns shown based on stability study set forth in Example 27. Pattern 1 is an x-ray powder diffraction pattern of a sample of amorphous obicetrapib hemicalcium. Pattern 2 is the x-ray powder diffraction pattern of a sample of crystalline obicetrapib hemicalcium. In pattern 3, the sample of crystalline obicetrapib hemicalcium was exposed to 70° C. at 75% relative humidity for one day. As can be seen from pattern 3, the x-ray powder diffraction pattern shows the near total loss of crystallinity in that day. After 7 days under the same conditions, the result remains the same as seen in pattern 4. A similar experiment was performed on amorphous obicetrapib hemicalcium shown in FIG. 8. Pattern 1 was taken before the sample was placed on stability. Exposing that material to the same 70° C. and 75% relative humidity conditions did not trigger a crystallization and the material remained amorphous after 7 days (pattern 2) and 14 days (pattern 3). Thus, these experiments suggest, contrary to what one would expect, that the amorphous form of obicetrapib hemicalcium is more stable than crystalline obicetrapib hemicalcium.

In some embodiments of the disclosure, provided herein is stable amorphous obicetrapib hemicalcium. In these embodiments, the amorphous obicetrapib hemicalcium is more physically stable than crystalline obicetrapib hemicalcium under typical pharmaceutical use and processing conditions.

While not wishing to be bound by theory, it is possible that the kinetics here are such that the amorphous phase is kinetically stabilized with respect to the thermodynamically more stable crystalline phase at least under pharmaceutically relevant processing and use conditions. The result of this stability profile is that amorphous obicetrapib hemicalcium is more suitable for pharmaceutical development and use than the corresponding crystalline phases. Despite being more physically resilient, amorphous obicetrapib hemicalcium is more soluble than the highly insoluble crystalline obicetrapib hemicalcium.

Solubility is especially challenging with obicetrapib. At 20° C., for example, the solubility of obicetrapib has been measured to be substantially less than 0.1 mg/mL in water. It would be desirable to have a solid form of obicetrapib that would deliver a larger amount of obicetrapib.

While solubility is a thermodynamic quantity of a material, one can measure the kinetic solubility of a material without necessarily reaching thermodynamic equilibrium. Such measurements provide the solubility under metastable conditions and provide information, for example, of the amount of material undergoing dissolution as a function of time.

The amorphous form has a higher kinetic solubility and dissolution rate than the crystalline form (and by extension obicetrapib itself). Both crystalline and amorphous obicetrapib hemicalcium kinetic solubility determinations were made in biorelevant media at different pHs, namely at about 5.0 (FeSSIF conditions) and at pH of about 6.5 (FaSSIF) conditions as set forth in Example 28.

Table 1 shows the measured solubility of two different batches of amorphous obicetrapib hemicalcium versus crystalline obicetrapib hemicalcium over the course of 2 hours in FeSSIF media at 37° C. In both cases, the amorphous obicetrapib hemicalcium had a higher concentration in solution than the corresponding crystalline material for all time points measured. The concentrations in Table 1 are those of obicetrapib (i.e., the free acid).

TABLE 1

Kinetic Solubility of Crystalline and Amorphous Obicetrapib Hemicalcium in FeSSIF (pH 5.0) at 37° C.

| | Concentration in Solution (mg/ml) | | | | |
|---|---|---|---|---|---|
| | 15 mins | 30 mins | 60 mins | 90 mins | 120 mins |
| Amorphous obicetrapib hemicalcium Batch #1 | 0.520 | 0.661 | 0.675 | 0.696 | 0.675 |
| Amorphous obicetrapib hemicalcium Batch #2 | 0.502 | 0.618 | 0.628 | 0.658 | 0.642 |
| Crystalline obicetrapib hemicalcium | 0.085 | 0.169 | 0.369 | 0.453 | 0.529 |

Table 2 shows a similar experiment at 37° C. but in FaSSIF media at a pH of 6.5. As with Table 1, in both batches, the amorphous obicetrapib hemicalcium had a higher concentration in solution than the corresponding crystalline material for all time points measured. The concentrations in Table 2 are those of obicetrapib (i.e., the free acid).

TABLE 2

Kinetic Solubility of Crystalline and Amorphous Obicetrapib Hemicalcium in FaSSIF (pH 6.5) at 37° C.

| | Concentration in Solution (mg/ml) | | | | |
|---|---|---|---|---|---|
| | 15 mins | 30 mins | 60 mins | 90 mins | 120 mins |
| Amorphous obicetrapib hemicalcium Batch #1 | 0.060 | 0.099 | 0.163 | 0.201 | 0.244 |
| Amorphous obicetrapib hemicalcium Batch #2 | 0.090 | 0.14 | 0.229 | 0.293 | 0.387 |
| Crystalline obicetrapib hemicalcium | 0.030 | 0.048 | 0.084 | 0.107 | 0.144 |

Because amorphous obicetrapib hemicalcium dissolves faster than the corresponding crystalline phase, more drug is available for immediate use and potentially higher bioavailability in the amorphous phase than in the crystalline phase.

Amorphous obicetrapib hemicalcium is also advantageous because, unlike many amorphous organic compounds, it does not readily pick up moisture. When exposed to relative humidities approaching 90%, moisture uptake has been measured to be typically less than about 5% for example. This lack of hygroscopicity is favorable because it does not require any special handling or storage conditions. Other drawbacks commonly associated with manufacturing and using amorphous materials are similarly not present. For example, amorphous materials are often challenging to make chemically pure. Here, however, amorphous obicetrapib hemicalcium can be made routinely with chemical purities of 99.9% or higher.

In some embodiments of the disclosure, there is provided substantially pure amorphous obicetrapib hemicalcium. In these and other embodiments, the chemical purity of substantially pure amorphous obicetrapib hemicalcium is 99.9% or greater.

In many aspects of the disclosure, there is provided a method of preparing an amorphous calcium salt of obicetrapib, such as amorphous obicetrapib hemicalcium, wherein the method comprises: treating obicetrapib with an acid to form a salt, solvate, or composition; isolating the resulting salt, solvate or composition; and treating that salt, solvate, or composition with a calcium source to create an amorphous obicetrapib calcium salt, such as amorphous obicetrapib hemicalcium. The resulting salt can then be isolated.

Examples of calcium sources include calcium salts such as halogenated calcium salts and soluble calcium salts. In many embodiments, the calcium source is calcium chloride.

The preparation of an amorphous salt of obicetrapib calcium such as amorphous obicetrapib hemicalcium has been found to occur when there is an intermediate salt, solvate or composition (such composition comprising the corresponding acid used to make a salt). Treating obicetrapib directly with a calcium base such as calcium hydroxide has not been found to be a viable way of making an amorphous salt of obicetrapib calcium due to either low solubility, the weakness of the bases available or both. Rather, it has been found that by deploying an intermediate salt, such as a sodium salt, the preparation of amorphous obicetrapib hemicalcium is viable. However, even with a sodium salt, it is preferable for purity and yield purposes to utilize an additional salt or salt-type exchange (such as with the use of a composition or solvate rather than an actual salt) in connection with the sodium salt of obicetrapib. In particular, the use of the salt, solvate, or composition enables the production of a highly pure amorphous calcium salt of obicetrapib such as amorphous obicetrapib hemicalcium.

Exemplary salts that may be made as an intermediate include those from a sulfonate (e.g., besylate, tosylate, napsylate, camsylate, esylate, edisylate, or mesylate), a sulfate (e.g., methylsulfate), a halogen (e.g., chloride, iodide, or bromide), acetate, aspartate, benzoate, bicarbonate, bitartrate, carbonate, citrate, decanoate, fumarate, gluceptate, gluconate, glutamate, glycolate, hexanoate, hydroxynaphthoate, isethionate, lactate, lactobionate, malate, maleate, mandelate, mucate, nitrate, octanoate, oleate, pamoate, pantothenate, phosphate, polygalacturonate, propionate, salicylate, stearate, succinate, tartrate, or a teoclate. When the intermediate is a solvate or a composition, then the corresponding acids may be used or present. In addition, when a solvate, the intermediate may further include a solvent such as an organic solvent or water, in which case the solvate would be a hydrate. One such organic solvent is CPME (cyclopentyl methyl ether).

In some embodiments, the intermediate is a solvate of an acid. In these and other embodiments, the intermediate is a solvate of an acid and an organic solvent. In some particular embodiments, the intermediate is a solvate comprising an acid and a solvent. In some of these embodiments, the acid is hydrochloric acid and a solvent is CPME.

In many aspects of the disclosure, the disclosure includes methods for preparing amorphous obicetrapib calcium salts, such as amorphous obicetrapib hemicalcium. The disclosure further includes amorphous obicetrapib calcium salts, including amorphous obicetrapib hemicalcium, so prepared. In one such preparation, an intermediate referred to herein as crystalline obicetrapib HCl is used in the processes for preparing amorphous obicetrapib calcium, such as amorphous obicetrapib hemicalcium.

In many aspects of the disclosure, amorphous obicetrapib hemicalcium is prepared via a chemical synthesis where an intermediate is used denoted by Formula (IH):

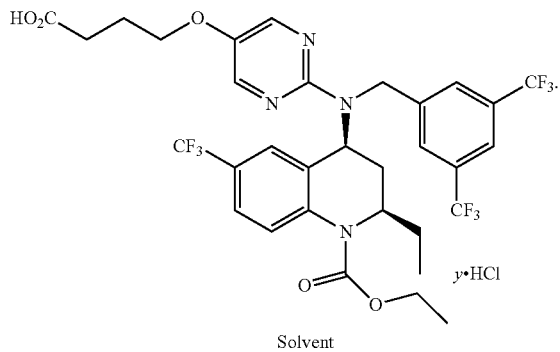

(IH)

Solvent

Where y varies such that the mass percent of HCl varies from 0.01% to 8% by weight and is believed to further include an associated organic solvent such as by way of a solvate. In some embodiments, y varies from 0.002 to 1.5. In some embodiments, y varies from 0.3 to 1. In some embodiments, y varies from 0.4 to 0.6, including between 0.5 and 0.6. In some embodiments, Formula (IH), as a solvate, is isolated in its crystalline form. In many embodiments, the solvent is CPME. Other solvents which may form solvates include toluene and heptane.

Obicetrapib HCl as typically prepared herein is crystalline. Further, the term crystalline obicetrapib HCl may include CPME as a solvate when CPME is used in the preparation of crystalline obicetrapib HCl. In Formula (IH), the solvate is of an organic solvent and in many embodiments, that solvent is CPME. In some embodiments, the disclosure provides for compositions comprising crystalline obicetrapib HCl.

Formula (IH) is referred to as obicetrapib HCl and when crystalline, it is referred to as crystalline obicetrapib HCl. A crystal structure of one solid form of crystalline obicetrapib HCl has been solved, and it is consistent with Form B crystalline obicetrapib HCl.

The crystal structure was solved in accordance with Example 34 and the single crystal prepared in accordance with Example 33. The structure is a complex multicomponent crystal showing six obicetrapib moieties, two of which are neutral, and four of which are charged in the asymmetric unit. There are four protonated obicetrapib molecules, each protonated at a nitrogen on the pyrimidine ring of obicetrapib, and four chloride ions. Two chloride ions each appear associated with two of the protonated nitrogens, confirming salt formation, but the other two chloride ions are coordinated to carboxyl moieties. The structure includes heptane and cyclopentyl methyl ether (CPME) solvent molecules. Void space with non-determinate contents is present with sufficient room for solvent and/or HCl but not obicetrapib. Without being bound by theory, it is believed that crystalline HCl obicetrapib is a mixed salt solvate. It has been found that when CPME is used to deliver HCl in the reaction to create Formula (IH), the chloride content of Formula (IH) ranges between about 2.5% and 3.0% by weight which is below what one would expect for a neutral salt—namely about 4.8% by weight.

Figure 18:
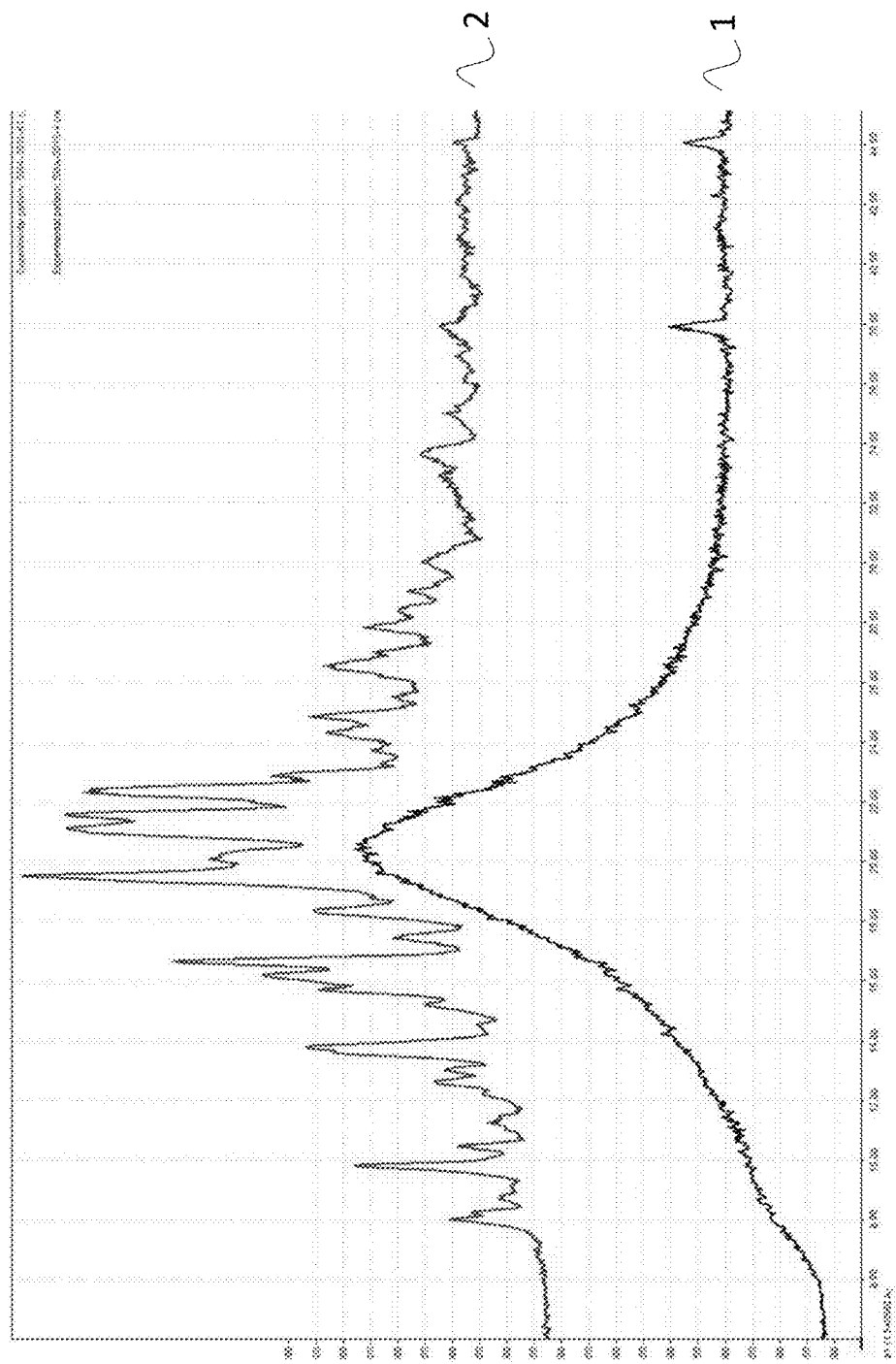
FIG. 18 is an x-ray powder diffraction pattern of crystalline obicetrapib HCl and at least partially desolvated crystalline obicetrapib HCl.

In many embodiments, when CPME is so used, it is found in the material when crystallized. When CPME is used in the reaction to deliver dry HCl and is thus found in the crystallized material, the resulting crystalline Formula (IH) material is referred to as crystalline obicetrapib HCl, those x-ray powder diffraction pattern are seen in FIG. 18. An advantage of using crystalline obicetrapib HCl as an intermediate is that the resulting amorphous obicetrapib hemicalcium has a chemical purity which is routinely 99.9% pure or greater. Chemical purity is the quantitative representation of whether other chemical entities other than the compound being measured are present. For example, a chemical purity of 99.9% amorphous obicetrapib hemicalcium means that not more than 0.1% of the compounds in a sample of amorphous obicetrapib hemicalcium are other entities. Physical purity refers to the amount of other solid forms of the same compound present which, in the case of amorphous obicetrapib hemicalcium, the other solid form being crystalline obicetrapib hemicalcium. The disclosure herein provides for amorphous obicetrapib hemicalcium which is physically pure meaning it is free or substantially free of crystalline obicetrapib hemicalcium. Unless otherwise stated herein, the purity measurements provided herein are measurements of chemical purity.

HCl obicetrapib, as used herein, is not limited to crystalline obicetrapib HCl. Indeed, upon desolvation, crystalline obicetrapib HCl may become amorphous.

Upon stress, crystalline obicetrapib HCl loses its crystallinity. In FIG. 18, pattern 2 reflects crystalline obicetrapib HCl subject to a mild drying treatment whereby surface solvent was removed and it can be seen that this compound is crystalline. By comparison, the sample whose x-ray powder diffraction was measured in pattern 1 was subject to a stronger drying treatment at 48 hours at 55° C. at a pressure of 2 mbar. As is apparent, this drying changed the material from crystalline to amorphous, likely due to loss of HCl and a desolvation of CPME. ¹H-NMR spectroscopy, for example, was used to show the presence of CPME in the top pattern, but was substantially absent in the lower, amorphous pattern. The amorphous pattern, therefore, represents HCl obicetrapib which is not crystalline obicetrapib. It may be obicetrapib, but is believed to have HCl associated with the obicetrapib as a solvate and thus is HCl obicetrapib, but with a lower chloride content than typically found in the ranges found for crystalline obicetrapib HCl. In some embodiments, that chloride content is less than 0.1% by weight such as between about 0.01% and 0.1% by weight.

Crystalline obicetrapib HCl may be characterized by an x-ray powder diffraction pattern comprising a peak at about 9.8° 2θ. In some embodiments, crystalline obicetrapib HCl may be characterized by an x-ray powder diffraction pattern comprising one or more peaks at about 8.1° 2θ, about 9.8° 2θ, about 13.8° 2θ, about 16.7° 2θ, or about 19.5° 2θ. Table 3 provides illustrative peaks which may be present in crystalline obicetrapib HCl. In some embodiments, crystalline obicetrapib HCl may be characterized by an x-ray powder diffraction pattern substantially the same as that in FIG. 19.

Figure 19:
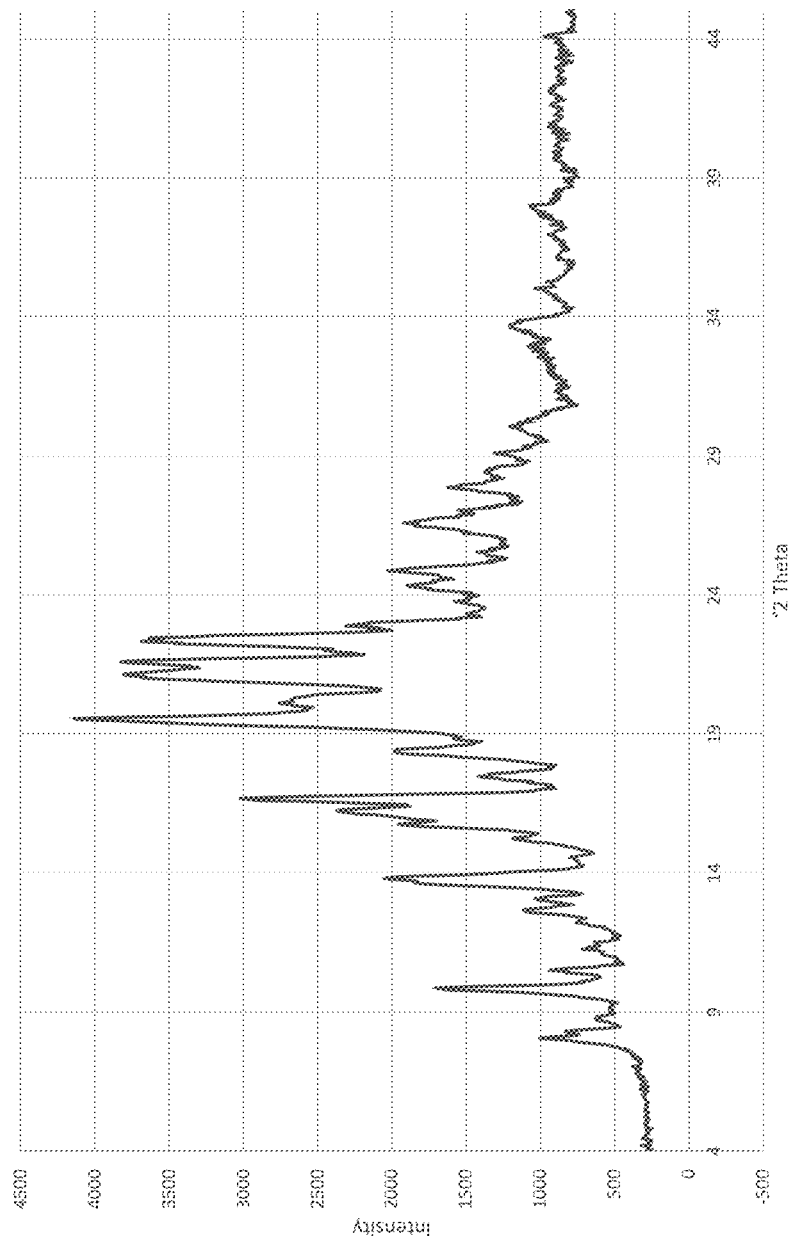
FIG. 19 is an x-ray powder diffraction pattern of crystalline obicetrapib HCl.

It is believed that the material analyzed in FIG. 19 was measured in such a way that a peak between about 4.3° 2θ and about 4.7° 2θ was not measured. Indeed, for each of Forms A, B, C, and D of crystalline obicetrapib hydrochloride, a peak is present and located between about 4.3° 2θ and about 4.7° 2θ. Therefore, crystalline obicetrapib hydrochloride may be characterized by an x-ray powder diffraction pattern comprising a peak between about 4.3° 2θ and about 4.7° 2θ.

TABLE 3

| °2θ | Intensity |
|---|---|
| 8.1 | 950 |
| 9.8 | 1650 |
| 13.8 | 2000 |
| 16.7 | 2900 |
| 19.5 | 4100 |
| 21.1 | 3700 |
| 21.6 | 3800 |
| 22.4 | 3600 |
| 24.9 | 1950 |
| 26.6 | 1850 |

Multiple forms of crystalline obicetrapib hydrochloride are disclosed herein. In some embodiments, Form A crystalline obicetrapib hydrochloride is provided. A preparation of Form A crystalline obicetrapib hydrochloride is set forth in Example 29. An x-ray powder diffraction pattern for Form A crystalline obicetrapib hydrochloride is provided in FIG. 22. Table 4 provides illustrative peaks which may be present in Form A crystalline obicetrapib hydrochloride.

TABLE 4

| °2θ | Intensity |
|---|---|
| 4.3000 | 5438.0000 |
| 6.5200 | 2916.0000 |
| 7.9400 | 5626.0000 |
| 8.2000 | 4379.0000 |
| 8.6000 | 3009.0000 |
| 9.0400 | 2537.0000 |
| 9.7200 | 7292.0000 |
| 10.0000 | 2700.0000 |
| 10.3800 | 3983.0000 |
| 11.3200 | 2248.0000 |
| 12.0800 | 2451.0000 |
| 12.5200 | 3571.0000 |
| 12.9200 | 3531.0000 |
| 13.4600 | 4711.0000 |
| 13.6400 | 6574.0000 |
| 13.8400 | 3989.0000 |
| 14.4200 | 2590.0000 |
| 15.1000 | 3693.0000 |
| 15.5600 | 4898.0000 |
| 16.1200 | 6431.0000 |
| 16.5000 | 9187.0000 |
| 17.3800 | 4591.0000 |
| 18.2000 | 7373.0000 |
| 18.5800 | 4447.0000 |
| 19.3000 | 11910.0000 |
| 19.8600 | 7186.0000 |
| 20.1400 | 7583.0000 |
| 20.7000 | 8565.0000 |
| 20.9800 | 9192.0000 |
| 21.3600 | 12926.0000 |
| 21.6400 | 5603.0000 |
| 22.0200 | 8354.0000 |
| 22.2800 | 8942.0000 |
| 22.7400 | 5971.0000 |
| 23.1000 | 4026.0000 |
| 23.5000 | 4090.0000 |
| 23.9800 | 5087.0000 |
| 24.6000 | 5555.0000 |
| 25.2400 | 3890.0000 |
| 25.4600 | 3383.0000 |
| 25.9000 | 3086.0000 |
| 26.3200 | 4653.0000 |
| 26.6800 | 3897.0000 |

In some embodiments, Form A crystalline obicetrapib hydrochloride may be characterized by an x-ray powder diffraction pattern comprising a peak at about 8.6° 2θ, the presence of two peaks between about 9.7° 2θ and about 10.4° 2θ, the presence and the presence of two peaks at about 8.6° 2θ and about 9.0° 2θ. In some embodiments, Form A crystalline obicetrapib hydrochloride has an x-ray powder diffraction pattern substantially the same as that of FIG. 22.

In some embodiments, Form B crystalline obicetrapib hydrochloride is provided. A preparation of Form B crystalline obicetrapib hydrochloride is set forth in Example 30. An x-ray powder diffraction pattern for Form B crystalline obicetrapib hydrochloride is provided in FIG. 23. Table 5 provides illustrative peaks which may be present in Form B crystalline obicetrapib hydrochloride.

TABLE 5

| °2θ | Intensity |
|---|---|
| 4.4000 | 2499.6670 |
| 6.5000 | 1057.2506 |
| 7.6400 | 1515.7690 |
| 7.9600 | 1069.3528 |
| 8.7800 | 1534.2440 |
| 9.5800 | 872.0819 |
| 9.9200 | 1242.5219 |

TABLE 5-continued

| °2θ | Intensity |
| --- | --- |
| 10.3400 | 1139.7448 |
| 11.0000 | 621.7275 |
| 11.9600 | 627.8853 |
| 12.4800 | 714.8798 |
| 12.7200 | 984.4730 |
| 13.0200 | 709.5527 |
| 13.7600 | 976.8468 |
| 14.4600 | 578.0782 |
| 14.7800 | 702.8300 |
| 15.1000 | 697.3911 |
| 15.3200 | 920.2390 |
| 16.1600 | 1267.7367 |
| 16.6000 | 1914.8560 |
| 17.5400 | 1022.7526 |
| 18.2000 | 1873.4727 |
| 18.9600 | 1553.9690 |
| 19.4000 | 1395.4307 |
| 20.2200 | 2711.9712 |
| 21.1400 | 1785.6403 |
| 21.7400 | 1813.8923 |
| 22.5600 | 2673.6372 |
| 23.1400 | 1059.9265 |
| 24.0400 | 1409.4629 |
| 24.4600 | 1850.0687 |
| 25.4200 | 945.4888 |
| 26.0200 | 1065.7133 |
| 26.9600 | 910.6478 |

In some embodiments, Form B crystalline obicetrapib hydrochloride may be characterized by an x-ray powder diffraction pattern comprising peaks at about 6.5° 2θ, about 8.8° 2θ, and about 11.0° 2θ. In some embodiments, Form B crystalline obicetrapib hydrochloride has an x-ray powder diffraction pattern substantially the same as that of FIG. 23.

In some embodiments, Form C crystalline obicetrapib hydrochloride is provided. A preparation of Form C crystalline obicetrapib hydrochloride is set forth in Example 31. An x-ray powder diffraction pattern for Form C crystalline obicetrapib hydrochloride is provided in FIG. 24. Table 6 provides illustrative peaks which may be present in Form C crystalline obicetrapib hydrochloride.

TABLE 6

| °2θ | Intensity |
| --- | --- |
| 4.6600 | 1482.0829 |
| 6.6200 | 694.5864 |
| 7.6200 | 1011.8234 |
| 8.1000 | 804.8491 |
| 9.2800 | 822.3420 |
| 9.6800 | 793.2074 |
| 10.3600 | 809.9589 |
| 10.7800 | 757.3696 |
| 12.5000 | 691.6786 |
| 12.7400 | 712.6601 |
| 13.0800 | 788.3529 |
| 14.6000 | 779.5788 |
| 15.2400 | 744.2469 |
| 16.1400 | 1082.6187 |
| 16.5200 | 1204.0596 |
| 17.1600 | 1211.9613 |
| 17.6000 | 1030.1429 |
| 18.2600 | 1407.8092 |
| 18.8800 | 1465.9359 |
| 20.6000 | 2151.6992 |
| 21.6000 | 1704.6318 |
| 22.0800 | 1551.0829 |
| 24.9600 | 968.9622 |

Figure 24:
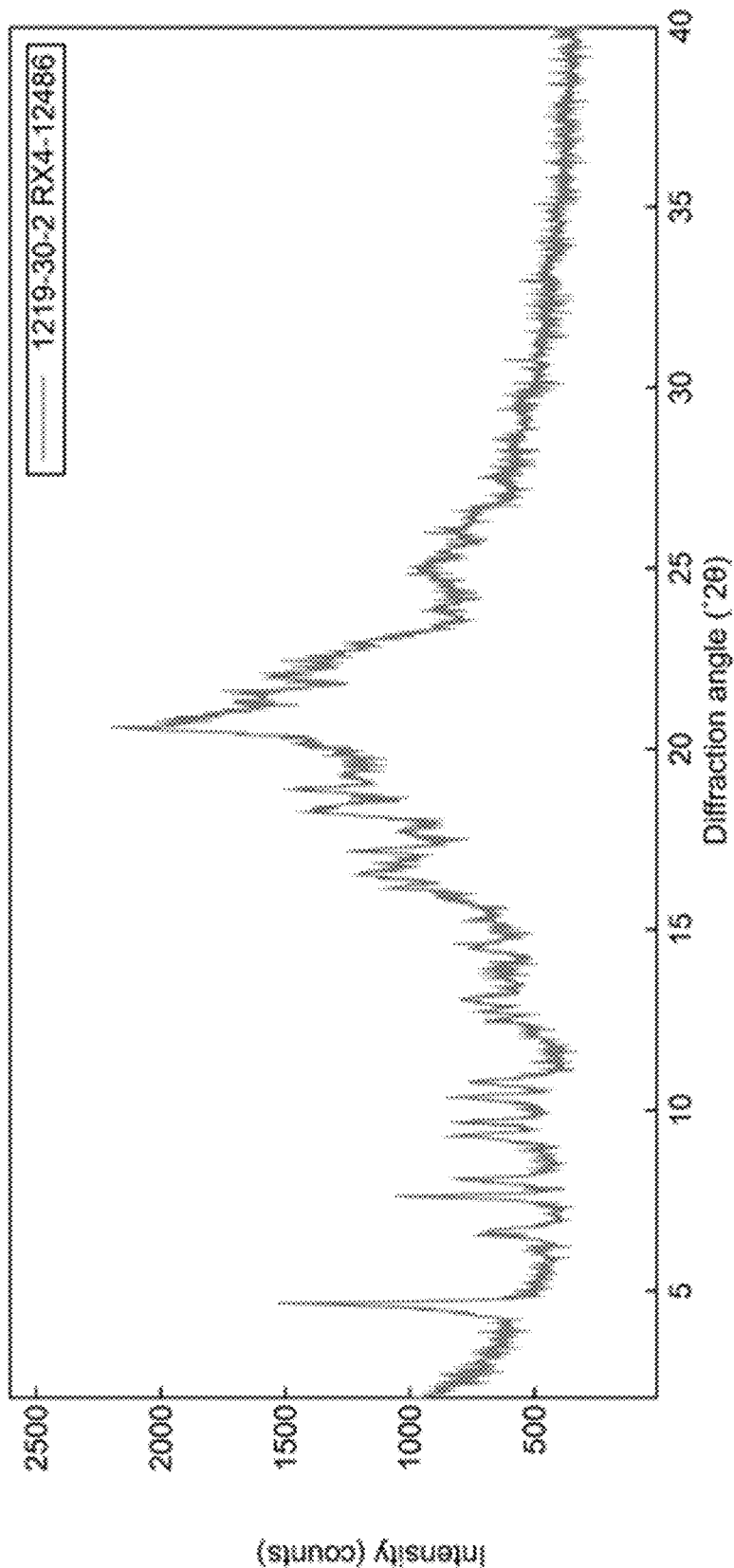
FIG. 24 is an x-ray powder diffraction pattern of crystalline obicetrapib hydrochloride Form C.

In some embodiments, Form C crystalline obicetrapib hydrochloride has an x-ray powder diffraction pattern substantially the same as that of FIG. 24.

In some embodiments, Form D crystalline obicetrapib hydrochloride is provided. A preparation of Form D crystalline obicetrapib hydrochloride is set forth in Example 32. An x-ray powder diffraction pattern for Form D crystalline obicetrapib hydrochloride is provided in FIG. 25. Table 7 provides illustrative peaks which may be present in Form D crystalline obicetrapib hydrochloride.

TABLE 7

| °2θ | Intensity |
| --- | --- |
| 4.5800 | 6901.0000 |
| 5.8800 | 6409.0000 |
| 6.3000 | 5406.0000 |
| 7.8000 | 7764.0000 |
| 8.2600 | 3308.0000 |
| 9.1200 | 5272.0000 |
| 10.1400 | 3769.0000 |
| 11.7000 | 4739.0000 |
| 12.8200 | 4035.0000 |
| 13.4000 | 5466.0000 |
| 13.6600 | 5320.0000 |
| 15.1000 | 4045.0000 |
| 15.5800 | 4284.0000 |
| 16.4000 | 5957.0000 |
| 17.5800 | 7575.0000 |
| 18.1800 | 10220.0000 |
| 18.7400 | 9505.0000 |
| 19.4200 | 10317.0000 |
| 19.8400 | 11277.0000 |
| 20.3600 | 10054.0000 |
| 20.7200 | 8246.0000 |
| 21.0400 | 8304.0000 |
| 22.0400 | 7496.0000 |
| 22.4600 | 9638.0000 |
| 23.9200 | 7387.0000 |
| 24.9800 | 4937.0000 |
| 25.4000 | 5478.0000 |
| 26.0800 | 5495.0000 |
| 27.3000 | 4092.0000 |
| 28.8600 | 3671.0000 |

Figure 25:
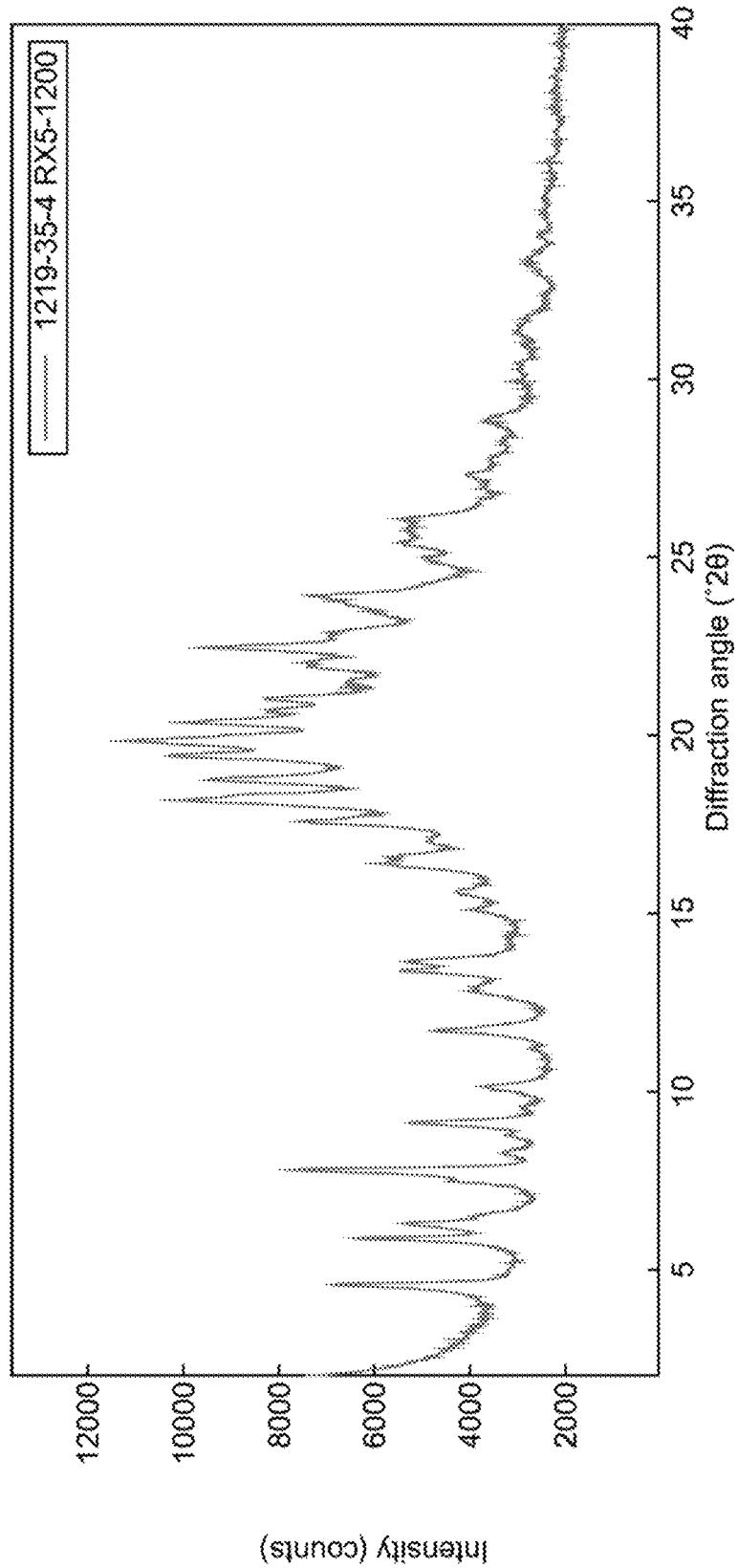
FIG. 25 is an x-ray powder diffraction pattern of crystalline obicetrapib hydrochloride Form D.

In some embodiments, Form D crystalline obicetrapib hydrochloride has an x-ray powder diffraction pattern substantially the same as that of FIG. 25.

Figure 26:
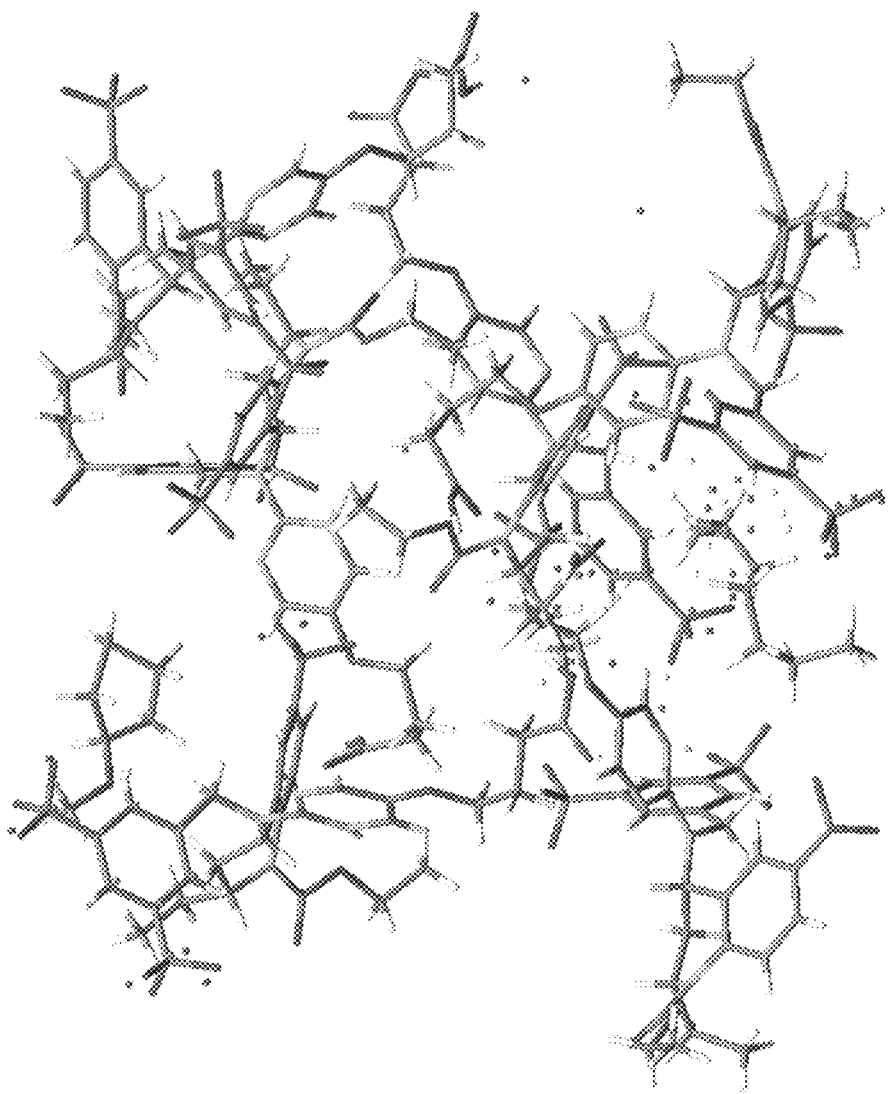
FIG. 26 is a rendition of the asymmetric unit from the single crystal structure of crystalline obicetrapib hydrochloride.

Single crystal x-ray diffraction is another technique that may be used to elucidate the structure of a crystalline material. The single crystal structure solution showing the asymmetric unit of a crystal of crystalline obicetrapib hydrochloride made in accordance with Example 33 is provided in FIG. 26. The unit cell parameters are found below at Table 8.

TABLE 8

| crystal system, space group | Monoclinic |
| --- | --- |
| data collection temperature (K) | 150(2) |
| a (Å) | 22.088(10) |
| b (Å) | 19.332(8) |
| c (Å) | 28.582(11) |
| α (°) | 90 |
| β (°) | 109.136(15) |
| γ (°) | 90 |
| volume (Å$^3$) | 11531(8) |
| Z | 2 |

Although disordered, the solution provides a pattern which is similar to that of Form B crystalline obicetrapib hydrochloride even though the preparation used a solvent system which can yield Form A crystalline obicetrapib hydrochloride. The solution shows four protonated obicetrapib moieties (each singly protonated at the $N_3$ nitrogen on the pyrimidine ring) and each of four chloride anions hydrogen-bond to the N—H$^+$ units at $N_3$ of the pyrimidine ring in the cell unit. The structure further contains two neutral obicetrapib molecules as well as solvent molecules of heptane and CPME. It is believed that one CPME molecule and one heptane molecule are in the unit cell. Additional void space exists which may include at least one additional heptane molecule, and possibly up to four additional heptane molecules.

The crystal structure suggests a complex and variable structure associated with crystalline obicetrapib hydrochloride. It is a solvate given the presence of CPME and heptane.

Figure 27:
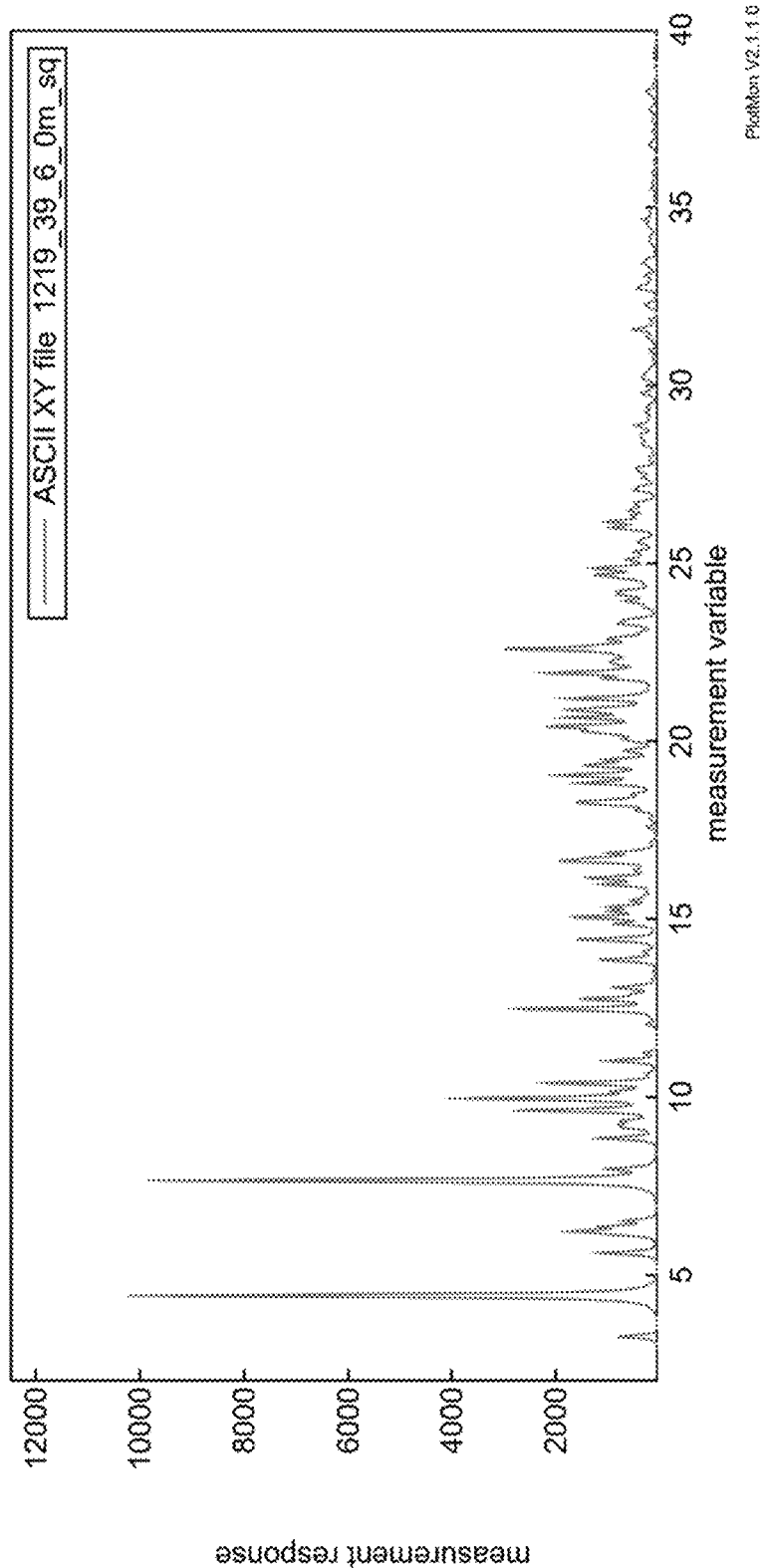
FIG. 27 is a calculated x-ray powder diffraction pattern of a single crystal of crystalline obicetrapib hydrochloride.
Figure 28:
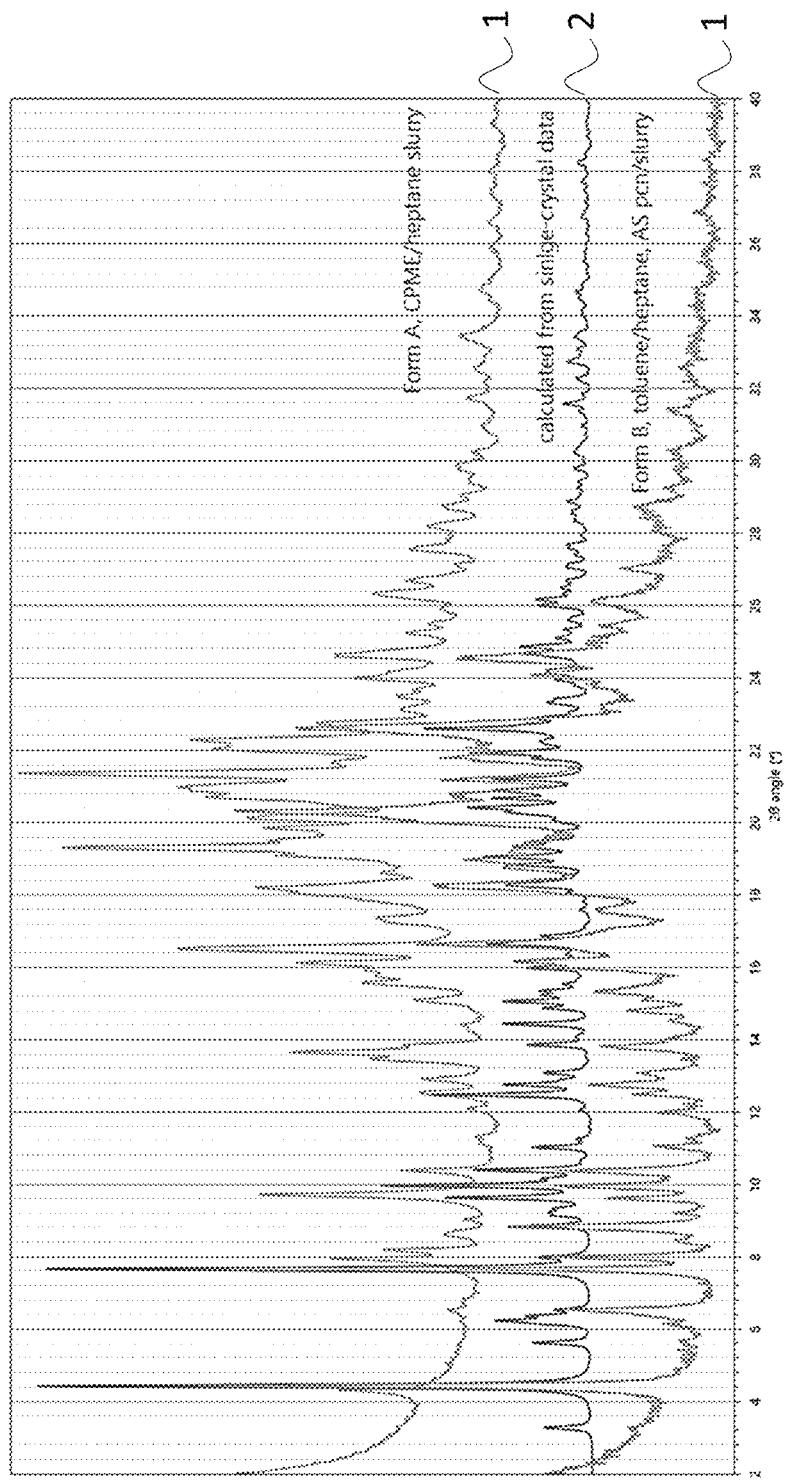
FIG. 28 is an x-ray powder diffraction overlay of the calculated pattern of FIG. 27 and x-ray powder diffraction patterns of Form A crystalline obicetrapib hydrochloride and Form B crystalline obicetrapib hydrochloride.

The single crystal data was used to calculate a powder pattern which can be found at FIG. 27. An x-ray powder diffraction overlay of the calculated pattern, Form A crystalline obicetrapib hydrochloride, and Form B crystalline obicetrapib hydrochloride is found at FIG. 28. Pattern 1 is associated with Form A crystalline obicetrapib hydrochloride, Pattern 2 is associated with the calculated pattern, and Pattern 3 is associated with Form B crystalline obicetrapib hydrochloride. Pattern 2 appears similar to Pattern 3.

Another intermediate used in the preparation of obicetrapib is that of Formula (VI)

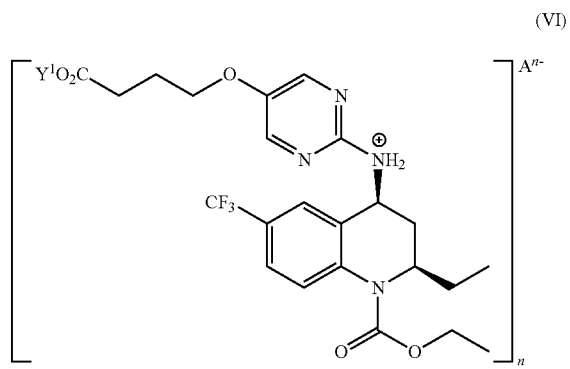

(VI)

wherein $Y^1$ is a protecting group (e.g., as described herein); $A^{n-}$ is an anion; and n is an integer from 1-3.

In one embodiment, the compound of Formula (VI) is a mesylate salt where n is 1, $Y^1$ is t-butyl, and has the structure of Compound 1D.

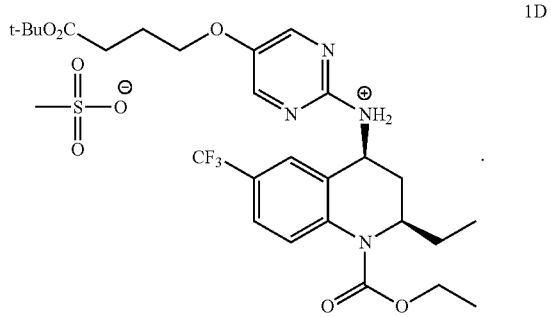

1D

Figure 20:
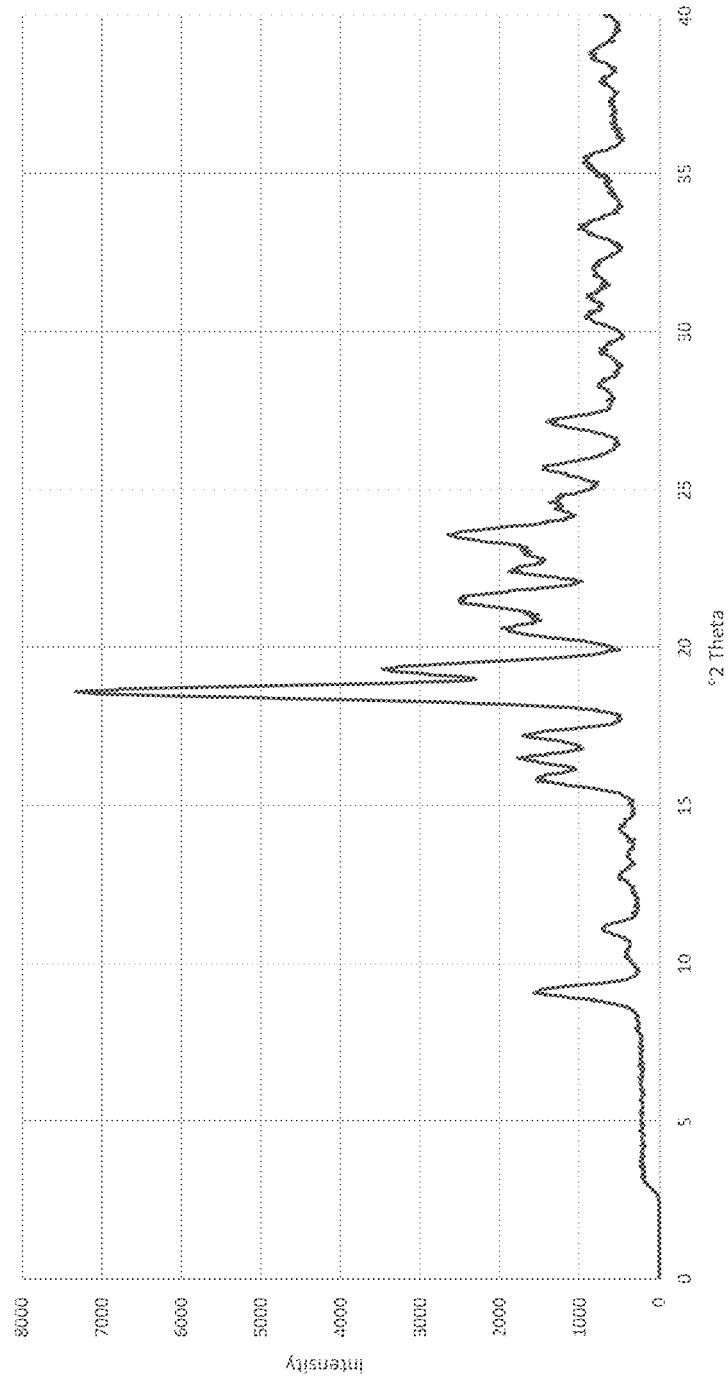
FIG. 20 is an x-ray powder diffraction pattern of crystalline Compound 1D.
Figure 21:
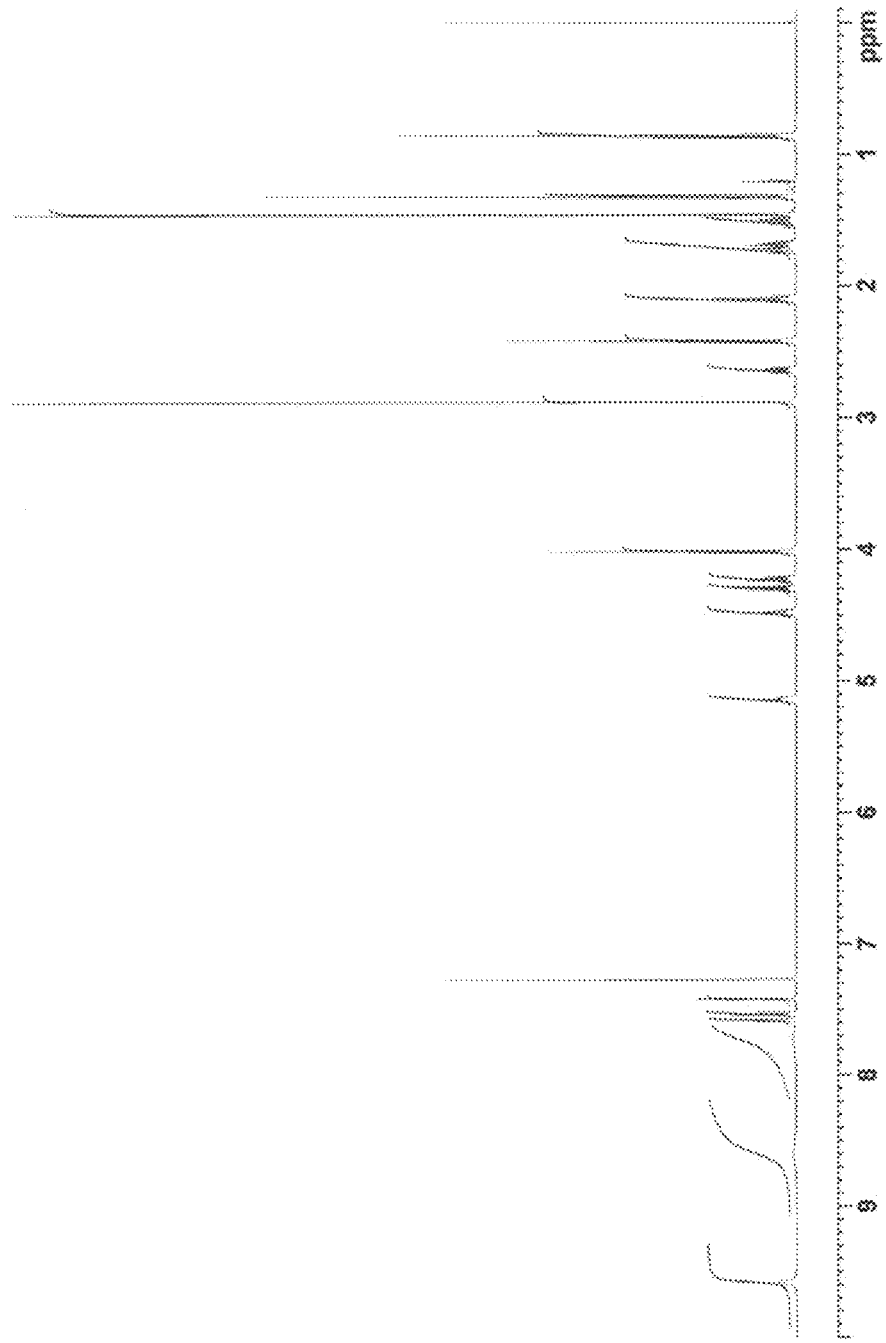
FIG. 21 is $^1$H-NMR spectrum of Compound 1D.
Figure 22:
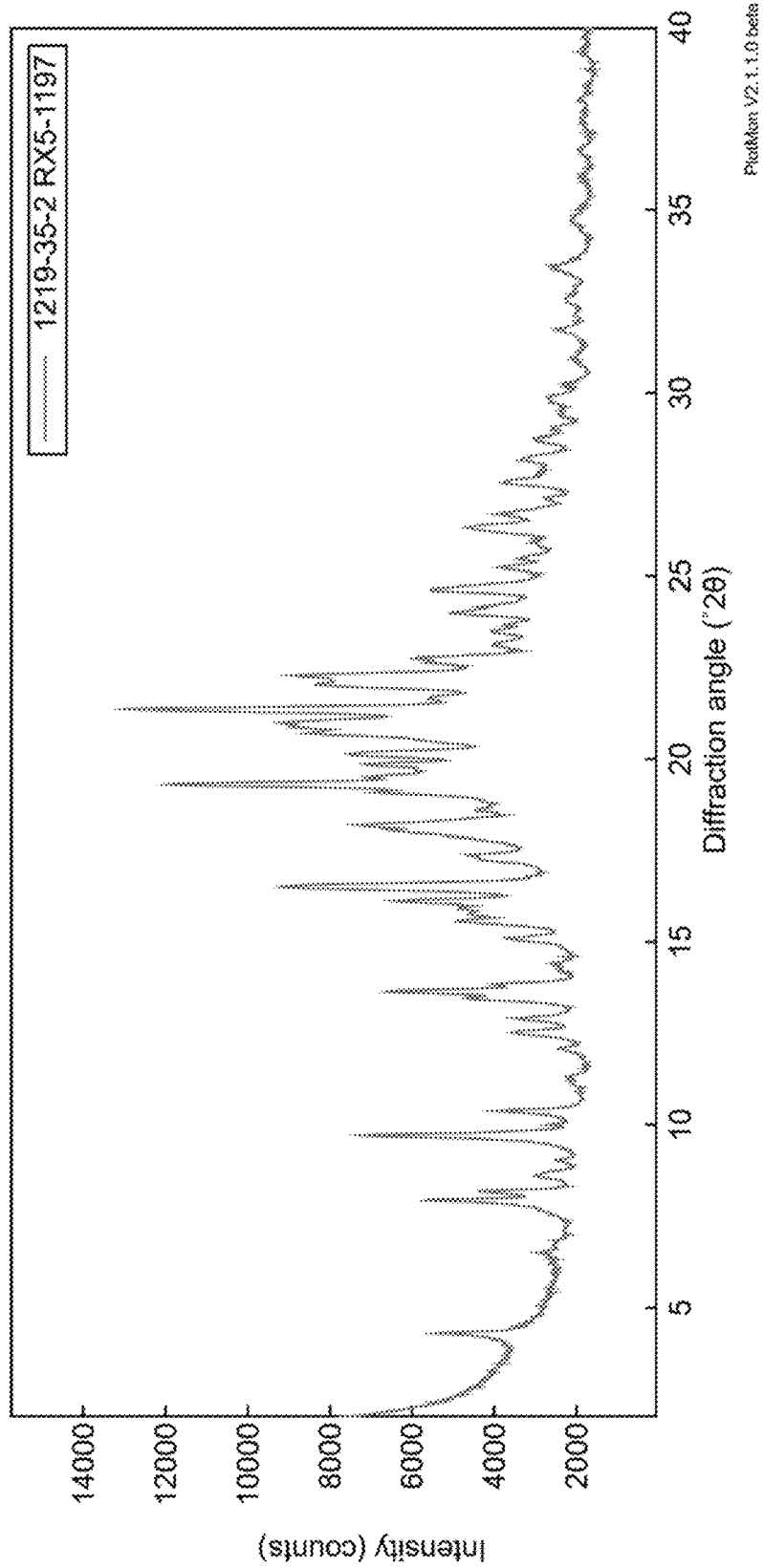
FIG. 22 is an x-ray powder diffraction pattern of crystalline obicetrapib hydrochloride Form A.
Figure 23:
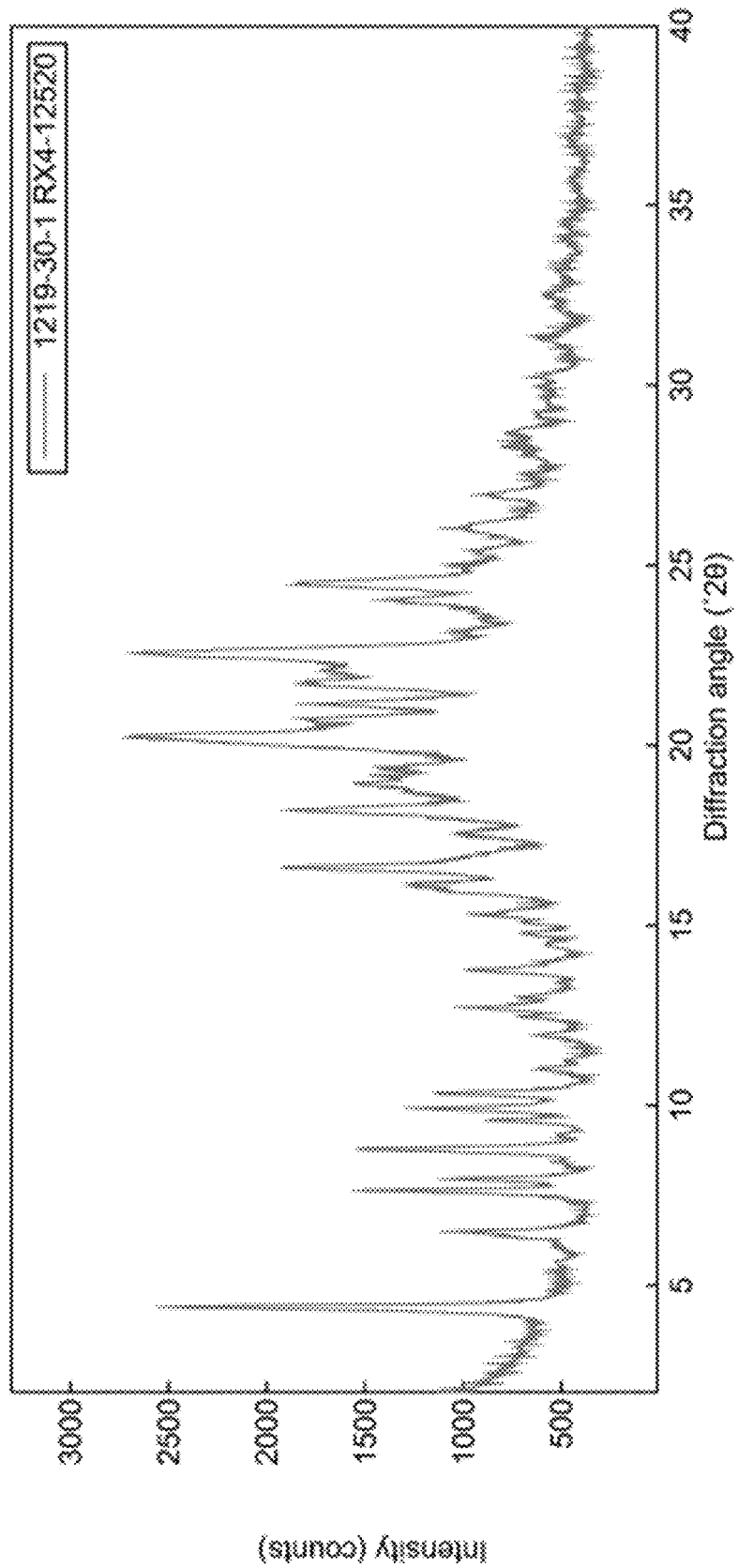
FIG. 23 is an x-ray powder diffraction pattern of crystalline obicetrapib hydrochloride Form B.

A $^1$H-NMR spectrum of Compound 1D (in solution) can be found in FIG. 21. Crystalline Compound 1D may be characterized by an x-ray powder diffraction pattern comprising one or more peaks at about 5.2°2θ or about 9.1°2θ. In some embodiments, crystalline Compound 1D may be characterized by an x-ray powder diffraction pattern comprising one or more peaks at about 5.2°2θ, about 9.1°2θ, about 15.9°2θ, about 16.5°2θ, about 17.2°2θ, about 18.6°2θ, and about 19.2°2θ. Table 9 provides illustrative peaks which may be present in crystalline Compound 1D (with the peak at about 5.2°2θ not measured due to instrument limitations in reflection mode). In some embodiments, crystalline Compound 1D may be characterized by an x-ray powder diffraction pattern substantially the same as FIG. 20.

TABLE 9

| °2θ | Intensity |
|---|---|
| 9.1 | 1530 |
| 15.9 | 1470 |
| 16.5 | 1700 |
| 17.2 | 1680 |
| 18.6 | 7331 |
| 19.2 | 3400 |
| 20.6 | 1870 |
| 21.6 | 2440 |
| 22.5 | 1800 |
| 23.5 | 2580 |
| 25.7 | 1400 |
| 27.2 | 1370 |

Crystalline compounds such as crystalline Compound 1D and a crystalline obicetrapib HCl, for example, may be characterized by x-ray powder diffraction. An x-ray powder diffraction pattern is an x-y graph with °2θ (diffraction angle) on the x-axis and intensity on the y-axis. The peaks are usually represented and referred to by their position on the x-axis rather than the intensity of peaks on the y-axis because peak intensity can be particularly sensitive to sample orientation (see Pharmaceutical Analysis, Lee & Web, pp. 255-257 (2003)). Thus, intensity is not typically used to characterize solid forms. The data from x-ray powder diffraction may be used in multiple ways to characterize crystalline forms. For example, the entire x-ray powder diffraction pattern output from a diffractometer may be used to characterize a crystalline obicetrapib HCl compound or a crystalline Compound 1D. A smaller subset of such data, however, may also be, and typically is, suitable for characterizing such compounds. For example, a collection of one or more peaks from such a pattern may be used to so characterize these compounds. When the phrase "one or more peaks" of a list of peaks from an x-ray powder diffraction pattern are provided, what is generally meant is that any combination of the peaks listed may be used for characterization. Further, the fact that other peaks are present in the x-ray powder diffraction pattern, generally does not negate or otherwise limit that characterization.

In addition to the variability in peak intensity, there may also be variability in the position of peaks on the x-axis. This variability can, however, typically be accounted for when reporting the positions of peaks for purposes of characterization. Such variability in the position of peaks along the x-axis may derive from several sources (e.g., sample preparation, particle size, moisture content, solvent content, instrument parameters, data analysis software, and sample orientation). For example, samples of the same crystalline material prepared under different conditions may yield slightly different diffractograms, and different x-ray instruments may operate using different parameters and these may lead to slightly different diffraction patterns from the same crystalline solid. Due to such sources of variability, it is common to recite x-ray diffraction peaks using the word "about" prior to the peak value in °2θ. For purposes of data reported herein, that value is generally ±0.2° 2θ are intended to be reported with such a variability whenever disclosed herein whether the word "about" is present or not. Variability may, in some instances, be higher depending on instrumentation conditions including how well instruments are maintained.

In some embodiments, crystalline Compound 1D may be further characterized by an x-ray powder diffraction pattern substantially the same as the x-ray powder pattern as that of FIG. 20.

In many aspects of the disclosure, there is provided a method of preparing an amorphous calcium salt of obicetrapib, such as amorphous obicetrapib hemicalcium, wherein the method comprises:

i. treating obicetrapib with HCl to obtain crystalline obicetrapib HCl;

ii. isolating crystalline obicetrapib HCl;

iii. preparing an amorphous calcium salt of obicetrapib, such as amorphous obicetrapib hemicalcium, from the crystalline obicetrapib HCl isolated in step (ii); and iv. isolating an amorphous calcium salt of obicetrapib, such as amorphous obicetrapib hemicalcium.

In other aspects of the disclosure, there is provided a method of preparing obicetrapib wherein the method comprises:

(a) preparing a compound of Formula (IV), by coupling a compound of Formula (II) or a salt thereof, with a compound of Formula (III);

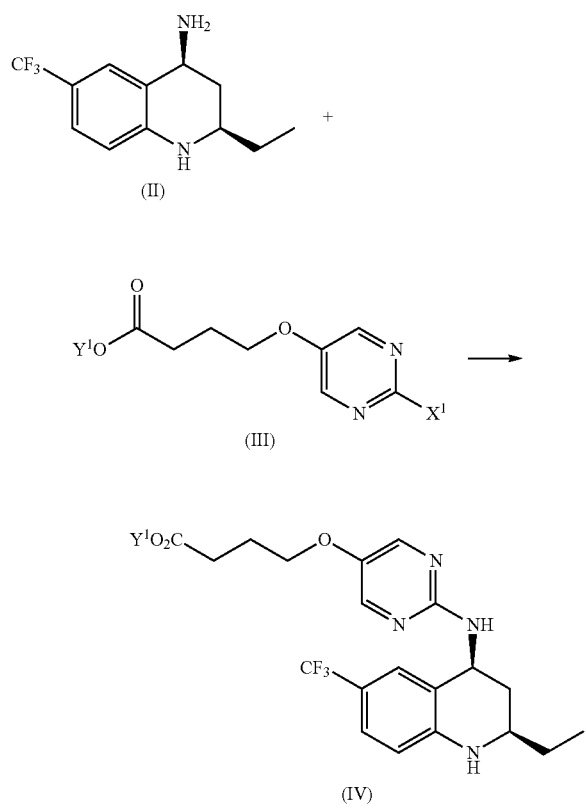

where $X^1$ is a leaving group and $Y^1$ is a protecting group;

(b) preparing a carbamate of Formula (V) from the compound of Formula (IV) and isolating as a solid salt form of Formula (VI):

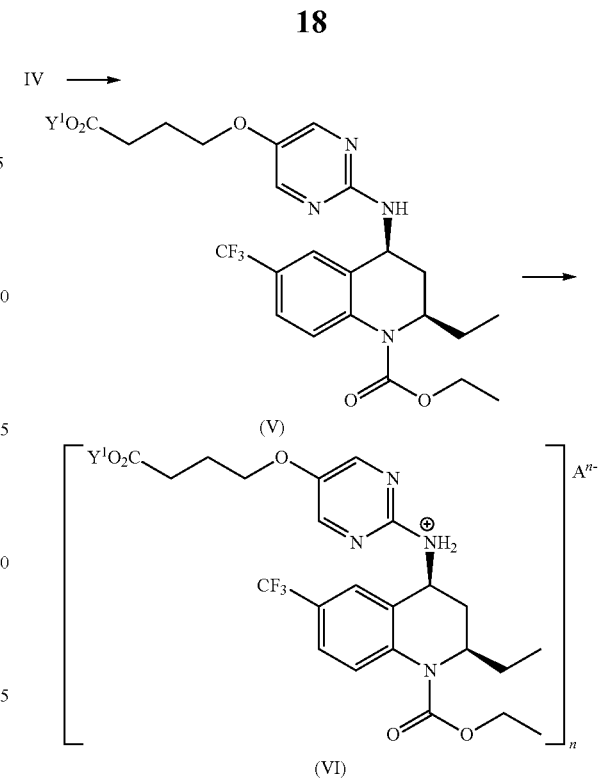

where $Y^1$ is a protecting group, $A^{n-}$ is an anion and wherein n is an integer from 1-3;

(c) optionally desalting the compound of Formula (VI) and alkylating with a compound of Formula (VII) to provide a compound of Formula (VIII):

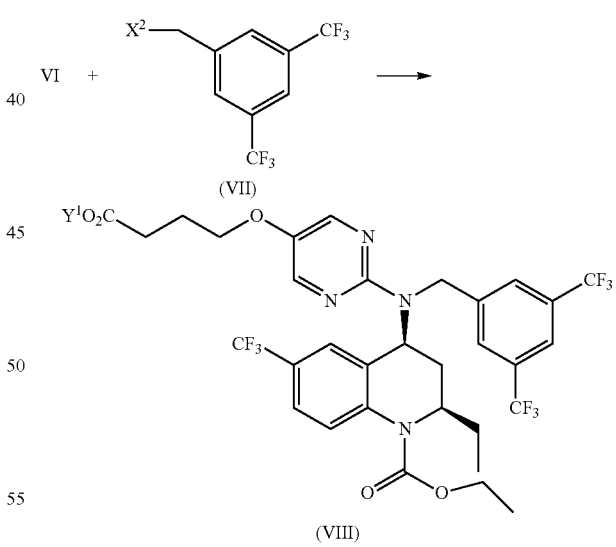

where, $X^2$ is a leaving group, $Y^1$ is a protecting group; and (d) converting the compound of Formula (VIII) to obicetrapib, wherein the reaction steps (a)-(d) are performed in an organic solvent, compounds (IV), (V) and (VIII) are optionally not isolated from the organic solvent, and wherein the process does not need to comprise chromatography.

The reactions in steps (a)-(d) of the subject method are performed in a solvent, and intermediate compounds of Formulae (IV), (V) and (VIII) do not need to be isolated from their respective solvents if they are to be processed further to end products. This means that any solvent swap between reaction steps (x) and (x+1) takes places by evaporating at least part of the solvent used in step (x) and by gradually adding the solvent of step (x+1), such that the compound remains in solution during the solvent swap. The intermediate compound of Formula (VI) may be isolated from the solvent as a salt in solid form, such that it can be washed to remove impurities. This isolation step ensures sufficient purity of downstream products. The subject process does not need to comprise purification steps using chromatography, such as column chromatography to achieve the chemical purity levels described herein.

Method of Preparing an Amorphous Calcium Salt Such as Amorphous Obicetrapib Hemicalcium)— Steps (i)-(ii) from Aspects (i)-(iv)

In some embodiments of the method of preparing an amorphous calcium salt of obicetrapib such as amorphous obicetrapib hemicalcium, the method includes step (i), treating obicetrapib with HCl in an organic solvent to obtain crystalline obicetrapib HCl.

In some embodiments, crystalline obicetrapib HCl has a purity of 98% or more, such as 98.5% or more, 99% or more, 99.5% or more, or even more.

In some embodiments, the HCl in step (i) is in a suitable solvent. Such solvent may be an aqueous solvent or an organic solvent. In some embodiments, the organic solvent used in step (i) comprises a mixture of a solvent and an anti-solvent. In some embodiments, the solvent is selected from methanol, ethanol, isopropanol, acetic acid, acetonitrile, acetone, methyl isobutyl ketone, isopropyl acetate, tetrahydrofuran, methyl t-butyl ether, cyclopentyl methyl ether, N-methyl-2-pyrrolidone, dimethyl sulfoxide, dimethylformamide, 2-methyl-tetrahydrofuran, dichloromethane, 1,4-dioxane, 1,2-diflurobenzene, toluene, hexafluoroisopropanol, and water. In some embodiments, the anti-solvent is selected from n-heptane, n-hexane, n-pentane, and cyclohexane.

In some embodiments, the HCl has sufficient solubility in the anti-solvent such that it can be used as a suitable solvent. In some embodiments, the organic solvent used in step (i) comprises a mixture of cyclopentyl methyl ether and n-heptane. In some embodiments, the organic solvent used in step (i) further comprises toluene. In some embodiments, toluene is the majority component of the organic solvent.

In some embodiments, step (i) comprises providing obicetrapib in a mixture of cyclopentyl methyl ether and n-heptane, raising the temperature to between 35° C. and 40° C. under agitation, adding dry HCl in cyclopentyl methyl ether and raising the temperature again to between 50° C. and 55° C., then adding further n-heptane as an anti-solvent. At this point, a small portion of the reaction mixture can optionally be extracted, cooled to a temperature of between 10° C. and 15° C., to obtain a slurry of crystals of crystalline obicetrapib HCl in a mixture of cyclopentyl methyl ether and n-heptane (referred to herein as a "seed crystal slurry"). Optionally, all or a portion of the seed crystal slurry of crystalline obicetrapib HCl can then be added back to the reaction mixture. The seeds assist with nucleation but are not required. The resulting reaction mixture is then cooled to a temperature between 5° C. and 15° C. (such as from 10° C. to 15° C.), followed by crystallizing the crystalline obicetrapib HCl from the system under agitation. In some embodiments, the crystalline obicetrapib HCl is crystallized over a period of 12 hours or more, with subsequent filtration (e.g., through a filter dryer), one or more optional washing steps, such as with a mixture of cyclopentyl methyl ether and n-heptane, and drying. In some cases, a wet filter cake of crystalline obicetrapib HCl is dried in vacuo in steps using temperatures of 25° C.-30° C., 30° C.-40° C., 40° C.-50° C. then 50° C.-55° C., such as 25° C., 35° C., 46° C., and 54° C.

In some embodiments, the method of preparing crystalline obicetrapib HCl comprises the addition of seed crystals (e.g., as a seed crystal slurry). The seed crystals of an HCl compound can be formed as a slurry by following step (i) as set out above and after addition of dry HCl in cyclopentyl methyl ether and anti-solvent n-heptane, extracting a small portion of the reaction mixture, cooling to a temperature between 10° C. and 15° C., to provide a slurry of crystals of crystalline obicetrapib HCl in cyclopentyl methyl ether and n-heptane.

Accordingly, in one embodiment, step (i) comprises providing crystalline obicetrapib HCl in a mixture of cyclopentyl methyl ether and n-heptane, raising the temperature to between 35° C. and 45° C. under agitation, adding dry HCl in cyclopentyl methyl ether and raising the temperature again to between 50° C. and 55° C., addition of further n-heptane as anti-solvent, and the optional addition of seed crystals of an HCl compound (e.g., as a seed crystal slurry prepared as described herein), cooling to a temperature between 5° C. and 15° C. (such as from 10° C. to 15° C.), followed by crystallizing the crystalline obicetrapib HCl from the system under agitation. In some embodiments, the crystalline obicetrapib HCl is crystallized over a period of 12 hours or more, with subsequent filtration, one or more optional washing steps, such as with a mixture of cyclopentyl methyl ether and n-heptane, and drying. In some embodiments, crystalline obicetrapib HCl is dried in vacuo. In some embodiments, crystalline obicetrapib HCl is subjected to drying in a vacuum drying cabinet at 25 mbar pressure and at a temperature of 55° C. for 10 hours or more. In some embodiments, after the drying procedure, the crystalline obicetrapib HCl includes less than 0.1 weight percent residual cyclopentyl methyl ether.

In some embodiments, step (i) comprises providing the solution of obicetrapib in cyclopentyl methyl ether with a concentration between 30 and 40 weight percent, such as from 33 to 37 weight percent, based on the weight of the solution, less than 1 weight percent of the first organic solvent used in step (d) (such as toluene), less than 1 weight percent of n-heptane based on weight of solution, addition of n-heptane, raising the temperature to 35° C. to 45° C. under agitation, adding dry HCl in cyclopentyl methyl ether and raising the temperature again to 50° C. to 55° C., addition of further n-heptane as anti-solvent, optional addition of seed crystals of a crystalline obicetrapib HCl (e.g., as a seed crystal slurry prepared as described herein), cooling to a temperature between 10° C. and 15° C., followed by crystallizing crystalline obicetrapib HCl from the system under agitation, such as during a period of at least 12 hours, with subsequent filtration, one or more washing steps with a mixture of cyclopentyl methyl ether and n-heptane, and drying, such as in vacuo. In some embodiments, the amount of toluene is substantially greater.

In some embodiments the crystalline obicetrapib HCl from step (i) is isolated in step (ii). In some embodiments, the isolated crystalline obicetrapib HCl has a purity of 98% or more, such as 98.5% or more, 99% or more, 99.5% or more, 99.7%, or even more.

Another embodiment of the disclosure concerns the crystalline obicetrapib HCl, obtained by or obtainable by the process as defined herein.

Still another embodiment of the disclosure is directed to HCl obicetrapib, including crystalline obicetrapib HCl.

In some embodiments, the crystalline obicetrapib HCl is stored at controlled room temperature and under a nitrogen atmosphere and is protected from moisture to prevent the formation of an amorphous solid such as from desolvation.

Method of Preparing an Amorphous Calcium Salt of Obicetrapib, Such as Amorphous Obicetrapib Hemicalcium—Steps (iii)-(iv) from Aspects (i)-(iv)

In some embodiments of the method of preparing an amorphous calcium salt of obicetrapib, such as amorphous obicetrapib hemicalcium, the method includes step (iii)-(iv), preparing an amorphous calcium salt of obicetrapib from crystalline obicetrapib HCl isolated in step (ii), and isolating an amorphous calcium salt of obicetrapib, such as amorphous obicetrapib hemicalcium.

In some embodiments of the method of isolating an amorphous calcium salt of obicetrapib according to step (iv), the amorphous calcium salt of obicetrapib is in the form of amorphous obicetrapib hemicalcium:

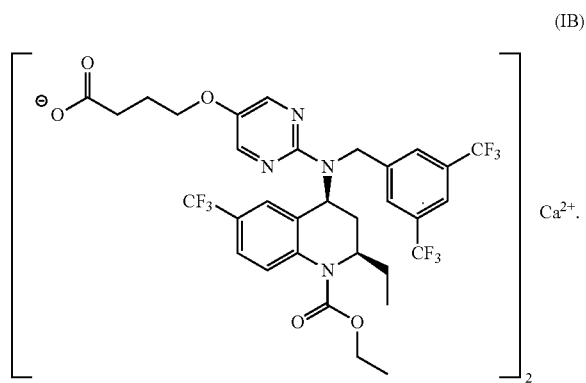

In some embodiments of the method of preparing obicetrapib, step (iii) includes the following steps:
(iii-1) converting crystalline obicetrapib HCl of step (ii) to provide obicetrapib in an organic solvent;
(iii-2) treating obicetrapib in the organic solvent with aqueous sodium hydroxide to form a sodium salt of obicetrapib; and
(iii-3) treating the sodium salt of obicetrapib with aqueous calcium chloride to form amorphous obicetrapib hemicalcium;
wherein the compounds in steps (iii-1) and (iii-2) are not isolated.

Accordingly, in some embodiments step, (iii-1) comprises the following steps:
(aa) providing crystalline obicetrapib HCl, as isolated in step (ii);
(bb) dissolving crystalline obicetrapib HCl in a mixture of water and isopropyl acetate under agitation. In some embodiments, step (bb) is conducted at a temperature between 15° C. and 25° C.;
(cc) allowing phase separation and subjecting the resulting organic phase to one or more subsequent washing steps with water, wherein each washing step is followed by separating off the aqueous phase, resulting in a washed organic phase; and
(dd) performing two or more distillations on the washed organic phase resulting from step (cc) at a temperature of 50° C. or lower (such as 30° C. or lower), with intermediate additions of ethanol, to obtain a solution of obicetrapib in ethanol.

In some embodiments step, (iii-2) comprises the following steps:
(ee) adding an aqueous NaOH solution to the solution obtained in step (dd) and agitating the resulting mixture, such as at a temperature between 20° C. and 25° C. for at least 4 hours, to obtain a solution of the sodium salt of obicetrapib; and
(ff) optionally filtering the solution obtained in step (ee).

In some embodiments step, (iii-3) comprises the following steps:
(gg) preparing a CaCl2) solution by adding deionized water to CaCl2) under agitation, followed by adding ethyl acetate as a co-solvent, and stirring the resulting mixture for 10 to 30 minutes;
(hh) cooling the CaCl2) solution obtained in step (gg) to a temperature from 8° C. to 12° C. and adding via a filter to the solution obtained in step (ff) or (ee) under agitation at said temperature;
(ii) stirring the slurry resulting from step (hh) for about 1 to about 10 hours. In some embodiments of step (ii), the stirring is conducted at a temperature between 8° C. and 12° C.;
(jj) isolating the solids from the slurry obtained in step (ii) by filtration. In some embodiments of step (jj), the isolating is conducted at a temperature between 8° C. and 12° C.;
(kk) washing the filtration residue obtained in step (j) with water in one or more washing steps. In some embodiments of step (kk), the washing is conducted at a temperature between 8° C. and 12° C.; and
(ll) drying the washed residue obtained in step (kk), such as in vacuo at a temperature from 40° C. to 50° C. for more than 16 hours (such as 50 hours, 100 hours, 150 hours, or 200 hours, or even more), to obtain amorphous obicetrapib hemicalcium (also sometimes referred to herein as compound 3).

In some embodiments, amorphous obicetrapib hemicalcium is submitted to a subsequent reworking procedure. In some embodiments, amorphous obicetrapib hemicalcium is further reworked by dissolving in ethanol (such as twice the weight of ethanol relative to amorphous obicetrapib hemicalcium) at a temperature of 25° C. to 50° C., followed by cooling to 10° C. to 15° C., followed by filtering into a mixture of aqueous calcium chloride solution and ethyl acetate, also cooled to 10° C. to 15° C., followed by filtering, washing with water and drying in vacuo at 45° C. or less for 20 hours or more.

In some embodiments of step (iv), amorphous obicetrapib hemicalcium is isolated with a purity of 95% or more, such as a purity of 95.5% or more, 96% or more, 96.5% or more, 97% or more, 97.5% or more, 98% or more, 98.5% or more, 99% or more, 99.1% or more, 99.2% or more, 99.3% or more, 99.4% or more, 99.5% or more, 99.6% or more, 99.7% or more, 99.8% or more, or 99.9% or more.

In some embodiments, amorphous obicetrapib hemicalcium is subjected to a milling process. In some embodiments, the milling process is adapted (e.g., parameters such as feed rate, venturi pressure and mill pressure are adapted) to allow production of micronized amorphous obicetrapib hemicalcium.

Method of Preparing Obicetrapib—Step (a) from Aspects (a)-(d)

In step (a) of the process for preparing obicetrapib according to the present disclosure, the compound of Formula (II), or a salt thereof, is coupled with a compound of Formula (III) to provide a compound of Formula (IV) (where $X^1$ is a leaving group and $Y^1$ is protecting group, e.g., as described herein).

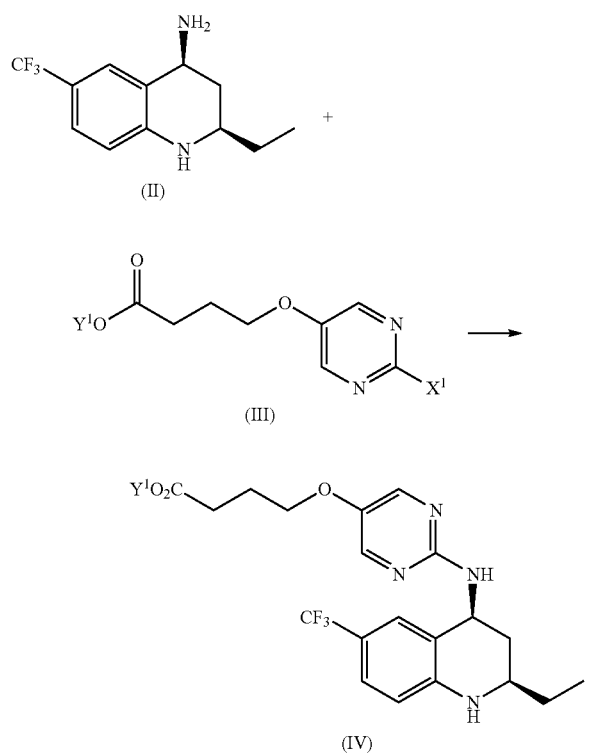

Step (a) of the subject method, starts with a compound of Formula (II) (2R,4S)-4-amino-2-ethyl-6-trifluoromethyl-3,4-dihydro-2H-quinoline), or a salt thereof:

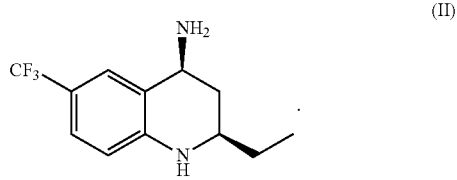 [SMILES: CC[C@@H]1C[C@H](N)c2cc(C(F)(F)F)ccc2N1]

The compound of Formula (II) can for example be obtained using a process as disclosed in WO2016/024858A1 or in WO2007/116922A1, both of which are incorporated herein by reference in their entirety. In some embodiments the compound of Formula (II) can be obtained from a corresponding salt that is stable and can be obtained in pure and solid form. The solid form can be amorphous or crystalline. In some embodiments, the compound of Formula (II) is obtained from a corresponding crystalline salt.

In some embodiments, the compound of Formula (II) provided in step (a) is a salt of the Formula (IIA) or (IIB):

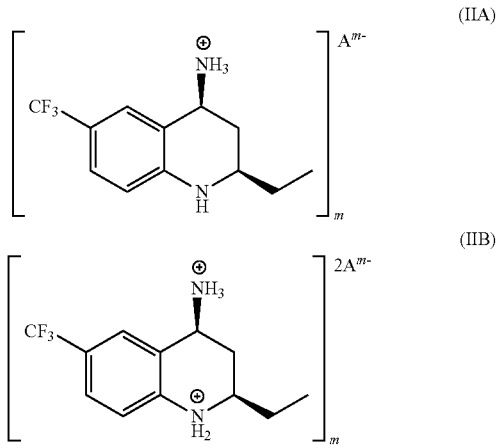

wherein $A^{m-}$ is an anion and n is an integer from 1-3.

In some embodiments, the compound of Formula (II) provided in step (a) is a salt of Formula (IIA). In some embodiments, the compound of Formula (IIA) is used directly in the coupling reaction with the compound of Formula (III) without performing a desalting step.

In some embodiments, the compound of Formula (II) provided in step (a) is a salt of Formula (IIB). In some embodiments, the compound of Formula (IIB) is used directly in the coupling reaction with the compound of Formula (III) without performing a desalting step.

In some embodiments, the compound of Formula (II) in step (a) is obtained from a salt of Formula (IIA) or (IIB). In some embodiments, the following steps are carried out before the coupling reaction of step (a):

(pre-a1) providing a compound of Formula (IIA) or (IIB):

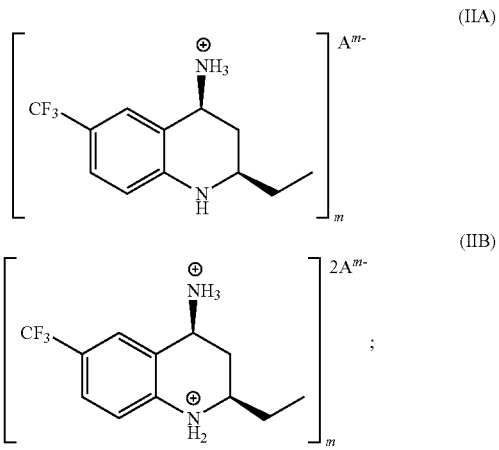

(pre-a2) desalting the compound of Formula (IIA) or (IIB) to obtain the compound of Formula (II), wherein the reaction in step (pre-a2) is performed in an organic solvent, the compound of Formula (II) is not isolated from the organic solvent, and the process does not comprise chromatography.

In some embodiments, the compound of Formula (II) in step (a) is obtained from a salt of Formula (IIA). In some embodiments, the compound of Formula (II) in step (a) is obtained from a salt of Formula (IIB).

In some embodiments the salts of Formula (IIA) or (IIB), are chosen from salts with an anion $A^{m-}$ selected from a sulfonate (e.g., besylate, tosylate, napsylate, camsylate, esylate, edisylate, or mesylate), a sulfate (e.g., methylsulfate), a halogen (e.g., chloride, iodide, or bromide), acetate, aspartate, benzoate, bicarbonate, bitartrate, carbonate, citrate, decanoate, fumarate, gluceptate, gluconate, glutamate, glycolate, hexanoate, hydroxynaphthoate, isethionate, lactate, lactobionate, malate, maleate, mandelate, mucate, nitrate, octanoate, oleate, pamoate, pantothenate, phosphate, polygalacturonate, propionate, salicylate, stearate, succinate, tartrate, and teoclate.

In some embodiments the salts of Formula (IIA) or (IIB), are chosen from salts with an anion $A^{m-}$ selected from chloride, bromide, bitartrate, a sulfate, and a sulfonate.

In some embodiments the salts of Formula (IIA) or (IIB), are chosen from salts with an anion $A^{m-}$ selected from chloride, bromide, bitartrate, and mesylate.

In some embodiments of the salts of Formula (IIA) or (IIB), m is 1.

In some embodiments the salt is of Formula (IIA), and the anion $A^{m-}$ is mesylate, where m is 1. The mesylate (MSA) salt (also referred to herein as compound 1A, shown below) can be obtained via a process as disclosed in WO2016/024858A1 or in WO2007/116922A1, the disclosures of which are incorporated herein by reference in their entirety.

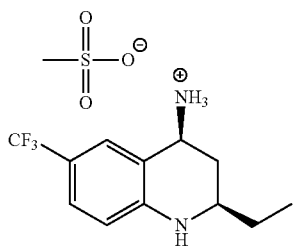

1A

In some embodiments, the desalting of a compound of Formula (IIA) or (IIB) in step (pre-a2) is performed in a mixture of an aqueous sodium hydroxide solution and an organic solvent chosen from toluene, dichloromethane, cyclopentyl methyl ether, isopropyl ether, t-butyl methyl ether, ethyl acetate, isopropyl acetate, methyl ethyl ketone, methyl isobutyl ketone, chlorobenzene and combinations thereof, followed by heating the mixture then cooling the mixture, and allowing the system to phase separate, and separating off the aqueous phase. In some embodiments, the solvent is toluene. In some embodiments the reaction mixture is heated to a temperature between 45° C. and 60° C., then cooled to a temperature between 15° C. and 40° C.

In some embodiments, the organic phase obtained after separating off the aqueous phase is subjected to one or more aqueous washing steps wherein each aqueous washing step is followed by separating off the aqueous phase, such as one or more washing steps with an aqueous sodium chloride solution, followed by separating off the aqueous phase, and subsequently one or more washing steps with deionized water, again followed by separating off the aqueous phase. The resulting washed organic phase is then optionally subjected to distillation to reduce the water content to below 1000 ppm, based on the weight of the solution. Alternatively, in some embodiments, a small amount of water remains in the organic phase with the compound of Formula (II) and the subsequent coupling with a compound of Formula (III) proceeds in the presence of this small amount of water.

In some embodiments the desalting reaction in step (pre-2a) is performed on the mesylate salt (Compound 1A) in a mixture of an aqueous sodium hydroxide solution and toluene, at a temperature between 45° C. and 60° C., followed by cooling the mixture to a temperature between 15° C. and 25° C., allowing the system to phase separate, and separating off the aqueous phase. The toluene phase obtained after separating off the aqueous phase is then optionally subjected to one or more washing steps with an aqueous sodium chloride solution, followed by separating off the aqueous phase, and subsequently one or more washing steps with deionized water, again followed by separating off the aqueous phase, after which the resulting washed toluene phase is subjected to distillation at a temperature between 50° C. and 65° C. under reduced pressure to reduce the water content to below 1000 ppm, based on the weight of the total amount of the solution. Alternatively, a small amount of water remains in the toluene with the compound of Formula (II) and the subsequent coupling reaction with a compound of Formula (III) proceeds in the presence of this small amount of water.

As outlined above, in step (a) the compound of Formula (II), or a salt thereof (e.g., compound of Formula (IIA) or (IIB), such as the mesylate salt 1A), is coupled with a compound of Formula (III) to provide a compound of Formula (IV). In some embodiments, this process is carried out in an organic solvent.

The coupling partner of Formula (III) in step (a) includes a leaving group ($X^1$). It will be understood that any convenient leaving group may find use in the present disclosure for X. In some embodiments, the leaving group ($X^1$) in the compound of Formula (III) is selected from a halogen, a carbamate, and a substituted sulfonyloxy group. In some embodiments, the leaving group ($X^1$) in the compound of Formula (III) is a sulfonyloxy group selected from a methanesulfonyloxy, p-toluenesulfonyloxy or a trifluoromethanesulfonyloxy group. In some embodiments, the leaving group ($X^1$) is a carbamate. In some embodiments, the leaving group ($X^1$) is a halogen. In certain embodiments, the halogen is chloride. The coupling partner of Formula (III) in step (a) also includes a protecting group ($Y^1$). The term "protecting group" refers to any group which when bound to a functional group such as a carboxylic acid moiety of the compounds (including intermediates thereof) prevents reactions from occurring at the functional group and which protecting group can be removed by conventional chemical or enzymatic steps to reestablish the functional group e.g., the carboxylic acid moiety. The particular removable protecting group employed is not critical and examples of carboxylic acid protecting groups include conventional substituents such as t-butyl esters, methyl esters, ethyl esters, benzyl esters, allyl esters, 1,1-diethylallyl esters, 2,2,2-trifluro ethyl esters, phenyl esters, 4-methoxybenzyl esters, silyl esters, ortho esters, esters of 2,6-disubstituted phenols (e.g., 2,6-dimethylphenol) and any other groups that can be introduced chemically onto a carboxylic acid group or like functionality and later selectively removed either by chemical or enzymatic methods in mild conditions compatible with the nature of the product. It will be understood that any convenient protecting group (e.g., ester group) for a carboxylic acid moiety may find use in the present disclosure for $Y^1$, and the selection of appropriate protecting groups can be readily determined by one skilled in the art. Suitable groups for that purpose are discussed in standard textbooks in the field of chemistry, such as Protective Groups in Organic Synthesis, 4th Ed., by T. W. Greene and P. G. M. Wuts (John Wiley & Sons, New York, 1999), in Protecting Group Chemistry, 1st Ed., by Jeremy Robertson (Oxford University Press, 2000); and in March's Advanced Organic chemistry: Reactions Mechanisms, and Structure, 8th Ed., by Michael B. Smith (Wiley-Interscience Publication, 2001). In some embodiments, the protecting group ($Y^1$) is selected from an alkyl group, a substituted alkyl group, an aryl group, a substituted aryl group, an allyl group, a substituted allyl group, and a silyl group. In some embodiments, the protecting group ($Y^1$) is selected from t-butyl, methyl, ethyl, benzyl, allyl, substituted allyl, 2,2,2-trifluro ethyl, phenyl, 4-methoxybenzyl ester, a 2,6-disubstituted phenol, and a silyl group. In some embodiments, the protecting group ($Y^1$) is a t-butyl group. In some embodiments, the compound of Formula (III) is of the structure 1B below:

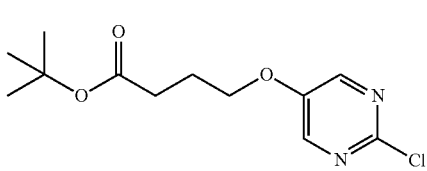

1B

In some embodiments of the coupling reaction of step (a), the solvent is selected from toluene, t-butanol, 1,4-dioxane, xylene, N-methyl-2-pyrrolidone, dimethylformamide, water, tetrahydrofuran, and combinations thereof. In some embodiments, the solvent is a mixture of organic solvent toluene and organic co-solvent t-butanol.

If steps (pre-a1) and (pre-a2) are performed before step (a), the compound of Formula (II) is already present in the required solvent, because the same organic solvents are used in steps (pre-a2) and (a) or because of a solvent swap in step (pre-a2). If need be, more organic solvent and for example an organic co-solvent can be added in step (a). As will be appreciated by the skilled person, an organic co-solvent can also be added during a solvent swap in step (pre-a2). In some embodiments, steps (pre-a1) and (pre-a2) are performed before step (a) and the compound of Formula (II) is present in toluene.

The coupling reaction in step (a) typically is a catalyzed reaction. In some embodiments, the reaction is a palladium-catalyzed coupling reaction in the presence of a base. Suitable examples of palladium catalysts are for example tris(dibenzylideneacetone)dipalladium and Pd(II)acetate. Suitable bases include organic bases (e.g., sodium t-butoxide, and potassium t-butoxide) and inorganic bases (e.g., $K_3PO_4$, $K_3PO_4 \cdot H_2O$, sodium carbonate, potassium carbonate, cesium carbonate, LiHMDS, NaHMDS, KOH, and NaOH).

In many embodiments, anhydrous $K_3PO_4$ is used as a base. In many such embodiments, the particle size distribution is such that 90% of the particles are smaller than between about 140 and about 307 microns including between about 140 and about 170 microns, including about 160 and about 290 microns, and about 180 and about 220 microns, and about 200 and about 210 microns. In some embodiments, 90% of the particles are less than 205 microns.

In these and other embodiments, 50% of the particles are between about 35 and about 173 microns or smaller, including between about 35 and about 40 microns.

In these and other embodiments, 10% of the particles between about 7 and about 74 microns including between about 7 and about 10 microns.

In some embodiments, the compound of Formula (II) is reacted in step (a) with a compound of Formula (III) in a solvent (e.g., an organic solvent), using a palladium catalyst, a base. In some embodiments, the reaction mixture further includes a ligand.

In some embodiments, the compound of Formula (IIA) or (IIB) is reacted in step (a) with a compound of Formula (III) in a solvent (e.g., an organic solvent), using a palladium catalyst, a base. In some embodiments, the reaction mixture further includes a ligand.

In some embodiments, the desalted compound of Formula (II) is reacted in step (a) with a compound of Formula (III) in the solvent (e.g., an organic solvent), using Pd(II)acetate, either (S)-BINAP [(S)-2,2'-bis(diphenylphosphino)-1,1'-binaphthyl] or rac-BINAP as a ligand. In some embodiments, (S)-BINAP is used as the ligand, and a base selected from sodium t-butoxide, potassium t-butoxide, anhydrous $K_3PO_4$, $K_3PO_4 \cdot H_2O$, sodium carbonate, potassium carbonate, cesium carbonate, LiHMDS, NaHMDS, KOH and NaOH.

In some embodiments, a salt of Formula (IIA) or (IIB) is reacted in step (a) with a compound of Formula (III) in the solvent (e.g., an organic solvent), using Pd(II)acetate, either (S)-BINAP [(S)-2,2'-bis(diphenylphosphino)-1,1'-binaphthyl], (R)-BINAP [(S)-2,2'-bis(diphenylphosphino)-1,1'-binaphthyl], or rac-BINAP as a ligand. In some embodiments, (S)-BINAP is used as the ligand, and a base selected from sodium t-butoxide, potassium t-butoxide, anhydrous $K_3PO_4$, $K_3PO_4 \cdot H_2O$, sodium carbonate, potassium carbonate, cesium carbonate, LiHMDS, NaHMDS, KOH and NaOH. In some embodiments, the salt of Formula (IIA) is the mesylate salt, Compound 1A.

In some embodiments, the reaction in step (a) is performed at a temperature from 70° C. and 80° C., optionally under a nitrogen atmosphere, for 2 or more hours.

In some embodiments, the compound of Formula (II) or salt of Formula (IIA) is reacted in step (a) with a compound of Formula (III) wherein $X^1$ is Cl and $Y^1$ is t-butyl, in a mixture of organic solvent toluene and organic co-solvent t-butanol, using Pd(II)acetate as catalyst, (S)-BINAP as a ligand, and anhydrous $K_3PO_4$ or $K_3PO_4 \cdot H_2O$ as a base, at a temperature between 70° C. and 80° C., under a nitrogen atmosphere, for 2 or more hours.

In some embodiments, the one or more aqueous washing steps comprise one or more washing steps with water, preferably deionized water, followed by separating off the aqueous phase, subsequently one or more washing steps with an aqueous HCl solution, followed by separating off the aqueous phase, subsequently one or more washing steps with an aqueous sodium chloride solution, followed by separating off the aqueous phase, and finally one or more washing steps with again deionized water, followed by separating off the aqueous phase.

If t-butanol is used as an organic co-solvent in step (a), this organic co-solvent is removed from the organic phase during the washing steps.

If step (a) is performed in an organic solvent different from the solvent used in step (b), the organic solvent used in step (a) is swapped in step (a) with the organic solvent applied in step (b), such that the compound of Formula (IV) remains in solution.

In some embodiments wherein the (organic) solvents used in steps (a) and (b) are different, at least part of the (organic) solvent used in step (a) is evaporated, such as by using distillation at reduced pressure, and the organic solvent of step (b) is added, such that the compound of Formula (IV) remains in solution during the solvent swap. This process can be performed by continuously evaporating the (organic)

solvent used in step (a) and by continuously adding the organic solvent of step (b), for example until the amount of the (organic) solvent used in step (a), based on the total amount of solvent, is below a certain threshold value. Alternatively, this process can be performed batch-wise in more than one steps of evaporating part of the (organic) solvent used in step (a) and subsequently adding part of the organic solvent used in step (b), for example until the amount of the (organic) solvent used in step (a), based on the total amount of solvent, is below a certain threshold value.

In some embodiments, the solvent used in step (a) is a mixture of organic solvent toluene and organic co-solvent t-butanol. The t-butanol is removed from the organic phase comprising the compound of Formula (IV) during the washing steps.

In some embodiments of step (a), the remaining organic solvent toluene is swapped with acetonitrile by distilling off in two or more steps, at a temperature between 50° C. and 65° C. under reduced pressure, part of the toluene with intermediate addition of acetonitrile, in an amount to obtain a solvent mixture with less than about 20 weight percent toluene, based on the combined weight of the solvents, such that the compound of Formula (IV) remains in solution. In some embodiments of the compound of Formula (IV), $Y^1$ is t-butyl.

Method of Preparing Obicetrapib—Step (b) from Aspects (a)-(d)

In step (b) of the method for preparing a compound of Formula (I) according to the disclosure, the compound of Formula (IV) is converted to the carbamate of Formula (V) in an organic solvent, and subsequently isolated as a solid salt of Formula (VI) (where $Y^1$ is a protecting group, e.g., as described herein).

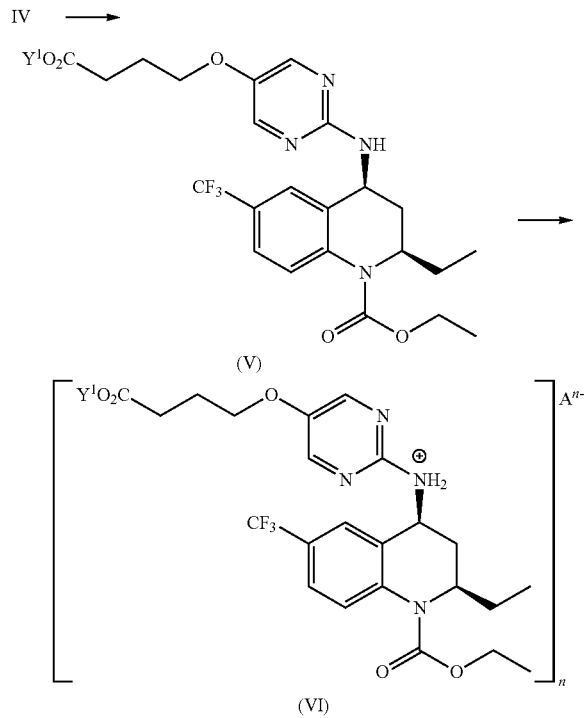

In some embodiments, the organic solvent used in step (b) is selected from acetonitrile, chlorobenzene, toluene, N-methyl-2-pyrrolidone, xylene, 1,4-dioxane, ethyl acetate, isopropyl acetate, methyl ethyl ketone, methyl isobutyl ketone, dichloromethane, t-butyl methyl ether, and combinations thereof. In some embodiments, the organic solvent is acetonitrile or a mixture of chlorobenzene and dichloromethane.

As explained hereinbefore, the compound of Formula (IV) is already provided in step (a) in the organic solvent used in step (b), either because the same organic solvents are used in steps (a) and (b) or because of a solvent swap in step (a). In some embodiments of the compounds of Formulae (IV), (V) and (VI), $Y^1$ is t-butyl.

In some embodiments, the organic solvent used in step (b) is a mixture of acetonitrile toluene, with less than about 20 weight percent toluene, based on the combined weight of the organic solvents.

In some embodiments, the conversion of the compound of Formula (IV) to the corresponding carbamate with Formula (V) in step (b) is performed in acetonitrile with less than about 20 weight percent toluene, based on the combined weight of the organic solvents, with an excess ethyl chloroformate in the presence of pyridine, at a temperature between 10° C. and 20° C.

If step (b) is performed in an organic solvent different from the organic solvent used in step (c), the organic solvent used in step (b) is swapped in step (b) with the organic solvent applied in step (c), such that the compound of Formula (V) remains in solution.

In some embodiments where the organic solvents used in steps (b) and (c) are different, at least part of the organic solvent used in step (b) is evaporated, such as by distillation at reduced pressure, and the organic solvent of step (c) is added, such that the compound of Formula (V) remains in solution during the organic solvent swap. This process can be performed by continuously evaporating the organic solvent used in step (b) and by continuously adding the organic solvent of step (c), for example until the amount of the organic solvent used in step (b), based on the total amount of organic solvent, is below a certain threshold value. Alternatively, this process can be performed batch-wise in more than one steps of evaporating part of the organic solvent used in step (b) and subsequently adding part of the organic solvent used in step (c), for example until the amount of the organic solvent used in step (b), based on the total amount of organic solvent, is below a certain threshold value.

The resulting mixture is preferably subjected to one or more treatments with an aqueous sodium chloride and/or HCl solution, followed by separating off the aqueous phase, and subsequently to one or more treatments with an aqueous bicarbonate solution, followed by separating off the aqueous phase.

In some embodiments, the conversion of the compound of Formula (IV) to the corresponding carbamate with Formula (V) in step (b) is performed in acetonitrile with an excess of ethyl chloroformate in the presence of pyridine, at a temperature between 10° C. and 20° C., and this solvent is swapped in step (b) with isopropyl acetate by distilling off in two or more steps, at a temperature of 60° C. or less under reduced pressure, part of the acetonitrile with intermediate addition of isopropyl acetate, in an amount to obtain a solution of the compound of Formula (V) in isopropyl acetate, wherein the solution may be subjected to one or more treatments with an aqueous NaCl/HCl solution, followed by separating off the aqueous phase, and subsequently to one or more treatments with an aqueous bicarbonate solution, followed by separating off the aqueous phase.

Next, the compound of Formula (V) dissolved in an organic solvent is converted to a corresponding salt according to Formula (VI), wherein $A^{n-}$ is an anion and n is an integer from 1-3. The solid form of the salt according to Formula (VI) is then isolated as a solid form.

In some embodiments, the salt of Formula (VI) is chosen from salts with an anion $A^{n-}$ selected from a sulfonate (e.g., besylate, tosylate, napsylate, camsylate, esylate, edisylate and mesylate), a sulfate (e.g., methylsulfate), a halogen, acetate, aspartate, benzoate, bicarbonate, bitartrate, carbonate, citrate, decanoate, fumarate, gluceptate, gluconate, glutamate, glycolate, hexanoate, hydroxynaphthoate, isethionate, lactate, lactobionate, malate, maleate, mandelate, mucate, nitrate, octanoate, oleate, pamoate, pantothenate, phosphate, polygalacturonate, propionate, salicylate, stearate, succinate, tartrate, and teoclate.

In some embodiments, the salt of Formula (VI) is chosen from salts with an anion $A^{n-}$ selected from chloride, bromide, bitartrate, a sulfate, and a sulfonate.

In some embodiments, the salt of Formula (VI) is chosen from salt with an anion $A^{n-}$ selected from chloride, bromide, bitartrate, and mesylate.

In some embodiments, the salt from of Formula (VI) is the mesylate salt including the crystalline mesylate salt thereof, Compound 1D:

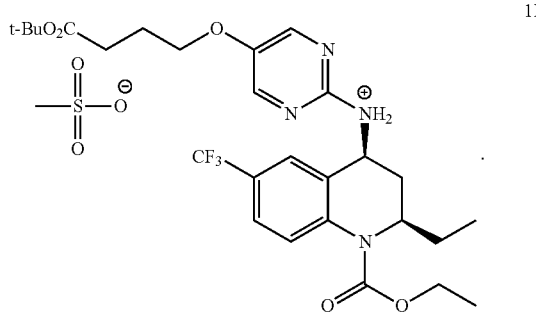

In some embodiments, of the salt of Formula (VI), n is 1.

The organic solvent used in the conversion of Formula (V) to (VI) is not particularly limited, but in some embodiments is selected from cyclopentyl methyl ether, isopropyl ether, t-butyl methyl ether, ethyl acetate, isopropyl acetate, and combinations thereof. In some embodiments, isopropyl acetate or a mixture comprising dichloromethane, n-heptane and isopropyl alcohol, such as a mixture of chlorobenzene, dichloromethane, n-heptane and isopropyl alcohol is used. It is noted that, the compound of Formula (V) is already provided in organic solvent owing to the solvent swap described herein before.

Accordingly, in some embodiments, the organic solvent used in the conversion of compound of Formula (V) to its corresponding salt of Formula (VI) selected from cyclopentyl methyl ether, isopropyl ether, t-butyl methyl ether, ethyl acetate, isopropyl acetate, and combinations thereof, with less than about 20 weight percent toluene and less than about 7 weight percent acetonitrile, based on the combined weight of the solvents. In some embodiments, the solvent is a mixture of isopropyl acetate, toluene and acetonitrile, with less than about 20 weight percent toluene and less than about 7 weight percent acetonitrile, based on the combined weight of the solvents.

In some embodiments, it is preferred to add an organic co-solvent different from the organic solvent already used in step (b). Exemplary organic co-solvents are selected from cyclopentyl methyl ether, isopropyl ether, t-butyl methyl ether, ethyl acetate, isopropyl acetate, and combinations thereof, such as methyl t-butyl ether. As will be appreciated by the skilled person, the need and advantages of using an organic co-solvent depend on the particular organic solvent already used in step (b). In certain cases, the use of a co-solvent can be dispensed with.

In some embodiments, the organic solvent for the conversion of a compound of Formula (V) to its corresponding salt of Formula (VI) comprises isopropyl acetate and methyl t-butyl ether as an organic co-solvent.

Subsequently, an acid is added to form the salts of Formula (VI) defined supra. In some embodiments the acid is selected from ditartartic acid, sulfuric acids, sulfonic acids, hydrogen bromide and hydrogen chloride. In some embodiments, the acid is methanesulfonic acid. In embodiments wherein the salt of Formula (VI) can be obtained in crystalline form, part of the acid needed to form the salt of Formula (VI) can be added before the crystallization and part during the crystallization.

The solid form of the salt of Formula (VI) is isolated by crystallization if the salt of Formula (VI) can be obtained in crystalline form, filtration, one or more optional washing steps of the filtration residue, and drying.

In some embodiments, the compound of Formula (V) is converted to the corresponding mesylate salt according to Formula (VI) with methanesulfonic acid in an organic solvent mixture of isopropyl acetate and methyl t-butyl ether with less than about 20 weight percent toluene and less than 7 weight percent acetonitrile, based on the combined weight of the organic solvents, followed by crystallizing the mesylate salt according to Compound 1D from the organic solvent, with subsequent filtration, one or more optional washing steps of the filtration residue, and drying.

In some embodiments wherein the salt according to Formula (VI) can be obtained in crystalline form, crystallization is induced by adding seed crystals of the salt according to Formula (VI).

In some embodiments, wherein the salt according to Formula (VI) can be obtained in crystalline form, crystallizing the salt according to Formula (VI) and obtaining the crystalline form of the salt according to Formula (VI) is performed by adding the acid needed to form the salts, by agitating the resulting mixture for more than 60 minutes at a temperature from 20° C. to 25° C., by allowing crystallization under agitation at a temperature between 15° C. and 25° C. for more than 120 minutes, followed by subjecting the resulting slurry to vacuum filtration, wherein the filtration residue is washed one or more times with the same organic solvent that is used to crystallize the salt according to Formula (VI) from, and by vacuum drying the crystalline form of the salt according to Formula (VI).

In an embodiment, the invention concerns the salt according to Formula (VI), wherein $A^{n-}$ is an anion, wherein n is an integer from 1-3. In some embodiments, the compound is the crystalline mesylate (MSA) salt of Formula (VI) (e.g., Compound 1D as described herein).

In some embodiments, crystallizing the mesylate salt of Formula (VI) from an organic solvent mixture of isopropyl acetate and methyl t-butyl ether and obtaining the crystalline form of the mesylate salt according to Compound 1D is performed by adding methanesulfonic acid needed to form the salt, agitating the resulting mixture for more than 60 minutes at a temperature between 15° C. and 25° C. (e.g., 20° C.), then allowing crystallization under agitation at a temperature between 15° C. and 25° C. for more than 120 minutes. The resulting slurry is subjected to vacuum filtration, wherein the filtration residue is washed one or more times with a mixture of isopropyl acetate and methyl t-butyl ether, and dried under vacuum to provide a crystalline form of the mesylate salt according to Compound 1D.

In some embodiments, the compound of Formula (VI) is obtained in a yield of at least 70%, based on the number of moles of the compound of Formula (II). In some embodiments, the compound of Formula (VI) is obtained with a purity of 99% or more, such as a purity of 99.1% or more, 99.2% or more, 99.3% or more, 99.5% or more, or even more.

Method of Preparing Obicetrapib—Step (c) from Aspects (a)-(d)

In step (c) of the process according to the present disclosure, the isolated salt of Formula (VI), or the desalted derivative thereof (e.g., the compound according to Formula (V)), is alkylated with a compound of Formula (VII) to provide a compound of Formula (VIII):

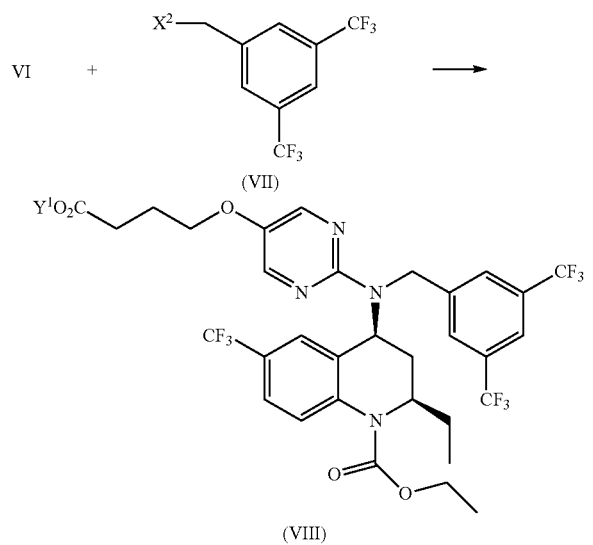

where, $X^2$ is a leaving group and $Y^1$ is a protecting group (e.g., as described herein).

In some embodiments of step (c), the isolated solid form of the salt according to Formula (VI), such as a crystalline form of the salt according to Formula (VI) (such as the crystalline mesylate salt, Compound 1D), is reacted directly with a compound of Formula (VII) in an organic solvent, to form a compound of Formula (VIII) (i.e., without a desalting step).

In some embodiments of step (c), the isolated solid form of the salt according to Formula (VI), such as a crystalline form of the salt according to Formula (VI) (such as the crystalline mesylate salt, Compound 1D), is desalted and reacted with a compound of Formula (VII) in an organic solvent, to form a compound of Formula (VIII). Desalting the compound of Formula (VI) results in a compound according to Formula (V).

When the compound of Formula (VI) is subjected to a desalting step, the desalting process and the subsequent reaction with a compound of Formula (V) are performed in the same organic solvent. In some embodiments, the organic solvent is selected from xylene, n-hexane, toluene, heptanes (mix of isomers), n-heptane, dichloromethane, chlorobenzene, and combinations thereof. In some embodiments, the organic solvent is toluene or n-heptane.

In some embodiments, step (c) is carried out in the presence of a base. In some embodiments, step (c) is carried out in the presence of a solid-liquid phase-transfer catalyst.

In some embodiments, the base is selected from alkali metal hydrides, alkali metal hydroxides, alkali earth metal hydroxides, alkali metal alkoxides, alkali metal carbonates, alkali metal bicarbonates and amines. In some embodiments, the base is chosen from alkali metal alkoxides. In some embodiments, the base is sodium t-pentoxide or a mixture of sodium t-butoxide, and potassium t-butoxide.

In some embodiments, the solid-liquid phase-transfer catalyst is selected from t-butylammonium hydrogensulfate, tetra-n-butylammonium bromide, tetra-n-butylammonium iodide, a crown ether, and combinations thereof. In some embodiments, the catalyst is t-butylammonium hydrogensulfate.

In some embodiments, the reaction of the compound of Formula (V) or (VI) with the compound of Formula (VII) is performed at a temperature between 0° C. and 25° C. (such as from 5° C. to 20° C.).

The coupling partner of Formula (VII) in step (c) includes a leaving group $X^2$. It will be understood that any convenient leaving group may find use in the present disclosure for $X^2$. In some embodiments, the leaving group $X^2$ in the compound of Formula (VII) is selected from a halogen, and a substituted sulfonyloxy group. In some embodiments, the leaving group $X^2$ in the compound of Formula (VII) is a substituted sulfonyloxy group selected from a methanesulfonyloxy, p-toluenesulfonyloxy or a trifluoromethanesulfonyloxy group. In some embodiments, the leaving group $X^2$ is a halogen. In certain embodiments, the halogen is bromide. In some embodiments, the compound of Formula (VII) is of the structure 1E below.

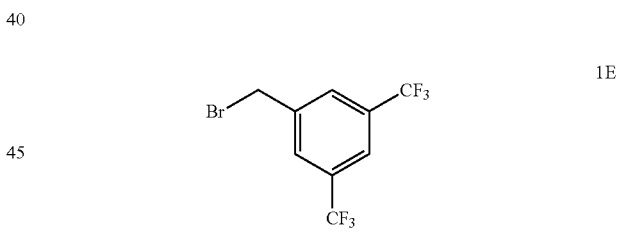

In some embodiments, the desalting of the compound of Formula (VI) and the subsequent reaction with a compound of Formula (VII) in step (c) is performed in toluene as an organic solvent in the presence of a base and a catalyst at a temperature from 5° C. to 25° C. In some embodiments, the desalting of the compound of Formula (VI) and the subsequent reaction with a compound of Formula (VII) in step (c) is performed in toluene as an organic solvent in the presence of sodium t-pentoxide as a base and t-butylammonium hydrogensulfate as a catalyst at a temperature between 5° C. and 25° C. under agitation for about 1 to 8 hours. In some embodiments of the compound of Formula (VI), $Y^1$ is t-butyl.

In some embodiments, the alkylation of a compound of Formula (VI) (i.e., without an additional desalting step) with a compound of Formula (VII) in step (c) is performed in toluene as an organic solvent in the presence of a base and a catalyst at a temperature from 5° C. to 25° C.

In some embodiments, the alkylation of a compound of Formula (VI) with a compound of Formula (VII) in step (c) is performed in toluene as an organic solvent in the presence of sodium t-pentoxide as a base and t-butylammonium hydrogensulfate as a catalyst at a temperature between 5° C. and 25° C. under agitation for about 1 to 8 hours.

In some embodiments, step (c) includes providing crystalline 1D, desalting this compound and reacting the desalted compound with a compound of Formula (VII) wherein $X^2$ is Br in toluene as an organic solvent in the presence of sodium t-pentoxide as a base and t-butylammonium hydrogensulfate as a catalyst, at a temperature between 5° C. and 25° C. under agitation for about 1 to 8 hours.

In some embodiments, step (c) includes reacting crystalline 1D with a compound of Formula (VII) wherein $X^2$ is Br in toluene as an organic solvent in the presence of sodium t-pentoxide as a base and t-butylammonium hydrogensulfate as a catalyst, at a temperature between 5° C. and 25° C. under agitation for about 1 to 8 hours.

In some embodiments of step (c), the base is the last reagent added to the reaction mixture. Without being bound to any particular theory, the inventors have discovered that by adding the base as the last reagent, the number of equivalents of both the base and the compound of Formula (VII) used in the reaction mixture can be reduced. A reduction in the number of equivalents of the compound of Formula (VII) can in turn reduce the risk of carryover of Formula (VII) related impurities to the final product.

Accordingly, step (c) results in the production of a compound of Formula (VIII) in an organic solvent. In some embodiments of the compound of Formula (VIII), $Y^1$ is t-butyl. In some embodiments, this reaction mixture is subjected in step (c) to one or more aqueous washing steps to remove impurities, followed by separating off the aqueous phase, and optionally one or more filtration steps, to obtain a washed reaction mixture comprising the compound of Formula (VIII) in the organic solvent. In some embodiments, the reaction mixture comprising the compound of Formula (VIII) in the organic solvent is concentrated by distilling off part of the organic phase to obtain a concentrated reaction mixture comprising the compound of Formula (VIII) in the organic solvent. In some embodiments, the organic solvent comprises from 30 to 40 weight percent of the compound of Formula (VIII) based on the weight of the reaction mixture. In some embodiments, the organic solvent comprises 34 to 37 weight percent of the compound of Formula (VIII) based on the weight of the reaction mixture.

The one or more aqueous washing steps, the optionally one or more filtration steps, and the concentration step are preferably combined such that a washed and concentrated reaction mixture comprising the compound of Formula (VIII) in the organic solvent is obtained. In some cases, the organic solvent includes from 30 to 40 weight percent of the compound of Formula (VIII). In some embodiments, the organic solvent includes from 34 to 37 weight percent of the compound of Formula (VIII) based on the weight of the reaction mixture.

In some embodiments, the one or more aqueous washing steps comprise one or more washing steps with an aqueous acetic acid solution.

In some embodiments, the reaction mixture comprising the compound of Formula (VIII) in toluene as an organic solvent is subjected in step (c) to one or more aqueous washing steps with an aqueous acetic acid solution followed by separating off the aqueous phase, and subsequently by distilling off part of the toluene, typically at a temperature from 75° C. to 90° C. under reduced pressure, to obtain a washed and concentrated reaction mixture comprising the compound of Formula (VIII) in toluene with from 30 to 40 weight percent of the compound of Formula (VIII) based on the weight of the reaction mixture. In some embodiments, the concentrated mixture includes from 34 to 37 weight percent of the compound of Formula (VIII) based on the weight of the reaction mixture.

If step (c) is performed in an organic solvent different from the organic solvent used in step (d), the organic solvent used in step (c) is swapped in step (c) with the organic solvent applied in step (d) such that the compound of Formula (VIII) remains in solution.

In some embodiments, wherein the organic solvents used in steps (c) and (d) are different, at least part of the organic solvent used in step (c) is evaporated, preferably using distillation at reduced pressure, and the organic solvent of step (d) is added, such that the compound of Formula (VIII) remains in solution during the organic solvent swap. This process can be performed by continuously evaporating the organic solvent used in step (c) and by continuously adding the organic solvent of step (d), for example until the amount of the organic solvent used in step (c), based on the total amount of organic solvent, is below a certain threshold value. Alternatively, this process can be performed batch-wise in more than one steps of evaporating part of the organic solvent used in step (c) and subsequently adding part of the organic solvent used in step (d), for example until the amount of the organic solvent used in step (c), based on the total amount of organic solvent, is below a certain threshold value.

Method of Preparing a Compound of Formula (I)—Step (d) from Aspects (a)-(d)

In step (d) of the process according to the present disclosure, the compound of Formula (VIII) is converted to obicetrapib in a first organic solvent (where $Y^1$ is a protecting group, e.g., as described herein).

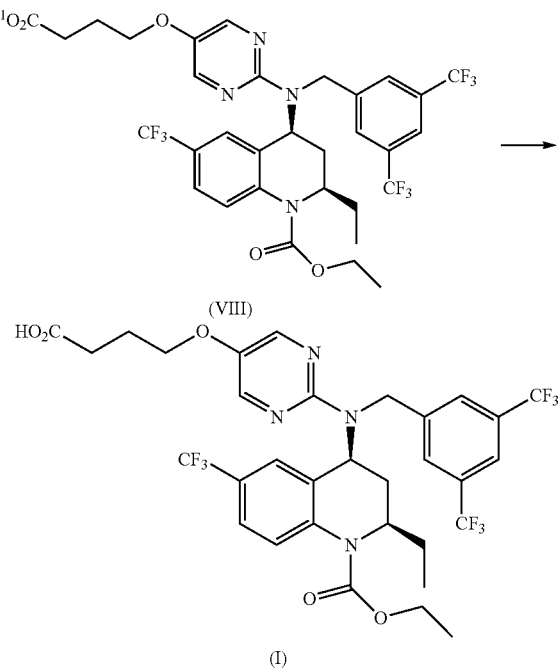

The selection of the first organic solvent used in step (d) is not particularly limited. In some embodiments, the first organic solvent is not an ether or an ester. In some embodiments, the first organic solvent is toluene or a mixture of n-heptane and acetic acid. As explained hereinbefore, the compound of Formula (VIII) is already provided in step (c) in the first solvent used in step (d), either because the same organic solvents are used in steps (c) and (d) or because of a solvent swap in step (c).

Accordingly, in some embodiments, the first organic solvent as defined hereinbefore with from 30 to 40 weight percent of the compound of Formula (VIII), such as from 34 to 37 weight percent, based on the weight of the reaction mixture, is provided in step (d).

In some embodiments, toluene as a first organic solvent with from 30 to 40 weight percent of the compound of Formula (VIII), such as from 34 to 37 weight percent, based on the weight of the reaction mixture, is provided in step (d).

Any convenient protecting group for a carboxylic acid, such as an ester moiety, may find use as $Y^1$ in the compound of Formula (VIII). As disclosed herein, the selection of an appropriate protecting group for a carboxylic acid can be readily determined by one skilled in the art. In some embodiments of Formula (VIII), the protecting group ($Y^1$) is selected from an alkyl group, a substituted alkyl group, an aryl group, a substituted aryl group, an allyl group, a substituted allyl group, and a silyl group. In some embodiments of Formula (VIII), the protecting group ($Y^1$) is selected from t-butyl, methyl, ethyl, benzyl, allyl, substituted allyl, 2,2,2-trifluro ethyl, phenyl, 4-methoxybenzyl ester, a 2,6-disubstituted phenol, and a silyl group. In some embodiments of the compound of Formula (VIII), the protecting group $Y^1$ is t-butyl. In some embodiments, the conversion of the compound of Formula (VIII) to obicetrapib is performed by contacting the compound of Formula (VIII) in the first organic solvent, such as toluene or a mixture of n-heptane and acetic acid, with acetic acid (AcOH) and dry HCl under agitation. In some embodiments, the reaction mixture is heated to a temperature between 40° C. and 55° C. and the resulting mixture is maintained at this temperature under agitation for at least 3 hours.

Obicetrapib can be isolated from the resulting mixture using techniques known to the skilled person.

In some embodiments, the resulting mixture comprising obicetrapib, is subjected in step (d) to one or more aqueous washing steps. In some embodiments, the one or more aqueous washing steps in step (d) are performed as follows:

(AA) the reaction mixture comprising obicetrapib is cooled to a temperature between 15° C. and 25° C., and subsequently a mixture of n-heptane, acetonitrile and water is added followed by agitating the resulting mixture for more than 15 minutes at this temperature;

(BB) the system obtained in step (AA) is allowed to phase separate into an organic phase and an aqueous phase and both phases are separated;

(CC) a mixture of n-heptane, acetonitrile, toluene and water is added to the aqueous phase obtained in step (BB), followed by agitating the resulting system for more than 15 minutes at a temperature between 15° C. and 25° C.;

(DD) the system obtained in step (CC) is allowed to phase separate into an organic phase and an aqueous phase and both phases are separated;

(EE) the organic phase obtained in step (BB) and the organic phase obtained in step (DD) are combined, water is added, and the resulting system is agitated for more than 15 minutes at a temperature between 15° C. and 25° C.;

(FF) the system obtained in step (EE) is allowed to phase separate into an organic phase and an aqueous phase and both phases are separated;

(GG) water is added to the organic phase obtained in step (FF) and the resulting system is agitated for more than 15 minutes at a temperature between 15° C. and 25° C.;

(HH) the system obtained in step (GG) is allowed to phase separate into an organic phase and an aqueous phase and both phases are separated;

(II) an aqueous solution of sodium citrate tribasic dihydrate is added to the organic phase obtained in step (HH) followed by agitating the resulting mixture for more than 15 minutes at a temperature between 15° C. and 25° C.;

(JJ) the system obtained in step (II) is allowed to phase separate into an organic phase and an aqueous phase and both phases are separated;

(KK) water is added to the organic phase obtained in step (JJ) and the resulting system is agitated for more than 15 minutes at a temperature between 15° C. and 25° C.; and (LL) the system obtained in step (KK) is allowed to phase separate into an organic phase and an aqueous phase and both phases are separated.

Steps (AA) to (LL) in this embodiment result in a washed compound of Formula (I) in an organic solvent mixture comprising n-heptane, acetonitrile and the first organic solvent. In some embodiments the first solvent is toluene.

In some embodiments, wherein the first organic solvent does not already mainly consist of cyclopentyl methyl ether, the organic solvent mixture is swapped in a subsequent step (MM) with CPME such that obicetrapib remains in solution.

Hence, in some embodiments, step (LL) is followed by step (MM) wherein at least part of the solvents in the organic solvent mixture obtained in step (LL) is evaporated, such as by distillation at reduced pressure, and wherein cyclopentyl methyl ether is added, such that obicetrapib remains in solution during the solvent swap. In some embodiments, the process results in a solution of obicetrapib in cyclopentyl methyl ether with a concentration between 30 and 40 weight percent based on the weight of the solution. In some embodiments, the concentration of obicetrapib in cyclopentyl methyl ether is from 33 and 37 weight percent, based on the weight of the solution, less than 1 weight percent of the first organic solvent, and less than 1 weight percent of n-heptane based on the weight of the solution.

This process can be performed by continuously evaporating the solvents in the organic solvent mixture obtained in step (LL) and by continuously adding cyclopentyl methyl ether, for example until the amount of specific solvents in the organic solvent mixture, based on the total amount of organic solvents, is below a certain threshold value. Alternatively, this process can be performed batch-wise in more than one steps of evaporating part of the solvents in the organic solvent mixture obtained in step (LL) and by subsequently adding cyclopentyl methyl ether, for example until the amount of specific solvents in the organic solvent mixture, based on the total amount of solvent, is below a certain threshold value.

In some embodiments, the first organic solvent is toluene, step (LL) is followed by step (MM) wherein at least part of the n-heptane, acetonitrile and toluene in the organic solvent mixture obtained in step (LL) is evaporated, such as by distillation at a temperature of 45° C. or lower and at reduced pressure (in-vacuo), with intermediate additions of cyclopentyl methyl ether, such that obicetrapib remains in solution during the solvent swap, resulting in a solution of obicetrapib in cyclopentyl methyl ether with a concentration between 30 and 40 weight percent. In some embodiments, the concentration of obicetrapib in cyclopentyl methyl is from 33 to 37 weight percent based on the weight of the solution, with less than 0.5 weight percent of toluene, less than 0.5 weight percent of acetonitrile and less than 2.7 weight percent of n-heptane.

Method of Preparing a Crystalline Obicetrapib HCl-Steps (e)-(f) in Addition to Aspects (a)-(d)

In some embodiments of the subject method, step (d) is followed by step (e)-(f), wherein obicetrapib is treated with HCl such as in a suitable solvent. Such solvent may be an aqueous solvent or an organic solvent. In some embodiments, the use of an organic solvent provides crystalline obicetrapib HCl.

In some embodiments, the organic solvent used in step (e) comprises a mixture of a solvent and an anti-solvent. In some embodiments, the solvent is selected from methanol, ethanol, isopropanol, acetic acid, acetonitrile, acetone, methyl isobutyl ketone, isopropyl acetate, tetrahydrofuran, methyl t-butyl ether, cyclopentyl methyl ether, N-methyl-2-pyrrolidone, dimethyl sulfoxide, dimethylformamide, 2-methyl-tetrahydrofuran, dichloromethane, 1,4-dioxane, 1,2-diflurobenzene, toluene, hexafluoroisopropanol, and water. In some embodiments, the anti-solvent is selected from n-heptane, n-hexane, n-pentane, and cyclohexane. In some embodiments, the HCl has sufficient solubility in the anti-solvent such that it can be used as a suitable solvent. In some embodiments, the organic solvent used in step (e) comprises a mixture of cyclopentyl methyl ether and n-heptane. In some embodiments, the organic solvent used in step (e) further comprises toluene.

In some embodiments, step (e) comprises providing obicetrapib in a mixture of cyclopentyl methyl ether and n-heptane, raising the temperature to between 35° C. and 40° C. under agitation, adding dry HCl in cyclopentyl methyl ether and raising the temperature again to between 50° C. and 55° C., then adding further n-heptane as an anti-solvent. At this point, a small portion of the reaction mixture can be extracted, cooled to a temperature of between 10° C. and 15° C., to obtain a slurry of crystals of crystalline obicetrapib HCl in a mixture cyclopentyl methyl ether and n-heptane (referred to herein as a "seed crystal slurry"). Optionally, all or a portion of the seed crystal slurry of crystalline obicetrapib HCl can then be added as seed crystals back to the reaction mixture. The seeds assist with nucleation but are not required and thus the process described herein can be done without seeding. The resulting reaction mixture is then cooled to a temperature between 5° C. and 15° C. (such as from 10° C. to 15° C.), followed by crystallizing the crystalline obicetrapib HCl from the system under agitation. In some embodiments, the crystalline obicetrapib HCl is crystallized over a period of 12 hours or more, with subsequent filtration (e.g., through a filter dryer), one or more optional washing steps, such as with a mixture of cyclopentyl methyl ether and n-heptane, and drying. In some cases, a wet filter cake of crystalline obicetrapib HCl is dried in vacuo in steps using temperatures of 25° C.-30° C., 30° C.-40° C., 40° C.-50° C. then 50° C.-55° C., such as 25° C., 35° C., 46° C., and 54° C.

Accordingly, in some embodiments, the method of preparing crystalline obicetrapib HCl comprises the addition of seed crystals (e.g., as a seed crystal slurry). The seed crystals of crystalline obicetrapib HCl can be formed as a slurry by following step (i) as set out above and after addition of dry HCl in cyclopentyl methyl ether and anti-solvent n-heptane, extracting a small portion of the reaction mixture, cooling to a temperature between 10° C. and 15° C., to provide a slurry of crystals of crystalline obicetrapib HCl in cyclopentyl methyl ether and n-heptane.

In some embodiments, the organic solvent used in step (e) comprises a mixture of cyclopentyl methyl ether and n-heptane. Accordingly, in one embodiment, step (e) comprises providing obicetrapib in a mixture of cyclopentyl methyl ether and n-heptane, raising the temperature to 35° C.-45° C. under agitation, adding dry HCl in cyclopentyl methyl ether and raising the temperature again to 50° C.-55° C., addition of further n-heptane as anti-solvent, the optional addition of seed crystals of crystalline obicetrapib HCl (e.g., as a seed crystal slurry prepared as described herein), cooling to a temperature between 5° C. and 15° C. (such as from 10° C. to 15° C.), followed by crystallizing the crystalline obicetrapib HCl from the system under agitation. In some embodiments, the crystalline obicetrapib HCl is crystallized over a period of at least 12 hours, with subsequent filtration, one or more optional washing steps, such as with a mixture of cyclopentyl methyl ether and n-heptane, and drying. In some embodiments, the crystalline obicetrapib HCl is dried in vacuo. In some embodiments, the crystalline obicetrapib HCl is subjected to drying in a vacuum drying cabinet at 25 mbar pressure and at a temperature of 55° C. for 10 hours or more. In some embodiments, after the drying procedure, the crystalline obicetrapib HCl includes less than 0.1 weight percent residual cyclopentyl methyl ether.

In some embodiments described hereinbefore, step (MM) of step (d) results in a solution of obicetrapib in cyclopentyl methyl ether with a concentration between 30 and 40 weight percent, such as from 33 to 37 weight percent, based on the weight of the solution, less than 1 weight percent of the first organic solvent used in step (d), and less than 1 weight percent of n-heptane. In some embodiments described hereinbefore, step (MM) of step (d) results in a solution of obicetrapib in cyclopentyl methyl ether with a concentration between 30 and 40 weight percent, such as from 33 to 37 weight percent, based on the weight of the solution, less than 1 weight percent of toluene, and less than 1 weight percent of n-heptane. These solutions can, after addition of n-heptane, advantageously be used in step (e). As will be appreciated by the skilled person, the n-heptane can also be added in step (d).

Accordingly, in some embodiments, step (e) comprises providing the solution of obicetrapib in cyclopentyl methyl ether with a concentration between 30 and 40 weight percent, such as from 33 to 37 weight percent, based on the weight of the solution, less than 1 weight percent of the first organic solvent used in step (d) (such as toluene), and less than 1 weight percent of n-heptane, addition of n-heptane, raising the temperature to 35° C. to 45° C. under agitation, adding dry HCl in cyclopentyl methyl ether and raising the temperature again to 50° C. to 55° C., addition of further n-heptane as anti-solvent, the optional addition of seed crystals of crystalline obicetrapib HCl (e.g., as a seed crystal slurry prepared as described herein), cooling to a temperature between 5° C. and 15° C. (such as from 10° C. to 15° C.), followed by crystallizing the crystalline obicetrapib HCl from the system under agitation, such as during a period of at least 12 hours, with subsequent filtration, one or more washing steps with a mixture of cyclopentyl methyl ether and n-heptane, and drying. In some cases, a wet filter cake of crystalline obicetrapib HCl is dried in vacuo in steps using temperatures of 25° C.-30° C., 30° C.-40° C., 40° C.-50° C. then 50° C.-55° C., such as 25° C., 35° C., 46° C., and 54° C.

In some embodiments, step (f) comprises the following steps:
- (aa) providing crystalline obicetrapib HCl;
- (bb) dissolving the crystalline obicetrapib HCl in ethanol under agitation. In some embodiments at a temperature between 15° C. and 25° C.;
- (cc) adding an aqueous NaOH solution to the solution obtained in step (bb) and agitating the resulting mixture, such as at a temperature from 20° C. to 25° C. for at least 4 hours, to obtain a solution of the sodium salt obicetrapib;
- (dd) optionally filtering the solution obtained in step (cc);
- (ee) preparing a CaCl2) solution by adding deionized water to CaCl2) under agitation, followed by adding ethyl acetate as a co-solvent, and stirring the resulting mixture for 10 to 30 minutes;
- (ff) cooling the CaCl2) solution obtained in step (ee) to a temperature between 8° C. and 12° C. and adding via a filter to the solution obtained in step (dd) (or (cc)) under agitation at said temperature;
- (gg) stirring the slurry resulting from step (ff) for about 1 to about 10 hours. In some embodiments the slurry is stirred at a temperature between 8° C. and 12° C.;
- (hh) isolating the solids from the slurry obtained in step (gg) by filtration. In some embodiments the isolating is conducted at a temperature between 8° C. and 12° C.;
- (ii) washing the filtration residue obtained in step (hh) with water in one or more washing steps. In some embodiments the washing is conducted at a temperature between 8° C. and 12° C.; and
- (jj) drying the washed residue obtained in step (ii), such as in vacuo at a temperature between 40° C. and 50° C. for more than 16 hours (such as 200 hours or more), to obtain amorphous obicetrapib hemicalcium.

In some embodiments of the subject method, crystalline obicetrapib HCl is isolated in step (f) with a purity of 98% or more, such as 98.5% or more, 99% or more 99.5% or more, or even more.

Another embodiment of the disclosure concerns the crystalline obicetrapib HCl obtained by or obtainable by the process as defined herein.

Still another embodiment of the disclosure is directed to crystalline obicetrapib HCl.

In some embodiments, crystalline obicetrapib HCl is stored at controlled room temperature and under a nitrogen atmosphere and is protected from moisture to prevent the formation of an amorphous solid, because crystalline obicetrapib HCl including crystalline obicetrapib HCl is hygroscopic.

Method of Preparing Amorphous Obicetrapib Hemicalcium Steps (N)-(h) in Addition to Aspects (a) to (f)

In some embodiments of the subject method, step (f) is followed by steps (g)-(h), wherein the crystalline obicetrapib HCl is converted to amorphous obicetrapib hemicalcium (Formula IB):

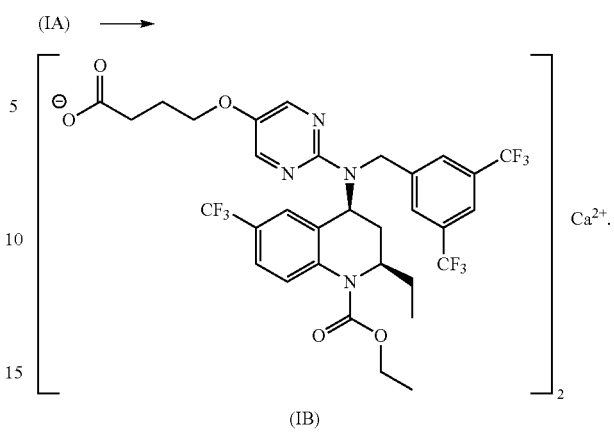

In some embodiments step (g), the preparation of amorphous obicetrapib hemicalcium includes steps (g1)-(g3) as set out below:
- (g1) converting crystalline obicetrapib HCl of step (f) to obicetrapib in an organic solvent;
- (g2) treating obicetrapib in the organic solvent with aqueous sodium hydroxide to form a sodium salt of obicetrapib; and
- (g3) treating the sodium salt of obicetrapib with aqueous calcium chloride to form amorphous obicetrapib hemicalcium;
- wherein the compounds in steps (g1) and (g2) are not isolated.

Accordingly, in some embodiments step, (g1) comprises the following steps:
- (aa) providing crystalline obicetrapib HCl as defined or obtained in step (f);
- (bb) dissolving crystalline obicetrapib HCl in a mixture of water and isopropyl acetate under agitation. In some embodiments, step (bb) is conducted at a temperature between 15° C. and 25° C.;
- (cc) allowing phase separation and subjecting the resulting organic phase to one or more subsequent washing steps with water, wherein each washing step is followed by separating off the aqueous phase, resulting in a washed organic phase; and
- (dd) performing two or more distillations on the washed organic phase resulting from step (cc) at a temperature of 50° C. or lower (such as 30° C. or lower), with intermediate additions of ethanol, to obtain a solution of the compound of obicetrapib in ethanol. In some embodiments step, (g2) comprises the following steps:
- (ee) adding an aqueous NaOH solution to the solution obtained in step (dd) and agitating the resulting mixture, such as at a temperature between 20° C. and 25° C. for at least 4 hours, to obtain a solution of the sodium salt of obicetrapib; and
- (ff) optionally filtering the solution obtained in step (ee).

In some embodiments step, (g3) comprises the following steps:
- (gg) preparing a CaCl2) solution by adding deionized water to CaCl2) under agitation, followed by adding ethyl acetate as a co-solvent, and stirring the resulting mixture for 10 to 30 minutes;
- (hh) cooling the CaCl2) solution obtained in step (gg) to a temperature from 8° C. to 12° C. and adding via a filter to the solution obtained in step (ff) or (ee) under agitation at said temperature;

(ii) stirring the slurry resulting from step (hh) for about 1 to 10 hours. In some embodiments of step (ii), the stirring is conducted at a temperature between 8° C. and 12° C.;

(jj) isolating the solids from the slurry obtained in step (ii) by filtration. In some embodiments of step (jj), the isolating is conducted at a temperature between 8° C. and 12° C.;

(kk) washing the filtration residue obtained in step (j) with water in one or more washing steps. In some embodiments of step (kk), the washing is conducted at a temperature between 8° C. and 12° C.; and (ll) drying the washed residue obtained in step (kk), such as in vacuo at a temperature from 40° C. to 50° C. for more than 16 hours (such as 50 hours, 100 hours, 150 hours, or 200 hours, or even more), to obtain the amorphous obicetrapib hemicalcium (also sometimes referred to herein as compound 3).

In some embodiments, step (g) comprises the following steps:

(aa) providing crystalline obicetrapib HCl, as defined or obtained in step (f);

(bb) dissolving crystalline obicetrapib HCl in ethanol under agitation. In some embodiments at a temperature between 15° C. and 25° C.;

(cc) adding an aqueous NaOH solution to the solution obtained in step (bb) and agitating the resulting mixture, such as at a temperature from 20° C. to 25° C. for at least 4 hours, to obtain a solution of the sodium salt of obicetrapib;

(dd) optionally filtering the solution obtained in step (cc);

(ee) preparing a CaCl2) solution by adding deionized water to CaCl2) under agitation, followed by adding ethyl acetate as a co-solvent, and stirring the resulting mixture for 10 to 30 minutes;

(ff) cooling the CaCl2) solution obtained in step (ee) to a temperature between 8° C. and 12° C. and adding via a filter to the solution obtained in step (dd) or (cc) under agitation at said temperature;

(gg) stirring the slurry resulting from step (ff) for about 1 to 10 hours. In some embodiments the slurry is stirred at a temperature between 8° C. and 12° C.;

(hh) isolating the solids from the slurry obtained in step (gg) by filtration. In some embodiments the isolating is conducted at a temperature between 8° C. and 12° C.;

(ii) washing the filtration residue obtained in step (hh) with water in one or more washing steps. In some embodiments the washing is conducted at a temperature between 8° C. and 12° C.; and (jj) drying the washed residue obtained in step (ii), such as in vacuo at a temperature between 40° C. and 50° C. for more than 16 hours (such as 50 hours, 100 hours, 150 hours, or 200 hours, or even more), to obtain the amorphous hemicalcium-salt of Formula (IB).

In some embodiments, amorphous obicetrapib hemicalcium is stored sealed at a temperature of less than 30° C. and protected from light.

In some embodiments, amorphous obicetrapib hemicalcium is submitted to a subsequent reworking procedure. In some embodiments, amorphous obicetrapib hemicalcium is further reworked by dissolving in ethanol (such as twice the weight of ethanol relative to amorphous obicetrapib hemicalcium at a temperature of 25° C. to 50° C., followed by cooling to 10° C. to 15° C., followed by filtering into a mixture of aqueous calcium chloride solution and ethyl acetate, also cooled to 10° C. to 15° C., followed by filtering, washing with water and drying in vacuo at 45° C. or less for 20 hours or more.

In many embodiments of the disclosure, amorphous obicetrapib hemicalcium is processed to achieve a particle size distribution. In many embodiments such processing is by milling. Examples of milling include hammer milling, ball milling, and jet milling. In other embodiments, spray drying may be used to achieve a particle size distribution. Thus, in some embodiments, of the disclosure, spray-dried amorphous obicetrapib hemicalcium is provided. An example of jet-milled amorphous obicetrapib hemicalcium is provided in Example 14.

In many embodiments of the disclosure, unmilled amorphous obicetrapib hemicalcium is provided. In many embodiments of the disclosure, milled amorphous obicetrapib hemicalcium is provided.

In many embodiments, the particle size distribution of amorphous obicetrapib hemicalcium is such that 90% of the particles have a diameter of about 15 microns or less. In these and other embodiments, 90% of the particles have a diameter of about 14 microns or less, 13 microns or less, 12 microns or less, 11 microns or less, 10 microns or less, 9 microns or less, 8 microns or less, 7 microns or less, 6 microns or less, 5 microns or less, 4 microns or less, or 3 microns or less.

In some embodiments, 90% of the particles have a diameter between about 6 microns and 15 microns.

In these and other embodiments, the particle size distribution of amorphous obicetrapib hemicalcium is such that 50% of the particles have a diameter of about 5 microns or less, such as, for example, 4 microns or less or 3 microns or less.

In these and other embodiments, the particle size distribution of amorphous obicetrapib hemicalcium is such that 10% of the particles have a diameter of about 2 microns or less.

Amorphous obicetrapib hemicalcium of the disclosure can be made with high chemical purity according to the processes of the disclosure. Such levels of purity include greater than 98.0% pure such as greater than 98.1%, 98.2%, 98.3%, 98.4%, 98.5%, 98.6%, 98.7%, 98.8%, 98.9%, 99.0%, 99.1%, 99.2%, 99.3%, 99.4%, 99.5%, 99.6%, 99.7%, 99.8%, or 99.9% or more. The highest level of purities such as greater than 99.8% or 99.9% pure are more readily achieved with processes where crystalline obicetrapib HCl is used as an intermediate.

As summarized above, also provided herein are amorphous calcium salts of obicetrapib including amorphous obicetrapib hemicalcium. New intermediates for use in the synthesis of obicetrapib and salts thereof are also provided.

The term "pharmaceutically acceptable" indicates that the material does not have properties that would cause a reasonably prudent medical practitioner to avoid administration of the material to a patient, taking into consideration the disease or conditions to be treated and the respective route of administration. For example, it is commonly required that such a material be essentially sterile, e.g., for injectables.

The term "carrier" refers to a glidant, diluent, adjuvant, excipient, or vehicle etc. with which the compound is administered, without limitation. Examples of carriers are described herein and also in Remington: The Science and Practice of Pharmacy (Remington: The Science and Practice of Pharmacy, 23rd Edition, ISBN-13: 978-0128200070).

The term "effective amount" or "therapeutically effective amount" refers to an amount that is sufficient to effect treatment, as defined herein, when administered to a mammal in need of such treatment. The therapeutically effective amount will vary depending upon the patient being treated, the weight and age of the patient, the severity of the disease condition, the manner of administration and the like, which can readily be determined by one of ordinary skill in the art.

The term "solvate" means a complex, such as an adduct, formed between an organic compound and a solvent molecule in the solid state. Solvates may be held together by hydrogen bonding, van der Waals forces, or other non-covalent bonding interactions. Solvates may be channel solvates in that variable amounts of solvent may be present in a channel of the structure of the solid.

The term "treatment" or "treating," to the extent it relates to a disease or condition includes preventing the disease or condition from occurring, inhibiting the disease or condition, eliminating the disease or condition, and/or relieving one or more symptoms of the disease or condition.

Unless specifically stated otherwise, where a compound may assume alternative tautomeric, regioisomeric and/or stereoisomeric forms, all alternative isomers, are intended to be encompassed within the scope of the claimed subject matter. For example, when a compound is described as a particular optical isomer D- or L-, it is intended that both optical isomers be encompassed herein. For example, where a compound is described as having one of two tautomeric forms, it is intended that both tautomers be encompassed herein. Thus, the compounds provided herein may be enantiomerically pure, or be stereoisomeric or diastereomeric mixtures. The compounds provided herein may contain chiral centers. Such chiral centers may be of either the (R) or (S) configurations, or may be a mixture thereof. The chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

The present disclosure also encompasses all suitable isotopic variants of the compounds according to the present disclosure, whether radioactive or not. An isotopic variant of a compound according to the present disclosure is understood to mean a compound in which at least one atom within the compound according to the present disclosure has been exchanged for another atom of the same atomic number, but with a different atomic mass than the atomic mass which usually or predominantly occurs in nature. Examples of isotopes which can be incorporated into a compound according to the present disclosure are those of hydrogen, carbon, nitrogen, oxygen, fluorine, chlorine, bromine and iodine, such as $^2$H (deuterium), $^3$H (tritium), $^{13}$C, $^{14}$C, $^{15}$N, $^{17}$O, $^{18}$O, $^{18}$F, $^{36}$Cl, $^{82}$Br, $^{123}$I, $^{124}$I, $^{125}$I, $^{129}$I and $^{131}$I. Particular isotopic variants of a compound according to the present disclosure, especially those in which one or more radioactive isotopes have been incorporated, may be beneficial, for example, for the examination of the mechanism of action or of the active compound distribution in the body. Compounds labelled with $^3$H, $^{14}$C and/or $^{18}$F isotopes are suitable for this purpose. In addition, the incorporation of isotopes, for example of deuterium, can lead to particular therapeutic benefits as a consequence of greater metabolic stability of the compound, for example an extension of the half-life in the body or a reduction in the active dose required. In some embodiments, hydrogen atoms of the compounds described herein may be replaced with deuterium atoms. In certain embodiments, "deuterated" as applied to a chemical group and unless otherwise indicated, refers to a chemical group that is isotopically enriched with deuterium in an amount substantially greater than its natural abundance. Isotopic variants of the compounds according to the present disclosure can be prepared by various, including, for example, the methods described below and in the working examples, by using corresponding isotopic modifications of the particular reagents and/or starting compounds therein.

Thus, any of the embodiments described herein are meant to include, a single stereoisomer, a mixture of stereoisomers and/or an isotopic form of the compounds.

Unless otherwise indicated, the term "about" or "approximately" means an acceptable error for a particular value as determined by one of ordinary skill in the art, which depends in part on how the value is measured or determined. In certain embodiments, the term "about" or "approximately" means within 1, 2, or 3 standard deviations. In certain embodiments, the term "about" or "approximately" means within 10% 9%, 8%, 7%, 6%, 5%, 4%, 3%, 2%, 1%, 0.5%, 0.4%, 0.3%, 0.25%, 0.2%, 0.1% or 0.05% of a given value or range. Unless otherwise specified, the term "about" means within plus or minus 10% of a the explicitly recited value, rounded either up or down to the nearest integer.

Thus, the subject method has been described by reference to certain embodiments discussed above. It will be recognized that these embodiments are susceptible to various modifications and alternative forms well known to those of skill in the art.

The present disclosure may be further described by one or more of the non-limiting clauses that follow:

Clause 1. An amorphous calcium salt of obicetrapib.

Clause 2. Amorphous obicetrapib hemicalcium.

Clause 3. Stable amorphous obicetrapib hemicalcium.

Clause 4. Substantially pure amorphous obicetrapib hemicalcium.

Clause 5. The amorphous obicetrapib hemicalcium salt of clauses 2-4, substantially free of any crystalline salt of obicetrapib hemicalcium.

Clause 6. The amorphous obicetrapib hemicalcium of clauses 2-5, having an x-ray powder diffraction pattern substantially the same as that of FIG. 1.

Clause 7. The amorphous obicetrapib hemicalcium of clauses 2-5, having an x-ray powder diffraction pattern comprising one or more x-ray powder diffraction peaks at about 3.4° 2θ, about 7.0° 2θ, and about 9.2° 2θ.

Clause 8. The amorphous obicetrapib hemicalcium of clauses 2-7, wherein the amorphous obicetrapib hemicalcium does not birefringe.

Clause 9. The amorphous obicetrapib hemicalcium of clauses 2-8, having a glass transition temperature at a value between about 107° C. and about 112° C.

Clause 10. The amorphous obicetrapib hemicalcium of clause 9, wherein the glass transition temperature is measured with modulated differential scanning calorimetry.

Clause 11. The amorphous obicetrapib hemicalcium of clause 10, wherein the measurement with modulated differential scanning calorimetry uses a sample pan which is open.

Clause 12. The amorphous obicetrapib hemicalcium of clause 11, wherein the opening is a pinhole.

Clause 13. The amorphous obicetrapib hemicalcium of clauses 8-12, wherein the glass transition temperature is at a value between about 110° C. and about 112° C.

Clause 14. The amorphous obicetrapib hemicalcium of clauses 2-13, having a glass transition temperature of less than about 100° C. when measured by differential scanning calorimetry using a closed sample pan.

Clause 15. The amorphous obicetrapib hemicalcium of clause 14, having a glass transition temperature at a value between about 70° C. and about 92° C. when measured by differential scanning calorimetry using a closed sample pan.

Clause 16. The amorphous obicetrapib hemicalcium of clauses 2-15, having a loss in weight of less than about 1% when heated to about 200° C.

Clause 17. The amorphous obicetrapib hemicalcium of clause 16, wherein the weight loss is between about 0.8% and about 0.95%.

Clause 18. The amorphous obicetrapib hemicalcium of clause 17, wherein the weight loss is between about 0.84% and about 0.92%.

Clause 19. The amorphous obicetrapib hemicalcium of clauses 2-18, having a water content of less than about 5%.

Clause 20. The amorphous obicetrapib hemicalcium of clause 19, having a water content of less than about 4%.

Clause 21. The amorphous obicetrapib hemicalcium of clause 20, having a water content of less than about 3%.

Clause 22. The amorphous obicetrapib hemicalcium of clause 19, having a water content of between about 0.5% and about 1.5%.

Clause 23. The amorphous obicetrapib hemicalcium of clauses 2-22, in a bulk form or formulated composition having a particle size distribution wherein about 90% of the particles have a diameter of about 15 microns or less.

Clause 24. The amorphous obicetrapib hemicalcium of clause 23, wherein about 90% of the particles have a diameter of between about 6 microns and about 15 microns.

Clause 25. The amorphous obicetrapib hemicalcium of clause 24, having a particle size distribution wherein about 90% or more of the particles have a diameter of about 14 microns or less.

Clause 26. The amorphous obicetrapib hemicalcium of clause 25, having a particle size distribution wherein about 90% or more of the particles have a diameter of about 13 microns or less.

Clause 27. The amorphous obicetrapib hemicalcium of clause 26, having a particle size distribution wherein about 90% or more of the particles have a diameter of about 12 microns or less.

Clause 28. The amorphous obicetrapib hemicalcium of clause 27, having a particle size distribution wherein about 90% or more of the particles have a diameter of about 11 microns or less.

Clause 29. The amorphous obicetrapib hemicalcium of clause 28, having a particle size distribution wherein about 90% or more of the particles have a diameter of about 10 microns or less.

Clause 30. The amorphous obicetrapib hemicalcium of clause 29, having a particle size distribution wherein about 90% or more of the particles have a diameter of about 9 microns or less.

Clause 31. The amorphous obicetrapib hemicalcium of clause 30, having a particle size distribution wherein about 90% or more of the particles have a diameter of about 8 microns or less.

Clause 32. The amorphous obicetrapib hemicalcium of clause 31, having a particle size distribution wherein about 90% or more of the particles have a diameter of about 7 microns or less.

Clause 33. The amorphous obicetrapib hemicalcium of clause 32, having a particle size distribution wherein about 90% or more of the particles have a diameter of about 6 microns or less.

Clause 34. The amorphous obicetrapib hemicalcium of clause 33, having a particle size distribution wherein about 90% or more of the particles have a diameter of about 5 microns or less.

Clause 35. The amorphous obicetrapib hemicalcium of clause 34, having a particle size distribution wherein about 90% or more of the particles have a diameter of about 4 microns or less.

Clause 36. The amorphous obicetrapib hemicalcium of clause 35, having a particle size distribution wherein about 90% or more of the particles have a diameter of about 3 microns or less.

Clause 37. The amorphous obicetrapib hemicalcium of clauses 2-36, in a bulk form or formulated composition having a particle size distribution wherein about 50% of the particles have a diameter of about 5 microns or less.

Clause 38. The amorphous obicetrapib hemicalcium of clause 37, having a particle size distribution wherein about 50% of the particles have a diameter of about 4 microns or less.

Clause 39. The amorphous obicetrapib hemicalcium of clause 38, having a particle size distribution wherein about 50% of the particles have a diameter of about 3 microns or less.

Clause 40. The amorphous obicetrapib hemicalcium of clauses 2-39, in a bulk form or formulated composition having a particle size distribution wherein about 10% of the particles have a diameter of about 2 microns or less.

Clause 41. The amorphous obicetrapib hemicalcium of clauses 2-40, having a chemical purity of at least 98.0%.

Clause 42. The amorphous obicetrapib hemicalcium of clause 41, having a chemical purity of at least 99.0%.

Clause 43. The amorphous obicetrapib hemicalcium of clause 42, having a chemical purity of at least 99.5%.

Clause 44. The amorphous obicetrapib hemicalcium of clause 43, having a chemical purity of at least 99.6%.

Clause 45. The amorphous obicetrapib hemicalcium of clause 44, having a chemical purity of at least 99.7%.

Clause 46. The amorphous obicetrapib hemicalcium of clause 45, having a chemical purity of at least 99.8%.

Clause 47. The amorphous obicetrapib hemicalcium of clause 46, having a chemical purity of at least 99.9%.

Clause 48. The amorphous obicetrapib hemicalcium of clauses 2-47, having a solid-state $^{13}$C-NMR spectrum substantially the same as that of FIG. 17.

Clause 49. The amorphous obicetrapib hemicalcium of clauses 2-48, having a solid-state $^{13}$C-NMR spectrum where no peak is present at about 22.1 ppm.

Clause 50. The amorphous obicetrapib hemicalcium of clauses 2-49, having a solid-state $^{13}$C-NMR spectrum where no peak is present at about 29.5 ppm.

Clause 51. Unmilled amorphous obicetrapib hemicalcium.

Clause 52. Milled amorphous obicetrapib hemicalcium.

Clause 53. The amorphous obicetrapib hemicalcium of clauses 2-50, wherein the amorphous obicetrapib hemicalcium has been milled.

Clause 54. The amorphous obicetrapib hemicalcium of clauses 2-50 or 53, wherein the amorphous obicetrapib hemicalcium has been jet milled.

Clause 55. The amorphous obicetrapib hemicalcium of clauses 2-50 or 53-54 wherein the amorphous obicetrapib hemicalcium has been spray dried.

Clause 56. Amorphous obicetrapib hemicalcium prepared by a synthetic process wherein an intermediate in the process comprises crystalline obicetrapib HCl.

Clause 57. The amorphous obicetrapib hemicalcium of clauses 2-56, wherein the amorphous obicetrapib hemicalcium is prepared by a synthetic process wherein an intermediate in the process comprises crystalline obicetrapib HCl.

Clause 58. Obicetrapib HCl.

Clause 59. Crystalline obicetrapib HCl.

Clause 60. An amorphous HCl obicetrapib compound.

Clause 61. A solvate of the HCl obicetrapib of clauses 58-60.

Clause 62. HCl obicetrapib of clauses 58-61, wherein the weight percent of HCl is between about 0.01% and about 8%.

Clause 63. A composition comprising crystalline obicetrapib HCl of any one of clauses 58-62.

Clause 64. The crystalline obicetrapib HCl of clause 58-60 or 62-63, wherein the crystalline obicetrapib HCl is a solvate.

Clause 65. The crystalline obicetrapib HCl of clause 64, wherein the solvate comprises obicetrapib and hydrochloric acid.

Clause 66. The crystalline obicetrapib HCl of clause 65, wherein the solvate comprises an organic solvent.

Clause 67. The crystalline obicetrapib HCl of clause 66, where the solvate comprises a solvent wherein the solubility is sufficient to dissolve sufficient HCl so as to deliver sufficient HCl to create crystalline obicetrapib HCl.

Clause 68. The solvate of any one of clauses 61, or 64-67, wherein the solvent of the solvate is selected from methanol, ethanol, isopropanol, acetic acid, acetonitrile, acetone, methyl isobutyl ketone, isopropyl acetate, tetrahydrofuran, methyl t-butyl ether, cyclopentyl methyl ether (CPME), N-methyl-2-pyrrolidone, dimethyl sulfoxide, dimethylformamide, 2-methyl-tetrahydrofuran, dichloromethane, 1,4-dioxane, 1,2-diflurobenzene, toluene, and hexafluoroisopropanol.

Clause 69. The crystalline obicetrapib HCl of clause 68, wherein the solvent is CPME.

Clause 70. The crystalline obicetrapib HCl of any one of clauses 58-59 or 61-69, having an x-ray powder diffraction pattern substantially the same as that in FIG. 19.

Clause 71. The crystalline obicetrapib HCl of any one of clauses 58-59 or 61-69, having an x-ray powder diffraction pattern comprising a peak at about 9.8° 2θ.

Clause 72. The crystalline obicetrapib HCl of any one of clauses 58-59, 61-69 or 71, having an x-ray powder diffraction pattern comprising one or more peaks at about 8.1° 2θ, about 9.8° 2θ, about 13.8° 2θ, about 16.7° 2θ, and about 19.5° 2θ.

Clause 73. A salt according to Formula (VI):

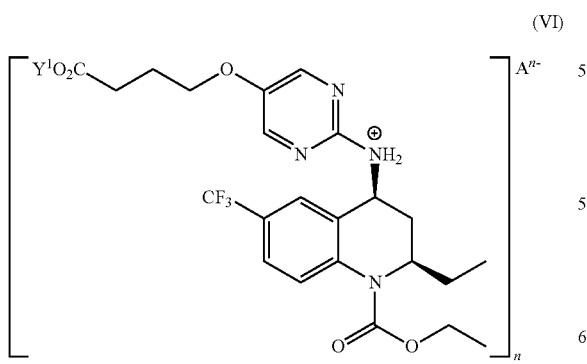

(VI)

wherein $Y^1$ is a protecting group, An– is an anion; and n is an integer from 1-3.

Clause 74. The salt according to clause 73, wherein the compound is a mesylate salt of the following structure (Compound 1D):

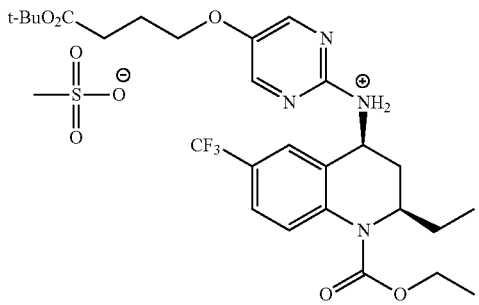

1D

Clause 75. The crystalline mesylate salt of Compound 1D of clause 74.

Clause 76. The crystalline mesylate salt of Compound 1D of clause 75, having a powder diffraction pattern substantially the same as any of the four x-ray powder patterns set forth in FIG. 20.

Clause 77. The crystalline mesylate salt of Compound 1D of clause 75, having an x-ray powder diffraction pattern comprising one or more peaks at about 5.2°2θ and about 9.1°2θ.

Clause 78. The crystalline mesylate salt of Compound 1D of clauses 75-77 having an x-ray powder diffraction pattern comprising one or more peaks at about 9.1°2θ, about 15.9°2θ, about 16.5°2θ, about 17.2°2θ, about 18.6°2θ, and about 19.2°2θ.

Clause 79. A method of preparing obicetrapib, wherein the method comprises:
(a) preparing a compound of Formula (IV), by coupling a compound of Formula (II) or a salt thereof, with a compound of Formula (III):

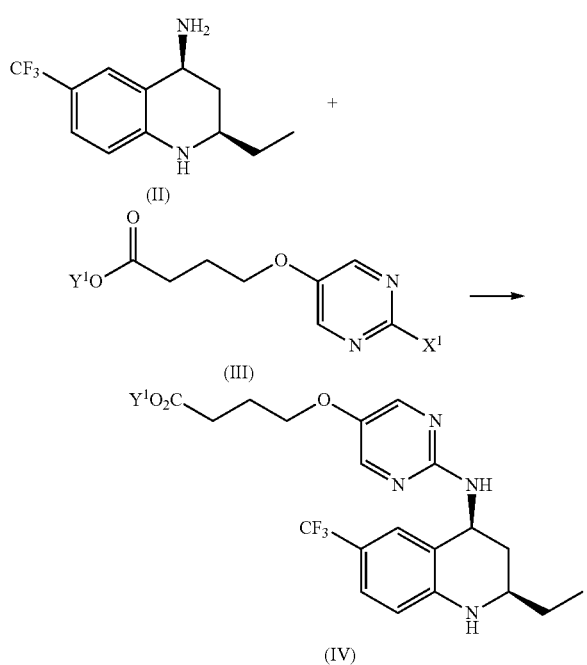

where, $X^1$ is a leaving group and $Y^1$ is a protecting group;
(b) preparing a carbamate of Formula (V) from the compound of Formula (IV) and isolating as a solid salt form of Formula (VI):

IV →

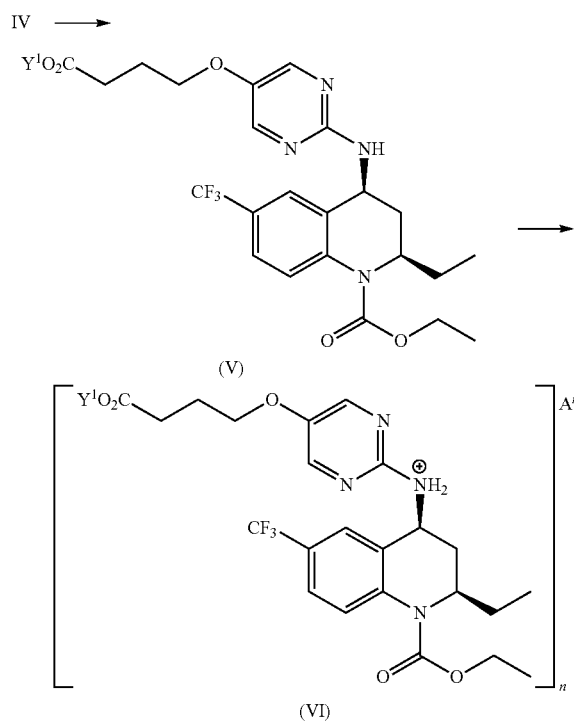

where Y¹ is a protecting group, An– is an anion and n is an integer from 1-3;
(c) optionally desalting the compound of Formula (VI) and alkylating with a compound of Formula (VII) to provide a compound of Formula (VIII):

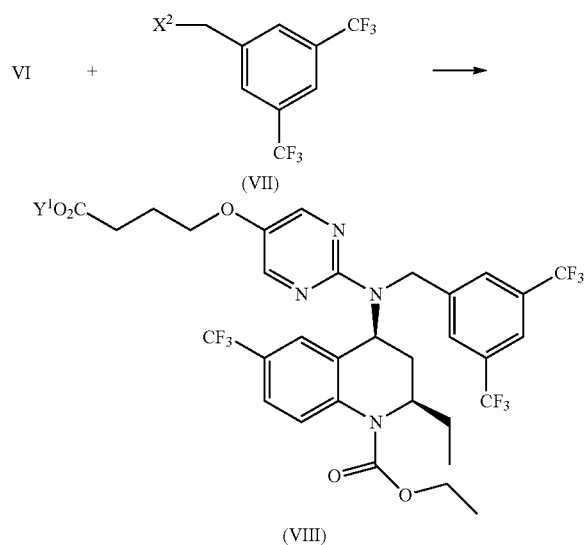

where X² is a leaving group and Y¹ is a protecting group; and
(d) converting the compound of Formula (VIII) to obicetrapib, wherein the reaction steps (a)-(d) are performed in an organic solvent, compounds (IV), (V), and (VIII) are optionally not isolated from the organic solvent, and wherein the process does not require chromatography.

Clause 80. The method according to clause 79, wherein the compound of Formula (II) in step (a) is obtained by applying the following steps before step (a):

(pre-a1) providing a compound of Formula (IIA) or (IIB):

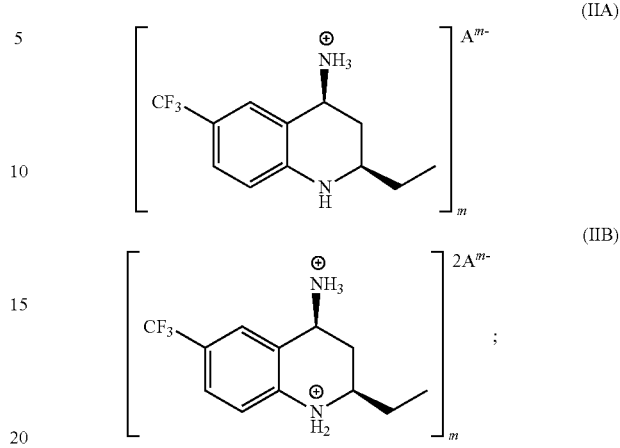

and
(pre-a2) desalting the compound of Formula (IIA) or (IIB) to obtain the compound of Formula (II);
wherein the reaction in step (pre-a2) is performed in an organic solvent and the compound of Formula (II) is optionally not isolated from the organic solvent, and the process does not require chromatography.

Clause 81. The method according to clause 80, wherein the salt of Formula (IIA) or (IIB) is chosen from salts with an anion $A^{m-}$ selected from a sulfonate, a sulfate, a halogen, acetate, aspartate, benzoate, bicarbonate, bitartrate, carbonate, citrate, decanoate, fumarate, gluceptate, gluconate, glutamate, glycolate, hexanoate, hydroxynaphthoate, isethionate, lactate, lactobionate, malate, maleate, mandelate, mucate, nitrate, octanoate, oleate, pamoate, pantothenate, phosphate, polygalacturonate, propionate, salicylate, stearate, succinate, tartrate, and teoclate; wherein the sulfonate may be a besylate, tosylate, napsylate, camsylate, esylate, edisylate, or mesylate; the sulfate may be a methylsulfate; and the halogen may be a chloride, iodide, or bromide.

Clause 82. The method of clause 81, wherein the salt with an anion $A^{m-}$ is selected from chloride, bromide, bitartrate, a sulfate, and a sulfonate.

Clause 83. The method of clause 82, wherein the salt with an anion $A^{m-}$ is selected from chloride, bromide, bitartrate, and mesylate.

Clause 84. The method of any one of clauses 79-83, wherein Y¹ in the compounds of Formulae (III)-(VI) and (VIII) is selected from an alkyl group, a substituted alkyl group, an aryl group, a substituted aryl group, an allyl group, a substituted allyl group and a silyl group.

Clause 85. The method of clause 84, wherein Y¹ in the compounds of Formulae (III)-(VI) and (VIII) is selected from t-butyl, methyl, ethyl, benzyl, allyl, substituted allyl, 2,2,2-trifluroethyl, phenyl, 4-methoxybenzyl ester, a 2,6-disubstituted phenol, and a silyl group.

Clause 86. The method of clause 85, wherein Y¹ in the compounds of Formulae (III)-(VI) and (VIII) is t-butyl.

Clause 87. The method of any one of clauses 79-86, wherein the salt of Formula (VI) is chosen from salts with an anion $A^{n-}$ selected from a sulfonate, a sulfate, a halogen, acetate, aspartate, benzoate, bicarbonate, bitartrate, carbonate, citrate, decanoate, fumarate, gluceptate, gluconate, glutamate, glycolate, hexanoate, hydroxynaphthoate, isethionate, lactate, lactobionate, malate, maleate, mandelate, mucate, nitrate, octanoate, oleate, pamoate, pantothenate, phosphate, polygalacturonate, propionate, salicylate, stearate, succinate, tartrate, and teoclate; wherein the sulfonate may be a besylate, tosylate, napsylate, camsylate, esylate, edisylate, or mesylate; the sulfate may be a methylsulfate; and the halogen may be a chloride, iodide, or bromide.

Clause 88. The method of clause 87, wherein the salt with an anion $A^{n-}$ is selected from chloride, bromide, bitartrate, a sulfate, and a sulfonate.

Clause 89. The method of clause 87, wherein the salt with an anion $A^{n-}$ is selected from chloride, bromide, bitartrate, and mesylate.

Clause 90. The method of clause 87, wherein the salt form of Formula (VI) is the mesylate salt, Compound 1D:

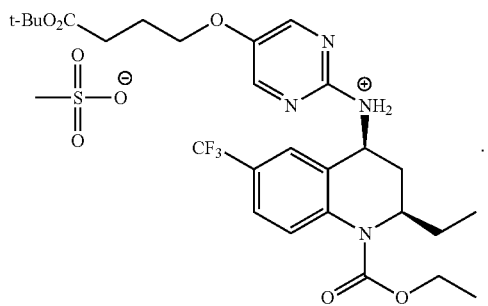

Clause 91. The method of clause 90, wherein the mesylate salt is crystalline.

Clause 92. The method of any one of clauses 79-91, wherein $X^1$ in the compound of Formula (III) is selected from a halogen, a carbamate, and a substituted sulfonyloxy group.

Clause 93. The method of clause 92, wherein $X^1$ in the compound of Formula (III) is a halogen.

Clause 94. The method of clause 93, wherein the halogen is chloride.

Clause 95. The method of any one of clauses 79-94, wherein $X^2$ in the compound of Formula (VII) is selected from a halogen and a substituted sulfonyloxy group.

Clause 96. The method of clause 95, wherein $X^2$ in the compound of Formula (III) is a halogen.

Clause 97. The method of clause 96, wherein the halogen is bromide.

Clause 98. A method of preparing an amorphous hemicalcium salt of obicetrapib wherein the method comprises:
  (i) treating obicetrapib with HCl to obtain a crystalline obicetrapib HCl compound;
  (ii) isolating the crystalline obicetrapib HCl compound;
  (iii) preparing an amorphous hemicalcium salt of obicetrapib from the crystalline obicetrapib HCl compound isolated in step (ii); and
  (iv) isolating an amorphous hemicalcium salt of obicetrapib.

Clause 99. The method of clause 98, wherein the isolated crystalline obicetrapib HCl compound in step (ii) comprises a compound of Formula (IH):

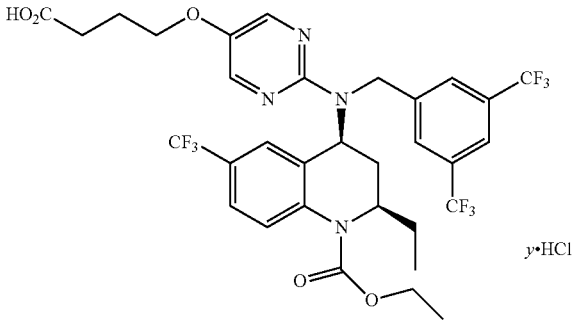

wherein y varies from 0.002 to 1.5.

Clause 100. The method according to clauses 98 or 99, wherein the preparation of the amorphous hemicalcium salt of Formula (I) in step (iii) comprises the following steps:
  (iii-1) converting the crystalline obicetrapib HCl compound of step (ii) to provide obicetrapib in one or more suitable solvents selected from organic solvents and aqueous solvents;
  (iii-2) treating obicetrapib in the organic solvent with aqueous sodium hydroxide to form a sodium salt of obicetrapib; and
  (iii-3) treating the sodium salt of obicetrapib with aqueous calcium chloride to form the amorphous hemicalcium salt of obicetrapib;
wherein the compounds in steps (iii-1) and (iii-2) are optionally not isolated.

Clause 101. The method according to clauses any one of clauses 98-100, wherein the amorphous hemicalcium salt of obicetrapib is amorphous obicetrapib hemicalcium.

Clause 102. The method of any one of clauses 98-101, wherein the amorphous calcium salt of obicetrapib is isolated with a chemical purity of at least 99%.

Clause 103. The method of clause 102, wherein the amorphous calcium salt of obicetrapib is isolated with a purity of at least 99.1%.

Clause 104. The method of clause 102, wherein the amorphous calcium salt of obicetrapib is isolated with a purity of at least 99.2%.

Clause 105. The method of clause 102, wherein the amorphous calcium salt of obicetrapib is isolated with a purity of at least 99.3%.

Clause 106. The method of clause 102, wherein the amorphous calcium salt of obicetrapib is isolated with a purity of at least 99.4%.

Clause 107. The method of clause 102, wherein the amorphous calcium salt of obicetrapib is isolated with a purity of at least 99.5%.

Clause 108. The method of clause 102, wherein the amorphous calcium salt of obicetrapib is isolated with a purity of at least 99.6%.

Clause 109. The method of clause 102, wherein the amorphous calcium salt of obicetrapib is isolated with a purity of at least 99.7%.

Clause 110. The method of clause 102, wherein the amorphous calcium salt of obicetrapib is isolated with a purity of at least 99.8%.

Clause 111. The method of clause 102, wherein the amorphous calcium salt of obicetrapib is isolated with a purity of at least 99.9%.

Clause 112. The method according to clauses any of clauses 102-111, wherein the amorphous calcium salt of obicetrapib is amorphous obicetrapib hemicalcium.

Clause 113. A pharmaceutical composition comprising an amorphous salt of obicetrapib calcium of any one of clauses 1-57 and one or more pharmaceutically acceptable carriers.

Clause 114. The pharmaceutical composition of clause 113, wherein the amorphous salt of obicetrapib calcium is amorphous obicetrapib hemicalcium.

Clause 115. A method of treating a subject suffering from or having an increased risk of developing a cardiovascular disease, the method comprising administering a therapeutically effective amount of a pharmaceutical composition according to clauses 113 or 114 to the subject.

Clause 116. An amorphous calcium salt of obicetrapib prepared according to the processes of any one of clauses 79-112.

Clause 117. The amorphous calcium salt of clause 116, which is amorphous obicetrapib hemicalcium.

Clause 118. A method of making an amorphous obicetrapib calcium salt comprising treating obicetrapib with an acid to form a salt, solvate composition, or combination thereof, isolating the salt, solvate, composition, or combination thereof; treating the salt, solvate, composition, or combination thereof with a calcium source to make an amorphous obicetrapib hemicalcium salt.

Clause 119. The method of clause 118, wherein the calcium source is calcium chloride.

Clause 120. A salt, solvate, composition or combination thereof, comprising obicetrapib and a free acid.

Clause 121. The salt of clause 120.

Clause 122. The solvate of clause 120.

Clause 123. The composition of clause 120.

Clause 124. The salt, solvate, composition, or combination thereof of clause 120, wherein the free acid is selected from a sulfonic acid, a sulfuric acid, a halogenated acid, acetic acid, aspartic acid, benzoic acid, bicarbonic acid, bitartaric acid, carbonic acid, citric acid, decanoic acid, fumaric acid, gluceptic acid, gluconic acid, glutamic acid, glycolic acid, hexanoic acid, hydroxynaphthoic acid, isethionic acid, lactic acid, lactobionic acid, malic acid, maleic acid, mandelic acid, mucic acid, nitric acid, octanoic acid, oleic acid, pamoic acid, pantothenic acid, phosphic acid, polygalacturonic acid, propionic acid, salicylic acid, stearic acid, succinic acid, tartric acid, and a teoclic acid; wherein the sulfonic acid may be a benzene sulfonic acid, toluene sulfonic acid, naphthalene sulfonic acid, ethane disulfonic acid, or methanesulfonic acid; the sulfuric acid a methyl sulfuric acid; and the halogenated acid may be HCl, HBr, or HI.

Clause 125. The method of clause 118, wherein the calcium source is a halogenated calcium salt.

Clause 126. The method of clause 118, wherein the calcium source is a soluble calcium salt.

Clause 127. The method of clause 118, wherein the calcium source is a calcium salt.

Clause 128. The obicetrapib hydrochloride of clauses 58 or 59, comprising chloride ions hydrogen bound to at least one protonated nitrogen on the pyrimidine ring of obicetrapib.

Clause 129. The obicetrapib hydrochloride of clauses 59 or 128, having an asymmetric unit comprising four cationic obicetrapib moieties, two neutral obicetrapib molecules, four chloride anions, and at least one solvent molecule.

Clause 130. The obicetrapib hydrochloride of clause 129, wherein the asymmetric unit comprises two solvent molecules.

Clause 131. The obicetrapib hydrochloride of clause 129, wherein the asymmetric unit comprises three solvent molecules.

Clause 132. The obicetrapib hydrochloride of any one of clauses 129-132, wherein the solvent molecules are chosen from heptane and cyclopentyl methyl ether.

Clause 133. The obicetrapib hydrochloride of any one of clauses 128-132, having the following unit cell parameters:

| crystal system, space group | Monoclinic |
|---|---|
| data collection temperature (K) | 150(2) |
| a (Å) | 22.088(10) |
| b (Å) | 19.332(8) |
| c (Å) | 28.582(11) |
| α (°) | 90 |
| β (°) | 109.136(15) |
| γ (°) | 90 |
| volume (Å$^3$) | 11531(8) |
| Z | 2 |

Clause 134. Form A crystalline obicetrapib hydrochloride.

Clause 135. The Form A crystalline obicetrapib hydrochloride of clause 134, having an x-ray powder diffraction pattern comprising a peak at about 8.6°2θ, two peaks between about 9.7°2θ and about 10.4°2θ, and two peaks between about 8.6°2θ and 9.0°2θ.

Clause 136. The Form A crystalline obicetrapib hydrochloride of clause 134, having an x-ray powder diffraction pattern substantially the same pattern as that of FIG. 22.

Clause 137. Form B crystalline obicetrapib hydrochloride.

Clause 138. The Form B crystalline obicetrapib hydrochloride of clause 136, having an x-ray powder diffraction pattern comprising peaks at about 6.5°2θ, about 8.8°2θ, and about 11.0020.

Clause 139. The Form B crystalline obicetrapib hydrochloride of clause 137, having an x-ray powder diffraction pattern substantially the same pattern as that of FIG. 23.

Clause 140. Form C crystalline obicetrapib hydrochloride.

Clause 141. The Form C crystalline obicetrapib hydrochloride of clause 140, having an x-ray powder diffraction pattern substantially the same pattern as that of FIG. 24.

Clause 142. Form D crystalline obicetrapib hydrochloride.

Clause 143. The Form D crystalline obicetrapib hydrochloride of clause 142, having an x-ray powder diffraction pattern substantially the same pattern as that of FIG. 25.

Clause 144. Crystalline obicetrapib hydrochloride of clause 59 having an x-ray powder diffraction pattern comprising a peak between about 4.3° 2θ and about 4.7° 20.

EXAMPLES

The Examples in this section are offered by way of illustration, and not by way of limitation. The examples can represent only some embodiments, and it should be understood that the following examples are illustrative and not limiting. All substituents, unless otherwise specified, are as previously defined. The reagents and starting materials are readily available to one of ordinary skill in the art. The specific synthetic steps for each of the routes described may be combined in different ways, or in conjunction with steps from different schemes, to prepare the compounds described herein.

Scheme 1

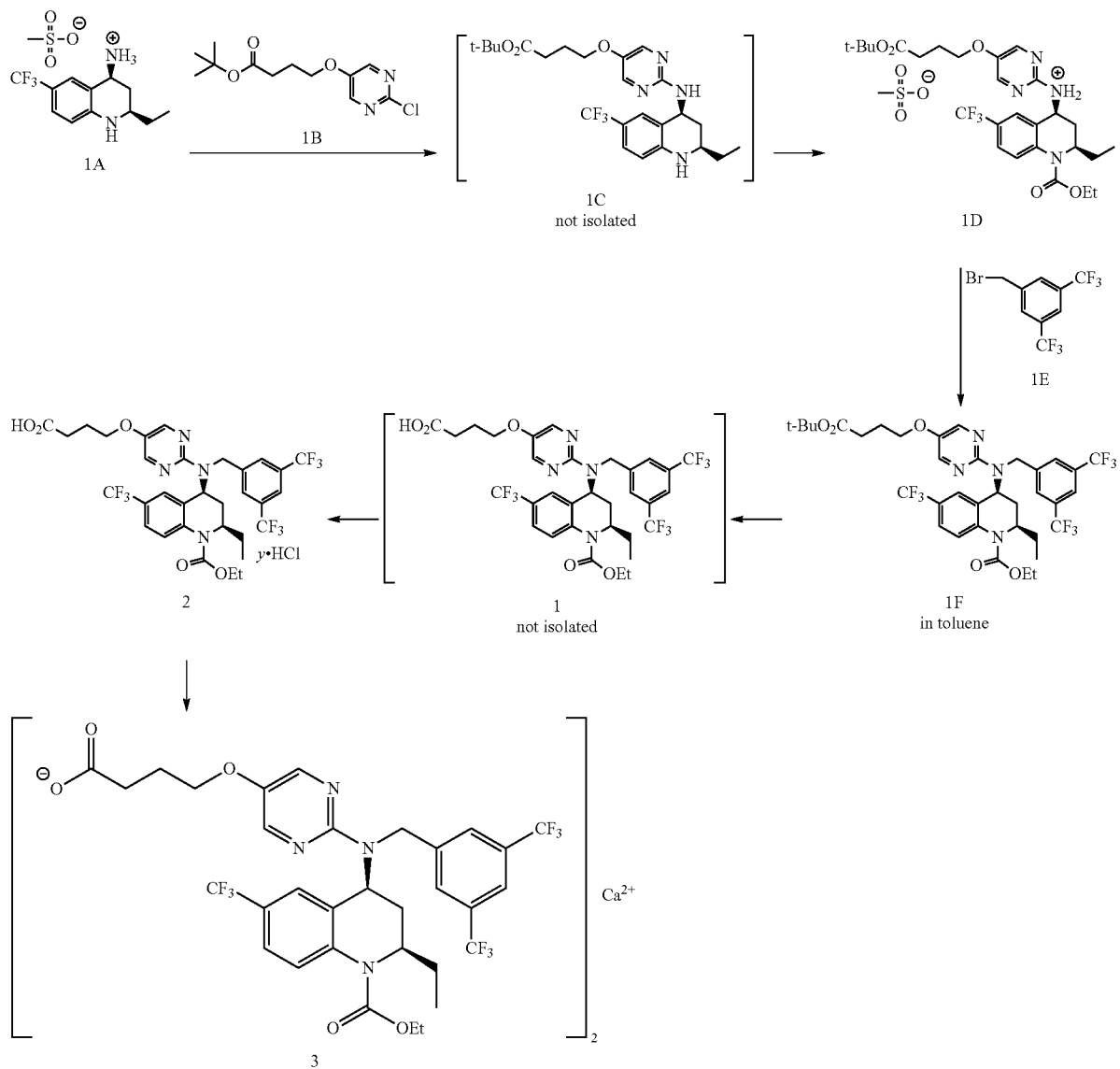

With reference to Scheme 1, amorphous obicetrapib hemicalcium (compound 3) was prepared in six chemical steps and three isolations from the mesylate salt of (2R,4S)-4-amino-2-ethyl-6-trifluoromethyl-3,4-dihydro-2H-quinoline (compound 1A), t-butyl-4-(2-chloropyrimidin-5-yloxy)-butyrate (compound 1B), and 3,5-bis(trifluoromethyl)benzyl bromide (compound 1E). Compound 1A was coupled with compound 1B through a palladium-catalyzed reaction to produce a solution of (2R,4S)-4-[5-(3-t-butoxycarbonylpropoxy)pyrimidin-2-yl)]amino-2-ethyl-6-trifluoromethyl-3,4-dihydro-2H-quinoline (compound 1C), which was not isolated but directly reacted with excess ethyl chloroformate in the presence of pyridine to produce (2R,4S)-4-[5-(3-t-butoxycarbonylpropoxy)pyrimidin-2-yl)]amino-2-ethyl-6-trifluoromethyl-3,4-dihydro-2H-quinoline-1-carboxylic acid ethyl ester, which was isolated as a crystalline mesylate salt (Compound 1D). The crystalline mesylate salt, Compound 1D was alkylated with 3,5 bis(trifluoromethyl)benzyl bromide (compound 1E) under strongly basic conditions to produce a solution of (2R,4S)-4-{[3,5-bis(trifluoromethyl)benzyl]-[5-(3-t-butoxycarbonylpropoxy) pyrimidin-2-yl]amino}-2-ethyl-6-trifluoromethyl-3,4-dihydro-2H-quinoline-1-carboxylic acid ethyl ester (compound 1F) in toluene. Compound 1F was then subjected to an acidic cleavage of the tert-butyl ester to produce a solution of (2R,4S)-4-{[3,5-bis(trifluoromethyl) benzyl]-[5-(3-carboxypropoxy)pyrimidin-2-yl]amino}-2-ethyl-6-trifluoromethyl-3,4-dihydro-2H-quinoline-1-carboxylic acid ethyl ester (compound 1). Compound 1 was then converted to compound 2, which is a solvate of (2R,4S)-4-{[3,5-bis(trifluoromethyl)benzyl]-[5-(3-carboxypropoxy)pyrimidin-2-yl]amino}-2-ethyl-6-trifluoromethyl-3,4-dihydro-2H-quinoline-1-carboxylic acid ethyl ester (compound 2). Finally, compound 2 was converted to the amorphous hemicalcium salt (compound 3) and milled to the target particle size. Compound 2 is crystalline obicetrapib HCl and compound 3 is amorphous obicetrapib hemicalcium. An FT-IR spectrum of milled amorphous obicetrapib hemicalcium can be found in FIG. 4. A solution-state $^1$H-NMR spectrum consistent with chemical structure of obicetrapib hemicalcium can be found at FIG. 5.

Each of the steps in the manufacturing process for (2R, 4S)-4-{[3,5-bis(trifluoromethyl)benzyl]-[5-(3-carboxypropoxy)pyrimidin-2-yl]amino}-2-ethyl-6-trifluoromethyl-3,4-dihydro-2H-quinoline-1-carboxylic acid ethyl ester (compound 1), the intermediate HCl intermediate (compounds 2), and the corresponding amorphous calcium salt (compound 3) will be described in more detail in Examples 1-16 below.

Examples 1-3, 5, 7, 9, 11-12 describe a method for manufacturing steps in the process for preparing amorphous obicetrapib hemicalcium (compound 3); and Examples 4, 6, 8, 10 and 13 provide additional methods of preparing the compounds indicated. The methods in these examples sometimes represent more than one batch prepared of the indicated compounds made.

Examples 14-15 describe methods for milling amorphous obicetrapib hemicalcium (compound 3); and Example 16 describes a method for preparing crystalline obicetrapib hemicalcium.

Example 1—Preparation of (2R,4S)-4-amino-2-ethyl-6-trifluoromethyl-3,4-dihydro-2H-quinoline (Compound 1A Free Base)

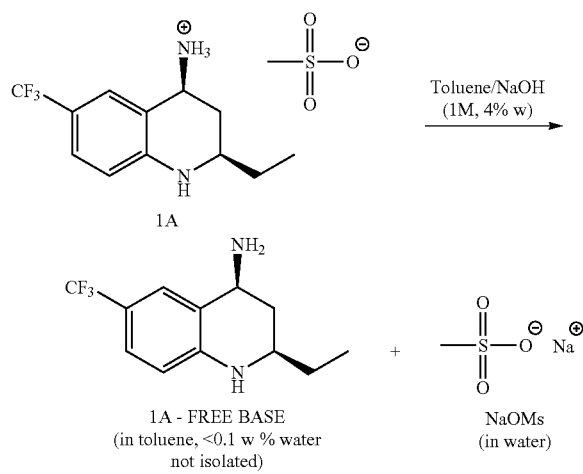

(2R,4S)-4-amino-2-ethyl-6-trifluoromethyl-3,4-dihydro-2H-quinoline (compound 1A) (62 kg, 182 mol, 1.00 equiv.) was added to a reaction vessel fitted with a reflux condenser along with toluene (375 L). The resulting slurry was stirred at 52° C. and 1 M aqueous sodium hydroxide solution (322 L, 5.2 vol.) was added. The reaction mixture was stirred until all solid was dissolved and then cooled to 20° C. The stirring was halted and the reaction mixture was allowed to split into two phases. The bottom aqueous phase was drained, and an aqueous solution of sodium chloride (310 L, 5.0 vol.) was added. The reaction mixture was then stirred at 20° C. for 30 minutes. The stirring was once again halted and the reaction mixture was allowed to split into two phases. The bottom aqueous phase was drained, and deionized water (310 L, 5.0 vol.) was added. The reaction mixture was then stirred at 20° C. for 30 minutes. The stirring was once again halted and the rection mixture was allowed to split into two phases. The bottom aqueous phase was separated. The resulting organic solution was then distilled under vacuum at an internal temperature of 65° C. or less. Distillation was continued until a final visual volume of 4.0 volumes (250 L) was reached. The reaction vessel was then cooled to 20° C. to provide a solution of (2R,4S)-4-amino-2-ethyl-6-trifluoromethyl-3,4-dihydro-2H-quinoline (Compound 1A—FREE BASE) in toluene with a small amount of water present. Compound 1A—FREE BASE was not isolated but used directly in Example 2.

Example 2—Preparation of (2R,4S)-4-[5-(3-t-butoxycarbonylpropoxy)pyrimidin-2-yl)]amino-2-ethyl-6-trifluoromethyl-3,4-dihydro-2H-quinoline (Compound 1C)

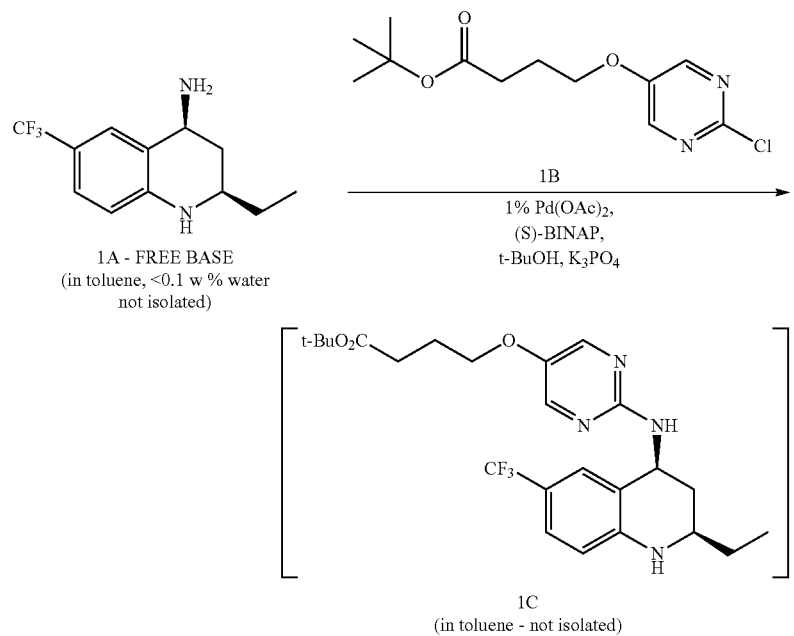

Additional toluene (107 L, 1.5 vol.) was added to the reaction vessel ("vessel A") containing the (2R,4S)-4-amino-2-ethyl-6-trifluoromethyl-3,4-dihydro-2H-quinoline (Compound 1A—FREE BASE) in toluene with <1000 ppm water from the previous step. t-Butyl-4-(2-chloropyrimidin-5-yloxy)-butyrate (compound 1B) (54.6 kg, 200 mol, 1.10 equiv.) was then added to vessel A along with t-BuOH (122 L, 1.55 vol.). The reaction mixture was stirred and sparged with nitrogen. Meanwhile, palladium acetate (410 g, 1.8 mol, 1 mol %) was added under nitrogen to a second reaction vessel ("vessel B"). (S)-BINAP (2.48 kg, 4.0 mol, 2.2 mol %) and toluene (107 L, 1.5 vol.) were further added to vessel B and the resulting mixture was stirred to form a red/orange Pd-BINAP solution. The orange/red Pd-BINAP solution of reaction vessel B was transferred to vessel A. $K_3PO_4$ (85 kg, 400 mol, 2.20 equiv.) was further added to vessel A and the resulting reaction mixture was heated to an internal temperature of 72° C. and stirred for at least 2 hours. The mixture was then cooled to 20° C., deionized water was carefully added (124 L) and the mixture was stirred for 30 minutes. Stirring was then halted and layers were allowed to split into two phases. The bottom aqueous phase was separated, and an aqueous solution of 1M HCl was added (123 L) with stirring. After 30 minutes, the stirring was once again stopped and the layers were allowed to split into two phases. The bottom aqueous phase was separated, and an aqueous solution of sodium chloride (326 kg, 5.26 vol.) was added with stirring. After 30 minutes, the stirring was once again stopped and the layers were allowed to split into two phases. The bottom aqueous phase was separated, and deionized water (248 L, 4.0 vol.) was added with stirring. After 30 minutes, the stirring was once again stopped and the layers were allowed to split into two phases. The bottom aqueous phase was separated. The resulting reaction mixture was then treated with ethylenediamine (1.60 kg, 0.15 equiv.) and stirred at 20° C. for 80 minutes. The reaction mixture was then filtered over a charcoal cartridge and the filtrate returned to a clean vessel. Mixture was then distilled under a partial vacuum at an internal temperature of 60° C. or less. Distillation was continued until approximately 2.50 volumes by visual observation in reactor (155 L) remained, then acetonitrile (394 L, 5.0 vol.) was added. The mixture was then distilled under vacuum at an internal temperature of 60° C. or less. Distillation was continued until approximately 2.50 volumes by visual observation in reactor (155 L), then the contents were cooled to 20° C. The reaction vessel was then charged with acetonitrile (394 L, 5.0 vol. vol., to reach 11 volumes by visual observation (approximately 620 L)) to obtain (2R,4S)-4-[5-(3-t-butoxycarbonylpropoxy)pyrimidin-2-yl)]amino-2-ethyl-6-trifluoromethyl-3,4-dihydro-2H-quinoline (compound 1C) dissolved in acetonitrile. Compound 1C was not isolated but used directly in Example 3.

Example 3—Preparation of (2R,4S)-4-[5-(3-t-butoxycarbonylpropoxy)pyrimidin-2-yl)]amino-2-ethyl-6-trifluoromethyl-3,4-dihydro-2H-quinoline-1-carboxylic acid ethyl ester, as a Crystalline Mesylate Salt (Compound 1D)

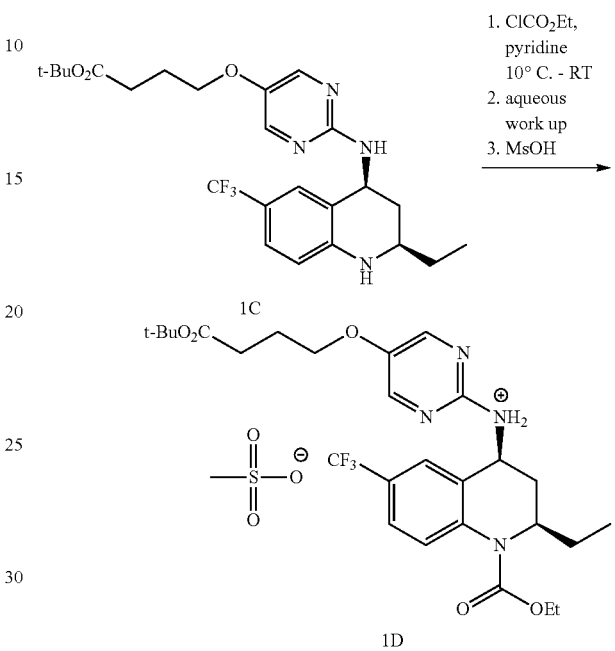

(2R,4S)-4-[5-(3-t-butoxycarbonylpropoxy)pyrimidin-2-yl)]amino-2-ethyl-6-trifluoromethyl-3,4-dihydro-2H-quinoline (compound 1C) in acetonitrile (approximately 620 L) was cooled to an internal temperature of <10° C. and pyridine (72 L, 900 mol, 4.9 equiv.) was added. Ethyl chloroformate (136 L, 1428 mol, 7.84 equiv.) was then added through an addition funnel while keeping the internal temperature of the reactor contents <10° C. The internal temperature of the reaction mixture was then increased linearly to 20° C. over the course of 3.5 hours. The mixture was then distilled under vacuum at an internal temperature of 60° C. or less. Distillation was continued until approximately 2.50 volumes by visual observation (155 L). Isopropyl acetate (471 L, 6.6 vol.) was then added to the reaction vessel and distillation was continued under vacuum at an internal temperature of 60° C. or less until roughly 2.50 volumes remained by visual observation (155 L). Then isopropyl acetate (471 L, 6.6 vol.), 1M hydrochloric acid (307 L, 5.0 vol.), and 26% aqueous sodium chloride (63 L, 1.2 vol.) were added to the reaction vessel. The resulting mixture was stirred for 30 minutes, then separated into two phases. The bottom aqueous phase was separated, and saturated aqueous sodium bicarbonate solution (132 L, 2.3 vol.) was added. The resulting mixture was stirred for 30 minutes, then separated into two phases. The bottom aqueous phase was separated and the remaining mixture was distilled under vacuum and at 60° C. or less to reach a total volume of roughly 4.0 volumes by visual observation (250 L) to obtain (2R,4S)-4-[5-(3-t-butoxycarbonylpropoxy)pyrimidin-2-yl)]amino-2-ethyl-6-trifluoromethyl-3,4-dihydro-2H-quinoline-1-carboxylic acid ethyl ester (corresponding free base of Compound 1D) in isopropyl acetate based on the weight of the solution.

Additional isopropyl acetate (86 L, 1.4 vol.) and methyl t-butylether (MTBE, 593 L, 9.6 vol) were added to (corresponding free base of Compound 1D) in isopropyl acetate and the jacket temperature was set to 20° C. Methanesulfonic acid (MsOH, 17.6 kg, 1.0 equiv. based on mmol of compound (corresponding free base of Compound 1D) was then added to the reaction mixture over 60 minutes. The resulting slurry was then agitated for 8 hours. The slurry was then filtered under vacuum at 20° C. The solid cake was then washed with 75/25 v/v isopropyl acetate (78 L, 1.1 vol.) and methyl t-butyl ether solution (236 L, 2.8 vol.) then dried under vacuum and at 20° C. to obtain isolated (2R,4S)-4-[5-(3-t-butoxycarbonylpropoxy)pyrimidin-2-yl)]amino-2-ethyl-6-trifluoromethyl-3,4-dihydro-2H-quinoline-1-carboxylic acid ethyl ester, as a crystalline mesylate salt (Compound 1D) with a yield of 74%, based on the number of moles of compound 1A. The purity of the crystalline Compound 1D obtained was >99%.

Example 4—Additional Preparation of Compound 1C and Compound 1D

The preparation described below was generally used to prepare multiple batches of Compound 1C and Compound 1D. In some preparations, for example, seeding with Compound 1D was done and others not as further discussed below.

Pd(OAc)$_2$ and (S)-BINAP were dissolved in toluene and stirred to form the corresponding Pd-BINAP-complex (color change to red) (the "catalyst solution"). Toluene, Compound 1B, Compound 1A and K$_3$PO$_4$ were added to the reactor and stirred. A target content for water is on the order of 6%. Catalyst solution was added to the reactor mixture, and the reaction mixture was heated up to 70-75° C. and stirred.

After washing with HCl, brine and water, subsequent phase separation, EDA and toluene were charged and the solution was stirred for approximately 90 min. The solution was passed via a cartridge loaded with activated carbon (Begerow, F-9120) for removing palladium. Afterwards, the solvent was switched from toluene to acetonitrile (MeCN) by distillation to obtain Compound 1C.

To the Compound 1C solution, pyridine was added and cooled to lower than 10° C. prior to ethyl chloroformate addition. Ethyl chloroformate was dosed in one or two portions to the Compound 1C solution, while the temperature was controlled to NMT 10° C. The reaction mixture was then stirred for approximately 1 hour at 17-27° C., converting Compound 1C to the free base of Compound 1D (Compound 1D-FB). A solvent switch from acetonitrile to isopropyl acetate (iPrOAc) was done by distillation, and the organic phase was washed with HCl (1 M), brine and aqueous NaHCO$_3$(NaOH may also be used) followed by volume reduction by distillation.

To the Compound 1D-FB solution in iPrOAc, methanesulfonic acid (MsOH) and MTBE was added and stirred. In some cases, previously made seed crystals of Compound 1D were added, but that is not required. Whether seeds are added or not, crystallization of Compound 1D followed. The solid product was filtered, washed with MTBE/iPrOAc (75/25) and dried on a filter.

Example 5—Preparation of (2R,4S)-4-{[3,5-bis (trifluoromethyl)benzyl]-[5-(3-tbutoxycarbonyl-propoxy) pyrimidin-2-yl]amino}-2-ethyl-6-trifluoromethyl-3,4-dihydro-2Hquinoline-1-carboxylic acid ethyl ester (Compound 1F)

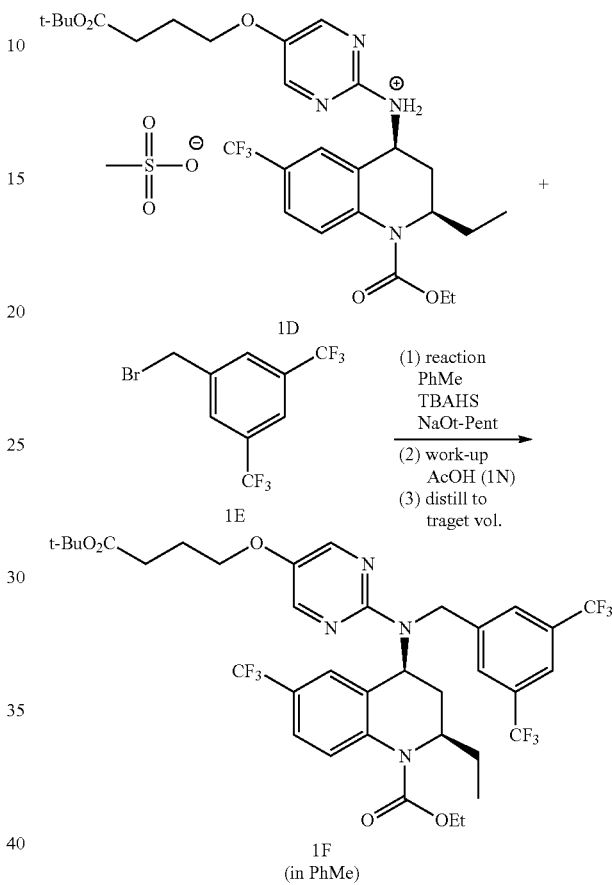

(2R,4S)-4-[5-(3-t-butoxycarbonylpropoxy)pyrimidin-2-yl)]amino-2-ethyl-6-trifluoromethyl-3,4-dihydro-2H-quinoline-1-carboxylic acid ethyl ester, as a crystalline mesylate salt (Compound 1D) (42 kg) and toluene (465 kg, 12.7 vol.) was added to a reaction vessel at a temperature of 5° C. Tetrabutylammonium hydrogensulfate (3.5 kg, 0.16 equiv.) and sodium tert-pentoxide (34.5 kg, 4.8 equiv.) were then added and the resulting reaction mixture was stirred for 10 minutes and degassed with nitrogen. 3,5-bis(trifluoromethyl)benzyl bromide (Compound 1E) (28 kg, 1.41 equiv.) was then added to the reaction mixture and stirring was continued for 6.5 hours at 5° C. The reaction mixture was then treated with iN acetic acid solution (320 kg) and allowed to stir for approximately 30 minutes at 20° C. After which time, the stirring was stopped and the mixture was allowed to separate into two phases. The lower aqueous phase was discarded and the reaction mixture was concentrated under vacuum at an internal temperature 60° C. or less until approximately 3.3 volumes (137 L) remained, to obtain a solution of 36.8 weight percent (2R,4S)-4-{[3,5-bis(trifluoromethyl)benzyl]-[5-(3-tbutoxycarbonylpropoxy) pyrimidin-2-yl]amino}-2-ethyl-6-trifluoromethyl-3,4-dihydro-2Hquinoline-1-carboxylic acid ethyl ester (Compound 1F) in toluene, based on the weight of the solution, 97% yield based on the number of moles of Compound 1D).

Example 6—Additional Preparation of Compound 1F

Compound 1E was charged to a toluene solution containing Compound 1D and tetrabutylammonium hydrogensulfate. Under cooling, sodium tert-pentoxide in toluene was added. The resulting reaction mixture was quenched with dilute acetic acid. The aqueous layer was separated and the product in the toluene layer was treated with charcoal and concentrated in vacuum (Compound 1F.)

Example 7—(2R,4S)-4-{[3,5-bis(trifluoromethyl)benzyl]-[5-(3-carboxypropoxy)pyrimidin-2-yl]amino}-2-ethyl-6-trifluoromethyl-3,4-dihydro-2H-quinoline-1-carboxylic acid ethyl ester (Compound 1)

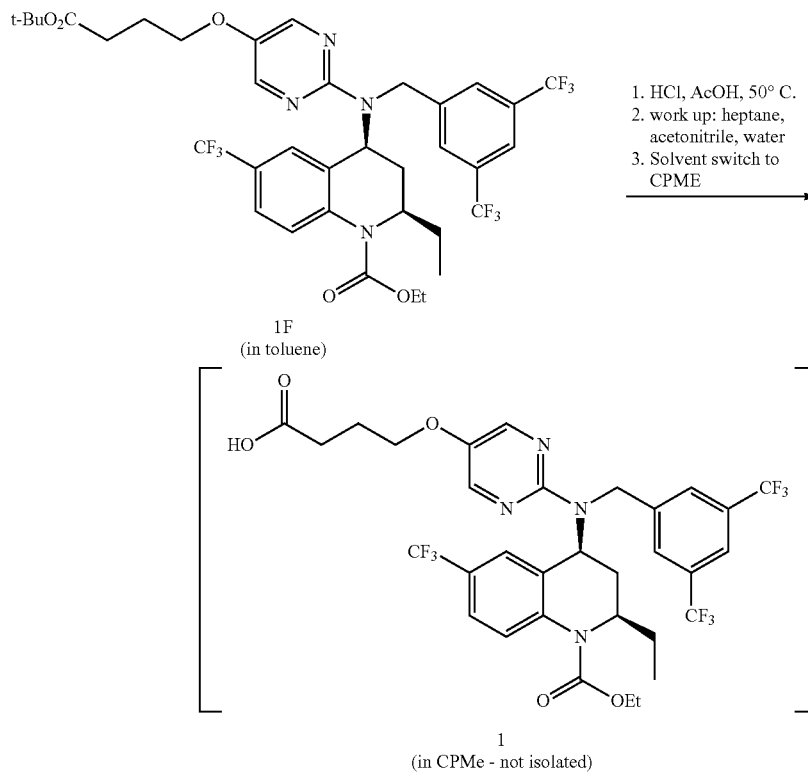

A solution of 37 wt. % (2R,4S)-4-{[3,5-bis(trifluoromethyl)benzyl]-[5-(3-tbutoxycarbonylpropoxy)pyrimidin-2-yl]amino}-2-ethyl-6-trifluoromethyl-3,4-dihydro-2Hquinoline-1-carboxylic acid ethyl ester (compound 1F) in toluene (128.4 kg of the 37 wt. % solution, equivalent to 47.5 kg compound 1F) was diluted to 32 wt % with additional toluene and then mixed with acetic acid (253 kg, 5.33 wt.), and 6 M HCl (109.9 kg, 2.32 wt, prepared in situ with 66.1 kg of conc. HCl and 43.8 kg of water). The resulting reaction mixture was vigorously agitated and warmed to 48° C. for 3 hours. The reaction mixture was then cooled to 21° C., then n-heptane (159.8 kg, 3.36 wt.), acetonitrile (73.8 kg, 1.55 wt.) and water (170 kg, 3.58 wt.) were added. The resulting mixture was agitated for 34 minutes and then allowed to separate into two phases. The lower aqueous phase was then further treated with water (90 kg, 1.89 wt.), n-heptane (95 kg, 2.00 wt.), acetonitrile (38 kg, 0.80 wt.) and toluene (42 kg, 0.88 wt.) and once again agitated for 20 minutes before separating the organic phase and discharging the lower aqueous phase. The combined organic phases were then treated with water (240 kg, 5.05 wt.) and agitated for an additional 30 minutes before separating into two phases. The lower aqueous phase was discarded and the upper organic phase was treated with 5% w/w sodium citrate tribasic dihydrate (34 kg, 0.72 wt.) and water (205 kg, 4.32 wt.). The resulting mixture was vigorously agitated for 30 minutes and then allowed to separate into two phases before discarding the lower aqueous phase. The remaining organic phase was treated once again with water (240 kg, 5.05 wt.) and agitated for 30 minutes before allowing to separate into two phases and discharging the lower aqueous phase. The organic phase was then concentrated to approximately 3 volumes (approximately 149 L) in-vacuo maintaining an internal temperature of 50° C. or less. The reaction mixture was diluted with cyclopentyl methyl ether (CPME, 250 kg, 5.26 wt.) and agitated. The solution was then concentrated to approximately 3 volumes (approximately 165 L) in-vacuo maintaining an internal temperature of 50° C. or less. CPME (250 kg, 5.26 wt.) was then added and the mixture concentrated to approximately 2.5 volumes (approximately 124 L) in-vacuo, maintaining an internal temperature of 50° C. or less to obtain a solution of 33.7 weight percent of (2R,4S)-4-{[3,5-bis(trifluoromethyl)benzyl]-[5-(3-carboxypropoxy)pyrimidin-2-yl]amino}-2-ethyl-6-trifluoromethyl-3,4-dihydro-2H-quinoline-1-carboxylic acid ethyl ester (compound 1, free base form) in cyclopentyl methyl ether (CMPE) having 1 weight percent toluene, less than 1 weight percent n-heptane, based on the weight of the solution.

Example 8—Additional Preparation of Compound 1

Compound 1F (in solution in toluene) was mixed with acetic acid and 6 M aq. HCl. The biphasic mixture was intensively stirred at 45-50° C. and subsequently cooled to 20° C. After addition of water, acetonitrile and n-Heptane, the mixture was extracted, and the layers were separated.

The aqueous layer of the first extraction was diluted with water and extracted with Acetonitrile, n-heptane, and toluene a second time. The two obtained organic extracts were combined. The organic phase was washed with water and 5% sodium citrate solution added so that the pH was >3.5. A water wash was performed, and the organic layer was treated with activated charcoal. A solvent switch from toluene and n-Heptane to CPME was performed by repeated vacuum distillation and charging CPME to obtain Compound 1.

Example 9—(2R,4S)-4-{[3,5-bis(trifluoromethyl)benzyl]-[5-(3-carboxypropoxy)pyrimidin-2-yl]amino}-2-ethyl-6-trifluoromethyl-3,4-dihydro-2H-quinoline-1-carboxylic acid ethyl ester hydrochloride (Compound 2)

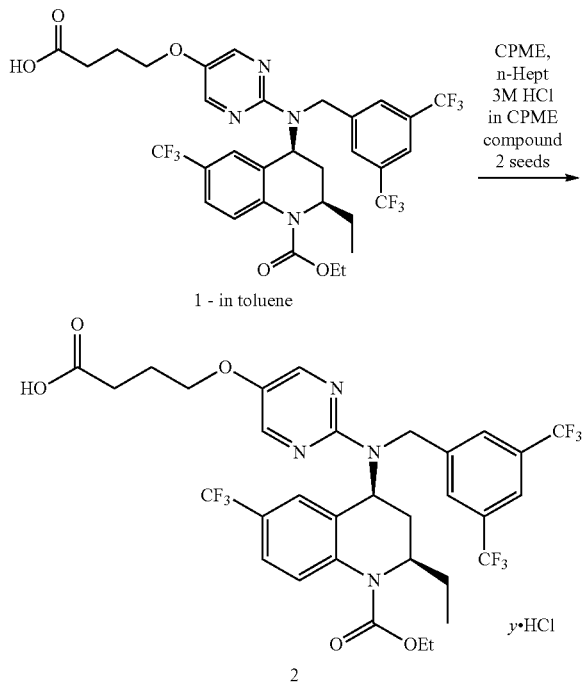

The 33.7 weight percent solution of (2R,4S)-4-{[3,5-bis(trifluoromethyl)benzyl]-[5-(3-carboxypropoxy)pyrimidin-2-yl]amino}-2-ethyl-6-trifluoromethyl-3,4-dihydro-2H-quinoline-1-carboxylic acid ethyl ester (compound 1, free base form, 115.6 kg, 59.2 mol) in cyclopentyl methyl ether (CPME) from the previous step was added to a clean reaction vessel under nitrogen with a jacket temperature of 22° C. After dilution with CPME (27.8 kg/0.58 wt.), n-heptane was then added (54.8 kg, 1.15 wt.) and the internal reaction temperature was increased to 39° C. 3.0 M HCl in CPME (17.6 kg, 0.37 wt.) was then added at a constant rate while maintaining an internal reaction temperature of 39° C. After the addition of HCl was complete, the internal temperature was increased to 52° C. Additional n-heptane was then added (133.2 kg, 2.80 wt.) at a constant rate while maintaining an internal reaction temperature of 51° C. The reaction mixture was heated to 55° C. and then it was cooled to 49° C. An aliquot of the reaction mixture was removed, cooled to 11° C. at a linear cooling rate until a slurry formed containing crystals of compound 2 in CPME/n-heptane (referred to herein as "seed crystal slurry"). A seed crystal slurry of compound 2 (169 g, 0.43 weight percent) in CPME/n-heptane was then added at 49° C. and this temperature was held for 105 minutes. The opaque reaction mixture was then cooled to 11° C. over the course of 12 hours at a linear cooling rate. The reaction mixture was then filtered under vacuum at 11° C. to collect the solid wet HCl intermediate (compound 2). A mixture of CPME and n-heptane (56.6 kg CPME, 179 kg n-heptane) was then added to the reaction vessel and cooled to 11° C. Half the mixture was then poured through the filter dryer as a chromatography wash. The second half was passed through the filter as a slurry wash. Compound 2 was not unloaded from the filter dryer but was further purified by recrystallization according to the following procedure.

Compound 2 in cyclopentyl methyl ether (CPME) (77.6 kg) was added into a filter dryer containing compound 2 and heated to 25° C. The dissolved compound 2 was then transferred to a reaction vessel with a reactor jacket temperature set at 25° C. under nitrogen, and the internal temperature was increased to 38° C. 3.1 M HCl in CPME (6.4 kg) was added so that a total of 1.07 equiv. HCl was achieved based on assay of compound 1 in compound 2 crude and assay of HCl in compound 2 crude. n-Heptane was then added (139.4 kg and the internal reaction temperature was increased to 51° C. A seed crystal slurry of compound 2 (291 g, 0.87 weight percent) in CPME/n-heptane was then added at 50° C. and this temperature was held for 105 minutes. The opaque reaction slurry was then cooled to 11° C. over 12 hours at a linear cooling rate. The slurry was then filtered under vacuum at 9° C. using a filter dryer. 20 vol. % of CPME in n-heptane (57.4 kg CPME, 180 kg n-heptane) was then added to the reaction vessel and cooled to 11° C. Half the mixture was then poured through the filter dryer as a chromatography wash. The second half was passed through the filter dryer as a slurry wash. The wet filter cake was then dried in vacuo in steps of jacket temperature 25, 35, 46, 54° C. to provide compound 2 in 64% yield (from compound 1F) with 99.6 area % purity and residual solvents 0.3% w CPME and <0.1% w n-heptane.

Example 10—Additional Preparation of Compound 2

Compound 1 in solution was further diluted with n-Heptane and heated to 40° C. At this temperature approximately 3 M HCl in CPME (1.1 meq regarding Compound 1F) were added. The solution was further heated to 48-53° C. and a second portion of n-Heptane was charged. The clear solution was cooled to 53° C. for optional seeding with Compound 2 seeding crystals (seeding is optional but preferred in a manufacturing context). If seeded, the solution is desaturated at 53° C. and then cooled to 10° C. over 12 hours.

A crystal curing procedure (a repeated heating and cooling cycle procedure) can be performed to improve the color of the resulting filtered Compound 2. The product suspension was filtered, washed once with cooled CPME/n-Heptane (20:80 vol) and once with cooled n-Heptane and then dried in vacuum.

Example 11—(2R,4S)-4-{[3,5-bis(trifluoromethyl)
benzyl]-[5-(3-carboxypropoxy)pyrimidin-2-yl]
amino}-2-ethyl-6-trifluoromethyl-3,4-dihydro-2H-
quinoline-1-carboxylic acid ethyl ester (Compound
3)

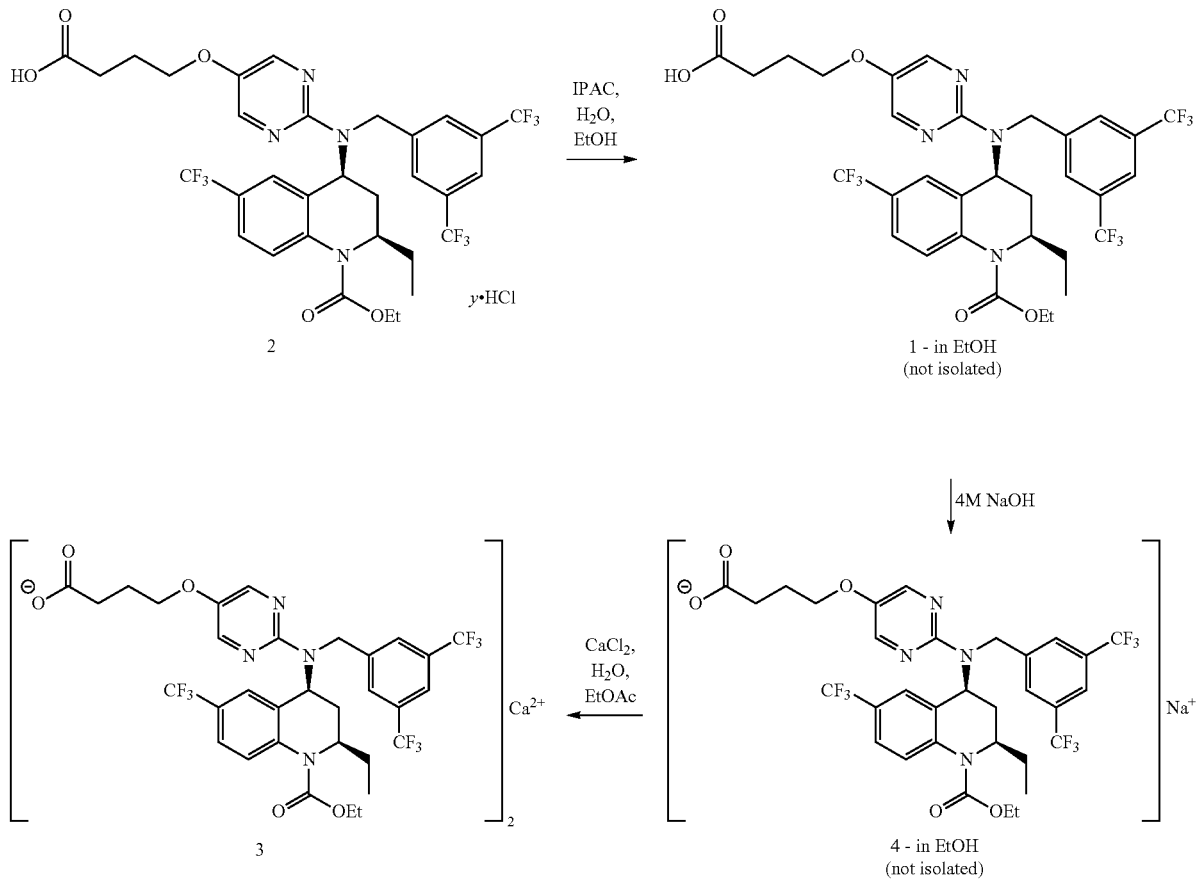

(2R,4S)-4-{[3,5-bis(trifluoromethyl)benzyl]-[5-(3-carboxypropoxy)pyrimidin-2-yl]amino}-2-ethyl-6-trifluoromethyl-3,4-dihydro-2H-quinoline-1-carboxylic acid ethyl ester hydrochloride (compound 2,35.0 kg, 48.4 mol) was added to isopropyl acetate (IPAC, 214 kg, 6.11 wt.) to an inert reactor and stirred at 22° C. to achieve dissolution. Deionized water (245 kg, 7.00 wt.) was added, the reaction mixture was stirred at 23° C. for 35 minutes, then the stirring was stopped, the phases were separated, and the lower aqueous phase was removed. The process of adding deionized water (245 kg, 7 wt.), stirring, and removing the lower aqueous phase was repeated further 3 times. The organic phase was then concentrated under reduced pressure to approximately 71 L (approximately 2 vol.) maintaining an internal temperature of 55° C. or less. Ethanol (115 kg, 3.29 wt.) was then added, and the reaction mixture was concentrated under reduced pressure to approximately 78 L (approximately 2 vol.) maintaining an internal temperature of 55° C. or less. The process of adding ethanol (115 kg, 3.29 wt.) and concentrating was repeated twice more. The reaction mixture was then cooled to 25° C. and subjected to a charcoal treatment via a cartridge. The cartridge was then rinsed with ethanol (100 kg, 2.86 wt.) and concentrated to 147 L (approximately 3.8 vol.) at 55° C. or less in vacuo followed by addition of 35 L of EtOH (1.0 vol.) to provide the free base form of (2R,4S)-4-{[3,5-bis(trifluoromethyl)benzyl]-[5-(3-carboxypropoxy)pyrimidin-2-yl]amino}-2-ethyl-6-trifluoromethyl-3,4-dihydro-2H-quinoline-1-carboxylic acid ethyl ester (compound 1) in ethanol. The 14% wt. NaOH solution (15.8 kg, 1.13 eq.) was then added to the reaction vessel containing compound 1 in ethanol maintaining a reaction temperature of 20° C. The reaction mixture was stirred at 20° C. for 5 hours to achieve full conversion.

34% wt. Calcium chloride (aq.) (10.8 kg) was added to an inert reactor. Deionized water (336 L, 9.61 wt. relative to compound 1) and ethyl acetate (15 kg, 0.43 wt. relative to compound 1) was then added and the mixture was stirred for 30 minutes to provide "Solution B."

Solution B was then cooled to 9° C. with agitation. Solution A (see above) was then added via a filter to Solution B over 90 minutes, maintaining a temperature of 10° C. The Solution A vessel was then rinsed forward to solution B with additional ethanol (50 kg, 1.43 wt. relative to compound 1). The resulting slurry was stirred for 1 hour at 9° C. The solids were then collected by filtration and rinsed with deionized water (2×175 kg, 5 wt. relative to compound 1). The solids were then dried in vacuo at 50° C. for 21 hours to obtain 27.6 kg of amorphous obicetrapib hemicalcium (compound 3) with <1 weight percent water (77% yield, based the number of moles of compound 2). The compound 3 was reworked as described below in Example 12.

Example 12—Rework of Compound 3

Compound 3 (27.6 kg) was dissolved in ethanol (55.2 kg 2 wt. relative to compound 3) at 45-48° C. and subsequently cooled to 11° C. The solution was filtered into a pre-cooled (approximately 10° C.) mixture of an aqueous $CaCl_2$) solution (8.2 kg of 33-35 weight percent, 0.3 wt.), water (262 kg, 9.5 wt.) and ethyl acetate (12.6 kg, 0.46 wt.). The resulting suspension was filtered off and washed with water (2×5 wt., 138 kg per washing step) and the solid was dried in vacuo maintaining an internal temperature of 45° C. or less for 23 hours to obtain 24.8 kg (91% yield) of the amorphous hemicalcium salt of (2R,4S)-4-{[3,5-bis(trifluoromethyl)benzyl]-[5-(3-carboxypropoxy)pyrimidin-2-yl]amino}-2-ethyl-6-trifluoromethyl-3,4-dihydro-2H-quinoline-1-carboxylic acid ethyl ester (compound 3) with <1 weight percent water and a purity of 97.5% wt. and >99.9 area %.

Example 13—Additional Preparation of Compound 3

Compound 2 was neutralized and dissolved with aqueous NaOH in EtOH. The solution was filtered through activated carbon. Vacuum distillation was performed to concentrate the solution. Aqueous NaOH solution was dosed to obtain the sodium salt of Compound 1 in solution and for saponification of esters, which were formed in this and previous steps.

Subsequently, a mixture of aqueous $CaCl_2$) solution and EtOAc was prepared in a second vessel. The Na-salt of Compound 1 from the first vessel was then dosed into this mixture, whereby Compound 3 precipitated. Optionally, the suspension may be heated to NMT 25° C. and subsequent cooled to 8° C. The solid Compound 3 was filtered off at 8° C., washed with water and dried in vacuo.

Example 14—Milling of Reworked Compound 3

Compound 3 was jet-milled using an 8-inch spiral mill. Feed rate, venturi pressure, and mill pressure were adjusted within the ranges listed below to allow the production of micronized compound 3 in compliance with particle size acceptance criteria (D90=6-15 μm).

Feed rate: 17-20 kg/h
Mill pressure: 20 PSI/1.4 bar
Venturi pressure: 100 PSI/6.9 bar
Process gas: Nitrogen
Analytics: Mastersizer 3000.

Example 15—Milling of Another Compound 3 Preparation

Particle size distribution was adjusted via micronization on a Spiral Jetmill, 8 inch Jet Mill, 8005 and KT4 LIW feeder to target parameters d90: 6-15 microns. Three samples were jet milled with the following results:

d90: 8 microns, 8 microns, and 9 microns
d50: 4 microns, 3 microns, and 4 microns
d10: 2 microns, 1 micron, 1 micron

Example 16—Crystalline Obicetrapib Hemicalcium 2 g of amorphous obicetrapib hemicalcium was added to Acetonitrile (ACN)/Methyl tert butyl ketone (MIBK), 6:1 ratio at 200 mg/ml and the sample was heated to 50° C. for 5 minutes, until all the solids dissolved. The sample was then placed in a water bath and cooled from 50° C. to 5° C. over 48 hours at 0.9° C./min. The samples were kept at 5° C. for 3 days and then transferred to −20° C. for 30 mins prior to isolation of solids. The solids were air dried for 2 hours prior to further characterization. The process resulted in the formation of crystalline obicetrapib hemicalcium.

Example 17—Polarized Light Microscopy (PLM)

Polarized light microscopic pictures were captured using a Nikon DS-Fi2 upright microscope at room temperature. Samples (2 mg) were mounted on a glass slide and covered with a drop of silicone oil with a cover slip on top of the sample for analysis. Samples were not protected from light.

Example 18—X-ray Powder Diffraction (XRPD)

XRPD was performed with Panalytical X'Pert[3] Powder diffractometer using an incident beam of Cu radiation produced using an Empyran tube, fine focused source, on a silicon zero-background holder. Prior to the analysis, a silicon standard (NIST SRM 640d) was analyzed to verify that the Si 111 peak position is consistent with the NIST-certified position. Approximately 5 to 10 mg of sample was placed on a silicon zero-background holder and flattened manually using an aluminum spatula to minimize difference in the overall sample height. The holder was then loaded on the instrument for analysis. The XRPD parameters used are listed in in Table 10.

TABLE 10

| Parameters for XRPD test | |
|---|---|
| Parameters | Reflection Mode |
| X-Ray wavelength | Cu, kα |
|  | Kα1 (Å): 1.540598, |
|  | Kα2 (Å): 1.544426, |
|  | Kα2/Kα1 intensity ratio: 0.50 |
| X-Ray tube setting | 45 kV, 40 mA |
| Divergence slit | Fixed ⅛° |
| Scan mode | Continuous |
| Scan range (°2TH) | 3-40 |
| Scan step time [s] | 18.87 |
| Step size (°2TH) | 0.0131 |
| Test Time | 4 min 15 s |

Example 19—X-ray Powder Diffraction Pattern

A PANalytical x-ray powder diffractometer was used with the following measurement conditions, with data acquisition by DataViewer and data evaluation by X'Pert High Score Plus:

| | |
|---|---|
| X-ray tube | Cu LFF HR |
| Geometry | Transmission |
| X-ray mirror | Focusing X-ray mirror W/Si |
| Soller slit | 0.02 rad |
| Detector | Pixel 1D |
| Detector active length | 1.69° |
| Divergence slit | Fixed |
| Divergence slit size | ½° |
| X-ray tube excitation | 40 mA, 40 kV |
| 2Theta range | 2° to 40° |
| Measurement mode | Continuous |
| Time per Step | 300 s |
| Step size | 0.013° (2Theta) |
| Rotation | 1 Rev/s |

Example 20—X-ray Powder Diffraction Pattern

The diffraction pattern for FIG. 3 was measured using an Empyrean powder diffractometer in transmission mode from Malvern PANalytical. The sample was prepared as a thin layer between two Kapton foils and measured in continuous mode. The detector measures from approx. 2° 2θ to 40° 2θ. Peaks can be seen at signals at about 3.4° 2θ, about 7.0° 2θ and about 9.2° 2θ. The peak at about 5.6° 2θ is assigned to Kapton foil.

Example 21—X-ray Powder Diffraction Methodology for Crystalline Obicetrapib HCl/Compound 1D Diffraction patterns were measured using a Thermo Fisher Scientific ARL Equinox 1000 powder diffractometer. The diffractometer is equipped with a copper source and a germanium (111) monochromator providing monochromatic Cu Kα1 radiation, and a position sensitive gas-ionization detector.

Samples were measured in reflection mode using an Al sample holder without any further preparation (i.e., grinding). The detector measures over the entire angle range from approx. 2° 2θ to 120°2θ simultaneously; in the case of HCl obicetrapib, discernible signals useful for phase identification are seen up to approx. 45° 2θ. The temperature in the diffractometer is typically around 30° C. during measurements.

Example 22—X-ray Powder Diffraction Methodology for Crystalline Obicetrapib HCl A Rigaku SmartLab X-Ray Diffractometer was configured in Bragg-Brentano reflection geometry equipped with a beam stop and knife edge to reduce incident beam and air scatter. Data collection parameters are shown in Table 11.

TABLE 11

X-Ray Powder Diffraction Parameters

| Parameter | Value | Parameter | Value |
|---|---|---|---|
| Geometry | Bragg-Brentano | Receiving Slit 1 (mm) | 18 |
| Tube Anode | Cu | Receiving Slit 2 (mm) | open |
| Tube Type | Long Fine Focus | Start Angle 2θ (°) | 2 |
| Tube Voltage (kV) | 40 | End Angle 2θ (°) | 40 |
| Tube Current (mA) | 44 | Step Size (°) | 0.02 |
| Detector | D/teX Ultra 250 (XR1 or XR5) HyPix-3000 (XR4) | Scan Speed (°/min) Spinning (rpm) Sample Holder | 6 11 Low-background Si |
| Monochromator | Ni foil Cu Kβ Filter | | |
| Incident Slit (°) | ⅓ | | |

Example 23—FT-IR Spectroscopy

Figure 4:
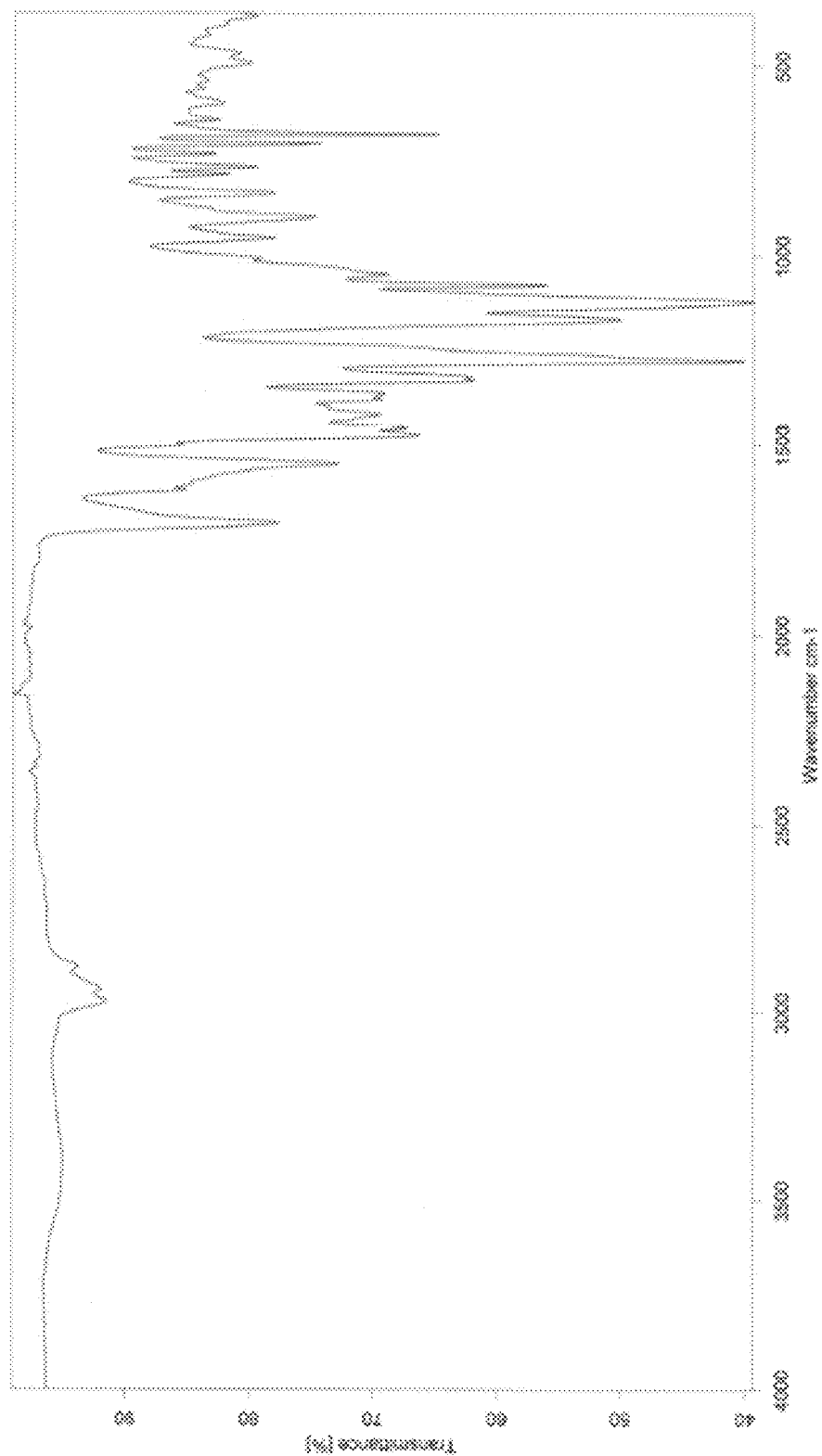
FIG. 4 is an infrared spectrum of amorphous obicetrapib hemicalcium.

The FTIR spectrum a sample of amorphous obicetrapib hemicalcium is set forth in FIG. 4. The FTIR spectrum was acquired using a Bruker Tensor 27 spectrometer with a Platinum ATR-QL-Diamond unit. The milled sample was placed onto the ATR unit without any pretreatment.

Example 24 $^1$H-NMR Spectroscopy

Figure 5:
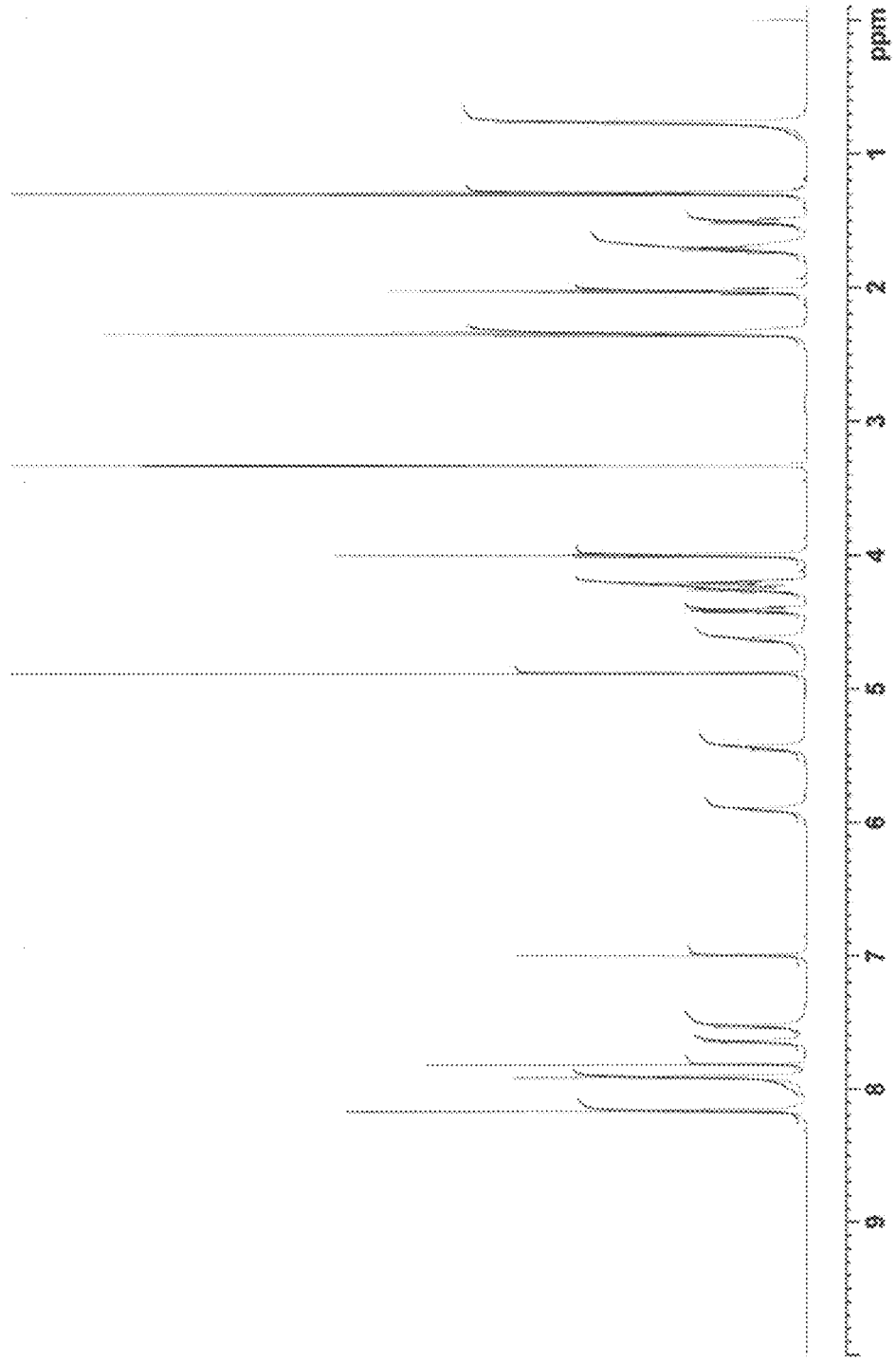
FIG. 5 is a $^1$H-NMR spectrum of amorphous obicetrapib hemicalcium.

The NMR spectra of a solution made from a sample of amorphous obicetrapib hemicalcium is set forth in FIG. 5. The NMR spectrum was obtained using a 600 MHz AVANCE NEO Bruker and in deuterated MeOH as solvent using tetramethylsilane (TMS) as the internal reference for chemical shift at 0.0 ppm. The spectral shifts are consistent with the chemical structure.

Example 25—Modulated Differential Scanning Calorimetry (mDSC)

Figure 14:
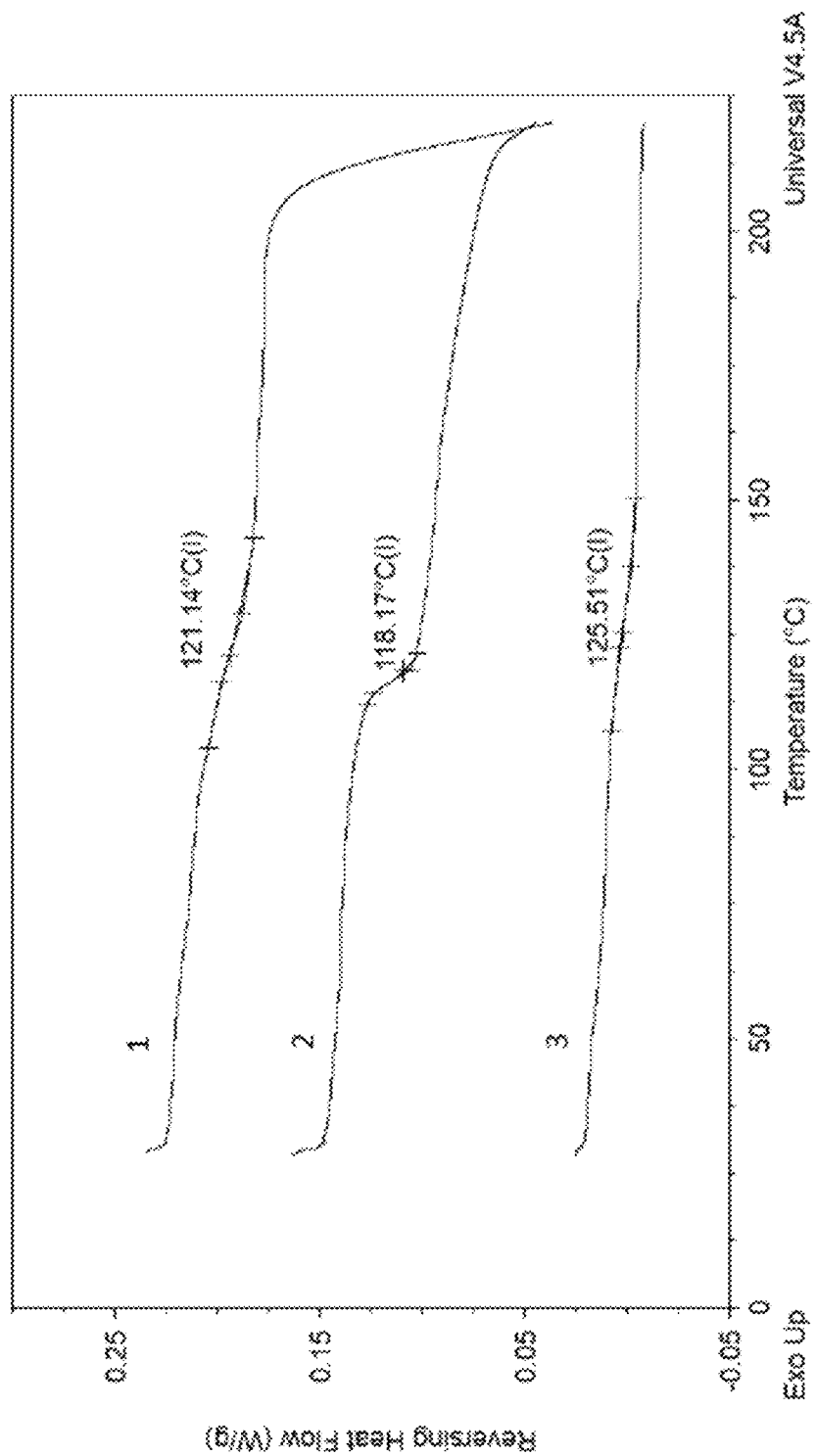
FIG. 14 is a modulated differential scanning calorimetry thermogram (with pinhole) of crystalline obicetrapib hemicalcium.

Samples with mDSC thermograms are set forth at FIG. 12 and FIG. 14 were prepared with Tzero aluminum pan with a pinhole. The ramp rate was from 25° C. to 225° C. at 2° C./min with modulation of ±0.5° C. every 60 seconds. The Instrument used was a TA Q2500 DSC from TA Instruments.

Example 26-Modulated Differential Scanning Calorimetry (mDSC)

Using a TA Instruments DSC2500, the starting temperature was 25° C. and the sample was heated with 2° C. per minute, modulating by ±0.5° C. every 60 seconds up to 225° C. Tzero aluminium pans and Tzero hermetic lids with factory pinholes, which were additionally pierced through and enlarged, were employed for this testing. An integrated thermogram (displaying reversing heat flow) from the sample is included in FIG. 13. The sample exhibited a glass transition with a Tg of approx. 111° C.

Example 27—Methods to Assess Stability

Stability study was conducted on crystalline and amorphous forms of obicetrapib at 70° C./75% relative humidity (RH). The solids were placed into a 4.0 ml glass vial without caps (open condition) and stored at 70° C./75% RH. Samples were pulled out of the stability chamber at day 1 (24 hours) and at 7-day time point. The solids were analyzed by XRPD for physical stability and by HPLC for chemical purity. The sample collected at each time point was dissolved in methanol before HPLC analysis. In order to minimize the effect of potential analyte adsorption on the filter, the initial 0.5 mL of supernatant passing through the filter was discarded prior to collecting sample for HPLC analysis. Purity for each sample was determined based on peak area percent and compared to the sample at T=0.

Example 28—Method Used to Assess Kinetic Solubility in Biorelevant Media

Kinetic solubility study was conducted on crystalline and amorphous forms of obicetrapib in biorelevant media including Fed state simulated intestinal fluid (FeSSIF) at pH 5.0 and Fasted state simulated intestinal fluid (FaSSIF) at pH 6.5 at 37° C. The solids were magnetically stirred at 600 RPM in a shaker bath and samples were drawn with a 1.0 ml syringe at T=15 mins, 30 mins, 60 mins, 90 mins and 120 mins. The solubility was measured using HPLC method provided by the client. The compound was added to 4.0 ml glass vials at approximately 20.0 mg/ml. Samples were agitated with a vortex mixer for about 5 minutes to ensure the presence of undissolved excess powder. The sample collected at each time point was centrifuged at 1200 RPM, filtered with 0.45 μm Polytetrafluoroethylene (PTFE) filters and diluted with methanol before HPLC analysis. In order to minimize the effect of potential analyte adsorption on the filter, the initial 0.5 mL of supernatant passing through the filter was discarded prior to collecting sample for HPLC analysis.

Example 29—Preparation of Crystalline Obicetrapib Hydrochloride Form A

Obicetrapib HCl (approx. 43 mg, prepared consistent as disclosed herein) was combined with CPME/heptane (1:7) (0.8 mL) in a 1-dram vial and the mixture was magnetically stirred at room temperature. After 2 weeks, the solid was separated by centrifugation, the remaining liquid was removed via pipette. The sample was dried in a vacuum desiccator for approx. 30 min to give approximately 25 mg of Form A.

Example 30—Preparation of Crystalline Obicetrapib Hydrochloride Form B

Obicetrapib HCl (approx. 84 mg, prepared consistent as disclosed herein) was dissolved in 3.5 mL of toluene. Approximately 1 molar equivalent of hydrochloric acid (116 µL, 1 M solution in diethyl ether) was added to the solution upon stirring at room temperature. Heptane (4 mL) was then added to the mixture resulting in a cloudy solution within a few minutes. After stirring overnight, the suspension was vacuum filtered and the solid was briefly dried on the filter under reduced pressure to give approximately 40 mg of Form B (weighed after 26 days of ambient storage).

Example 31—Preparation of Crystalline Obicetrapib Hydrochloride Form C

Obicetrapib HCl (approx. 84 mg, prepared consistent as disclosed herein) was dissolved in 1.0 mL of isopropyl acetate. Approximately 1 molar equivalent of hydrochloric acid (116 µL, 1 M solution in diethyl ether) was added to the solution upon stirring at room temperature. Heptane (6 mL) was then added to the mixture resulting in a cloudy solution. After stirring overnight, the suspension was vacuum filtered and the solid was briefly dried on the filter under reduced pressure to give approximately 25 mg of Form C (weighed after 26 days of ambient storage).

Example 32—Preparation of Crystalline Obicetrapib Hydrochloride Form D

Obicetrapib HCl (approx. 46 mg, prepared consistent as disclosed herein) was combined with butyl acetate/heptane (1:5) (0.6 mL) in a 1-dram vial and the mixture was magnetically stirred at room temperature. After 2 weeks, the solid was separated by centrifugation, the remaining liquid was removed via pipette. The sample was dried in a vacuum desiccator for approx. 30 min to give approximately 15 mg of Form D.

Example 33—Preparation of Single Crystal Sample

Obicetrapib HCl (approximately 10 mg, prepared consistent as disclosed herein) was dissolved in a mixture of cyclopentyl methyl ether and heptane (1:8) (0.232 mL) upon heating at approximately 60° C. The resulting solution was cooled to 50-55° C. and left standing at that temperature overnight. The next day, some solids of acicular morphology were observed on the sides of vial. A temperature cycling experiment was conducted via successive heating-cooling: the sample was heated at 55-60° C., then cooled to 45-50° C. and held for several hours at that temperature. After approximately 5 days, agglomerated long blades were observed under the microscope and found to be of sufficient size and quality.

Example 34—Single Crystal Structure Solution

A colorless long blade-shaped crystal of a single crystal of Example 33 with formula $[4(C_{32}H_{32}F_9N_4O_5)\cdot 2(C_{32}H_{31}F_9N_4O_5)\cdot C_6H_{12}O\cdot C_7H_{16}\cdot 4(Cl)\cdot [+ \text{solvent}]]$ having approximate dimensions of 0.02×0.09×0.28 mm was mounted on a Mitegen micromesh mount in a random orientation. Data were collected from a shock-cooled single crystal at 150(2) K on a Bruker AXS D8 Quest four circle diffractometer with an I-mu-S microsource X-ray tube using a laterally graded multilayer (Goebel) mirror as monochromator and a PhotonIII_C14 charge-integrating and photon counting pixel array detector. The diffractometer used CuKα radiation ($\lambda$=1.54178 Å). All data were integrated with SAINT V8.40B and a multi-scan absorption correction using SADABS 2016/2 was applied (Bruker, SAINT, V8.40B, Bruker AXS Inc., Madison, Wisconsin, USA; L. Krause, R. Herbst-Irmer, G. M. Sheldrick, D. Stalke, J. Appl. Cryst. 2015, 48, 3-10, doi:10.1107/51600576714022985). The structure was solved by dual methods with SHELXT and refined by full-matrix least-squares methods against $F^2$ using SHELXL-2019/2 (G. M. Sheldrick, Acta Cryst. 2015, A71, 3-8, doi:10.1107/52053273314026370; G. M. Sheldrick, Acta Cryst. 2015, C71, 3-8, doi:10.1107/5205322961-4024218). All non-hydrogen atoms were refined with anisotropic displacement parameters. Carbon bound hydrogen atoms, carboxylic acid hydroxyl H atoms, and H atoms of most planar (sp2 hybridized) N—H groups were refined isotropically on calculated positions using a riding model. Methyl $CH_3$ and hydroxyl H atoms were allowed to rotate, but not to tip, to best fit the experimental electron density for more hydrogen atom treatment details). Uiso values were constrained to 1.5 times the Ueq of their pivot atoms for methyl and hydroxyl groups and 1.2 times for all other hydrogen atoms.

The asymmetric part of the structure consists of six major organic molecules, four chloride anions and several solvate molecules (methyl cyclopentyl ether and heptane). Four of the six major fragments are cationic, two are neutral molecules ("free base"). Protonation is at the "N3" nitrogen atom of the pyrimidine ring for all four cations, all four N—H+ units ionized and all four chloride anions ionized—two associated with the two N—H$^+$ units and the other with carboxyl moieties. The equivalent positions for the two free base molecules are not protonated and no close contacts to potential H-bond acceptors are observed.

Extensive disorder is observed for the entire structure, and some fragments exhibit very large thermal libration. This is more pronounced for the two free base molecules (residues 5 and 6), and especially their bis(trifluoromethyl)benzene moieties. Solvate molecules are extensively disordered and also display very large thermal libration and are only partially resolved.

All six major obicetrapib molecules (cations and free base) were restrained to have similar geometries. Minor disordered moieties were restrained to have similar geometries as a better defined fragment without disorder of another molecule (using SAME commands in Shelx1). All C—F bond distances and all F—C—F angles were each While the invention has been particularly shown and described with reference to a preferred embodiment and various alternate embodiments, it will be understood by persons skilled in the relevant art that various changes in form and details can be made therein without departing from the spirit and scope of the invention.

restrained to be similar to each other. Carbon atoms of the major and minor moieties of bis(trifluoromethyl)benzene moieties of residues 1, 2 and 3 and the mono(trifluoromethyl)benzene moiety of residue 3 were restrained to be close to planar (using FLAT commands in Shelx1). Atomic Displacement Parameters ("ADP") of the latter were restrained to be close to isotropic. Uij components of ADPs for atoms closer to each other than 2.0 Å were restrained to be similar. The position of one N—H+ H atom (H3A_3) was allowed to refine. Hydroxyl H-atoms of the carboxylic acids groups were allowed to rotate. Some were further restrained based on hydrogen bonding considerations. In the initial refinement cycles, a mild damping factor was applied. In the final refinement cycles some hydroxyl H atoms were set to ride on their carrying O atom (H4_1, H4_4, H4B_1), and the damping factor was removed.

Disorder was refined for the following fragments, and subject to the above conditions the occupancy ratios refined to:

Bis(trifluoromethyl)benzene moiety of residue 1 (cation). Occupancy ratio: 0.589(14) to 0.411(14).

Bis(trifluoromethyl)benzene moiety of residue 2 (cation). Occupancy ratio: 0.534(11) to 0.466(11).

Bis(trifluoromethyl)benzene and mono(trifluoromethyl) benzene moieties of residue 2 (cation). Occupancy ratio: 0.598(11) to 0.402(11) and 0.492(19) to 0.492 (19).

The 4-(pyrimidin-2-yloxy)butanoic acid fragment of residue 6 (free base). Occupancy ratio: 0.493(11) to 0.507 (11).

A methyl cyclopentyl ether solvate molecule was refined as fully occupied. Bond distances and angles were restrained to expected target values and Uij components of ADPs for atoms closer to each other than 2.0 Å were restrained to be similar. ADPs were restrained to be close to isotropic. A heptane solvate molecule was refined as disordered over two orientations. Bond distances and angles were restrained to expected target values and Uij components of ADPs for atoms closer to each other than 2.0 Å were restrained to be similar. A mild anti-bumping restraint was applied to avoid close contacts with main molecule atoms. Subject to these conditions, the occupancy ratio refined to 0.460(13) to 0.540(13).

The structure contains additional 980 Å$^3$ of solvent-accessible void volume. The two major void spaces (333 Å$^3$ each) likely contain ill-defined highly disordered solvate molecules. No substantial electron density peaks were found in the solvent accessible voids (less than 0.70 electrons per Å$^3$) and the residual electron density peaks are not arranged in a recognizable pattern. The structure factors were instead augmented via reverse Fourier transform methods using the SQUEEZE routine (A. L. Spek J. Appl. Cryst. 2003, 36, 7-13) as implemented in the program Platon (P. van der Sluis, & A. L. Spek, Acta Cryst. 1990, A46, 194-201). The SQUEEZE procedure accounted for 229 electrons within this volume, or about one heptane molecule for each of the two larger void spaces (100.2 electrons/heptane).

The Flack x parameter was determined using 4528 quotients [(I+)−(I−)]/[(I+)+(I−)] using Parsons' method and refined to 0.046(17) (S. Parsons, H. Flack, T. Wagner, Acta Cryst. 2013, B69, 249-259).

Example 35—X-ray Powder Diffraction Pattern

A Rigaku SmartLab X-Ray Diffractometer was configured in Bragg-Brentano reflection geometry equipped with a beam stop and knife edge to reduce incident beam and air scatter. Data collection parameters are shown in the following table (Table 12). This method has not been validated.

TABLE 12

PXRD Data Collection Parameters

| Parameter | Value | Parameter | Value |
| --- | --- | --- | --- |
| Geometry | Bragg-Brentano | Receiving Slit 1 (mm) | 18 |
| Tube Anode | Cu | Receiving Slit 2 (mm) | open |
| Tube Type | Long Fine Focus | Start Angle 2θ (°) | 2 |
| Tube Voltage (kV) | 40 | End Angle 2θ (°) | 40 |
| Tube Current (mA) | 44 | Step Size (°) | 0.02 |
| Detector | D/teX Ultra 250 | Scan Speed (°/min) | 6 |
| Monochromator | Ni foil Cu Kβ Filter | Spinning (rpm) | 11 |
| Incident Slit (°) | ⅓ | Sample Holder | Low-background Si |

Example 36 Calculated X-ray Powder Diffraction Pattern

An x-ray powder diffraction pattern was calculated from the single crystal structure solution of Example 34. The pattern was generated using commercially available software called Mercury 3.3 (Build RC5) from the Cambridge Crystallographic Data Centre (CCDC).

A peak table associated with the calculated pattern is set forth below in Table 13.

TABLE 13

| °2θ | Intensity |
| --- | --- |
| 4.4200 | 10000.0000 |
| 5.6200 | 1145.6800 |
| 6.2200 | 1759.7100 |
| 6.5200 | 697.5290 |
| 7.6600 | 9605.2400 |
| 7.9800 | 1023.2900 |
| 8.8400 | 1171.4300 |
| 9.2200 | 792.1080 |
| 9.6200 | 2634.8600 |
| 9.9600 | 3868.8400 |
| 9.9600 | 3868.8400 |
| 9.9600 | 3868.8400 |
| 9.9600 | 3868.8400 |
| 10.4000 | 2215.2200 |
| 10.6600 | 264.3710 |
| 11.0200 | 1021.6400 |
| 11.2400 | 305.5850 |
| 12.0400 | 253.4960 |
| 12.4800 | 2735.9800 |
| 12.7600 | 1504.7400 |
| 13.0800 | 862.2060 |
| 13.8600 | 1123.0400 |
| 14.0600 | 314.6310 |
| 14.4200 | 1565.2400 |
| 14.8600 | 865.3020 |
| 15.0600 | 1666.3600 |
| 15.3400 | 1000.5000 |
| 15.5200 | 562.2380 |
| 15.9800 | 1142.5400 |
| 16.1600 | 1360.5200 |
| 16.6400 | 1908.8000 |
| 16.8600 | 987.9160 |
| 17.5800 | 245.6010 |
| 18.0600 | 478.2430 |
| 18.2800 | 1589.6800 |
| 18.2800 | 1589.6800 |
| 18.2800 | 1589.6800 |
| 18.8200 | 1598.5700 |
| 19.0400 | 1975.1200 |
| 19.3200 | 1423.8100 |

TABLE 13-continued

| °2θ | Intensity |
|---|---|
| 19.4800 | 1083.0500 |
| 19.7400 | 678.2880 |
| 20.0600 | 709.5890 |
| 20.4000 | 2157.3300 |
| 20.6600 | 1813.0000 |
| 20.8800 | 1772.4200 |
| 21.2000 | 1789.0000 |
| 21.7600 | 1119.4600 |
| 21.9200 | 2205.1500 |
| 22.2200 | 975.3100 |
| 22.5800 | 2985.5700 |
| 22.8600 | 1007.1600 |
| 23.3000 | 814.9970 |
| 23.9400 | 683.9720 |
| 24.1200 | 829.9130 |
| 24.6800 | 1247.7000 |
| 24.8600 | 1296.2800 |
| 25.1000 | 648.0530 |
| 25.3200 | 507.7400 |
| 25.5800 | 445.3830 |
| 26.0000 | 946.7810 |
| 26.1600 | 1041.7700 |
| 26.3400 | 546.9870 |
| 26.4800 | 604.3340 |
| 26.7000 | 469.4680 |
| 27.0600 | 492.8890 |
| 27.4000 | 332.6250 |
| 27.6800 | 455.0290 |
| 27.9600 | 199.6810 |
| 28.3400 | 332.0320 |
| 28.6200 | 365.2220 |
| 28.8800 | 471.0800 |
| 29.2400 | 292.9540 |
| 29.4000 | 257.7320 |
| 29.7800 | 354.9840 |
| 30.2200 | 332.0360 |
| 30.9600 | 208.9090 |
| 31.3600 | 267.6430 |
| 31.5600 | 522.9010 |
| 31.8400 | 194.5010 |
| 32.2600 | 293.8370 |
| 32.7400 | 449.6300 |
| 33.0800 | 297.8490 |
| 33.4200 | 328.0350 |
| 34.0600 | 196.6250 |
| 34.4800 | 250.5200 |
| 34.6600 | 323.5840 |
| 35.2400 | 117.9280 |
| 35.5000 | 169.8870 |
| 35.9800 | 136.5220 |
| 36.3000 | 118.8480 |
| 36.7400 | 203.7700 |
| 37.1600 | 135.4460 |
| 37.4600 | 139.9870 |
| 37.7200 | 191.7900 |
| 38.2600 | 260.9170 |

All references, issued patents and patent applications cited within the body of the instant specification are hereby incorporated by reference in their entirety, for all purposes.

What is claimed is:

1. Amorphous obicetrapib hemicalcium.

2. The amorphous obicetrapib hemicalcium of claim 1, having an x-ray powder diffraction pattern comprising one or more peaks at about 3.4° 2θ, about 7.0° 2θ, and about 9.2° 2θ.

3. The amorphous obicetrapib hemicalcium of claim 1, having a glass transition temperature at a value between about 109° C. and about 112° C., when measured by modulated differential scanning calorimetry in a sample pan with an opening.

4. The amorphous obicetrapib hemicalcium of claim 2, having a glass transition temperature at a value between about 109° C. and about 112° ° C., when measured by modulated differential scanning calorimetry in a sample pan with an opening.

5. The amorphous obicetrapib hemicalcium of claim 1, having a solid-state $^{13}$C-NMR spectrum substantially the same as that of FIG. 17.

6. The amorphous obicetrapib hemicalcium of claim 1, having a solid-state $^{13}$C-NMR spectrum where no peak is present at either about 22.1 ppm or about 29.5 ppm.

7. The amorphous obicetrapib hemicalcium of claim 2, having a solid-state $^{13}$C-NMR spectrum substantially the same as that of FIG. 17.

8. The amorphous obicetrapib hemicalcium of claim 2, having a solid-state $^{13}$C-NMR spectrum where no peak is present at either about 22.1 ppm or about 29.5 ppm.

9. The amorphous obicetrapib hemicalcium of claim 3, having a solid-state $^{13}$C-NMR spectrum substantially the same as that of FIG. 17.

10. The amorphous obicetrapib hemicalcium of claim 3, having a solid-state $^{13}$C-NMR spectrum where no peak is present at either about 22.1 ppm or about 29.5 ppm.

11. The amorphous obicetrapib hemicalcium of claim 4, having a solid-state $^{13}$C-NMR spectrum substantially the same as that of FIG. 17.

12. The amorphous obicetrapib hemicalcium of claim 4, having a solid-state $^{13}$C-NMR spectrum where no peak is present at either about 22.1 ppm or about 29.5 ppm.

13. The amorphous obicetrapib hemicalcium of claim 1, having a d90 particle size distribution of between 6 and 15 microns.

14. The amorphous obicetrapib hemicalcium of claim 2, having a d90 particle size distribution of between 6 and 15 microns.

15. The amorphous obicetrapib hemicalcium of claim 3, having a d90 particle size distribution of between 6 and 15 microns.

16. The amorphous obicetrapib hemicalcium of claim 4, having a d90 particle size distribution of between 6 and 15 microns.

17. The amorphous obicetrapib hemicalcium of claim 1, having a chemical purity of at least 99.0%.

18. The amorphous obicetrapib hemicalcium of claim 2, having a chemical purity of at least 99.0%.

19. The amorphous obicetrapib hemicalcium of claim 17, having a chemical purity of at least 99.9%.

20. The amorphous obicetrapib hemicalcium of claim 18, having a chemical purity of at least 99.9%.

21. The amorphous obicetrapib hemicalcium of claim 1, having an x-ray powder diffraction pattern substantially the same as that of FIG. 3.

22. The amorphous obicetrapib hemicalcium of claim 1, wherein the amorphous obicetrapib calcium does not birefringe.

23. The amorphous obicetrapib hemicalcium of claim 2, wherein the amorphous obicetrapib calcium does not birefringe.

24. The amorphous obicetrapib hemicalcium of claim 3, wherein the amorphous obicetrapib calcium does not birefringe.

25. The amorphous obicetrapib hemicalcium of claim 1, wherein the obicetrapib hemicalcium is milled.

26. The amorphous obicetrapib hemicalcium of claim 1, having a water content of less than about 4%.

27. The amorphous obicetrapib hemicalcium of claim 26, having a water content of between about 0.5% and about 1.5%.

* * * * *

UNITED STATES PATENT AND TRADEMARK OFFICE
CERTIFICATE OF CORRECTION

| | |
|---|---|
| PATENT NO. | : 12,006,305 B2 |
| APPLICATION NO. | : 18/346342 |
| DATED | : June 11, 2024 |
| INVENTOR(S) | : Cui et al. |

It is certified that error appears in the above-identified patent and that said Letters Patent is hereby corrected as shown below:

In the Claims

In Column 80, in Claim 4, Line 1, delete "112° ° C.," and insert -- 112° C., --, therefor.

Signed and Sealed this
Tenth Day of September, 2024

Katherine Kelly Vidal
*Director of the United States Patent and Trademark Office*